Figure 2A:
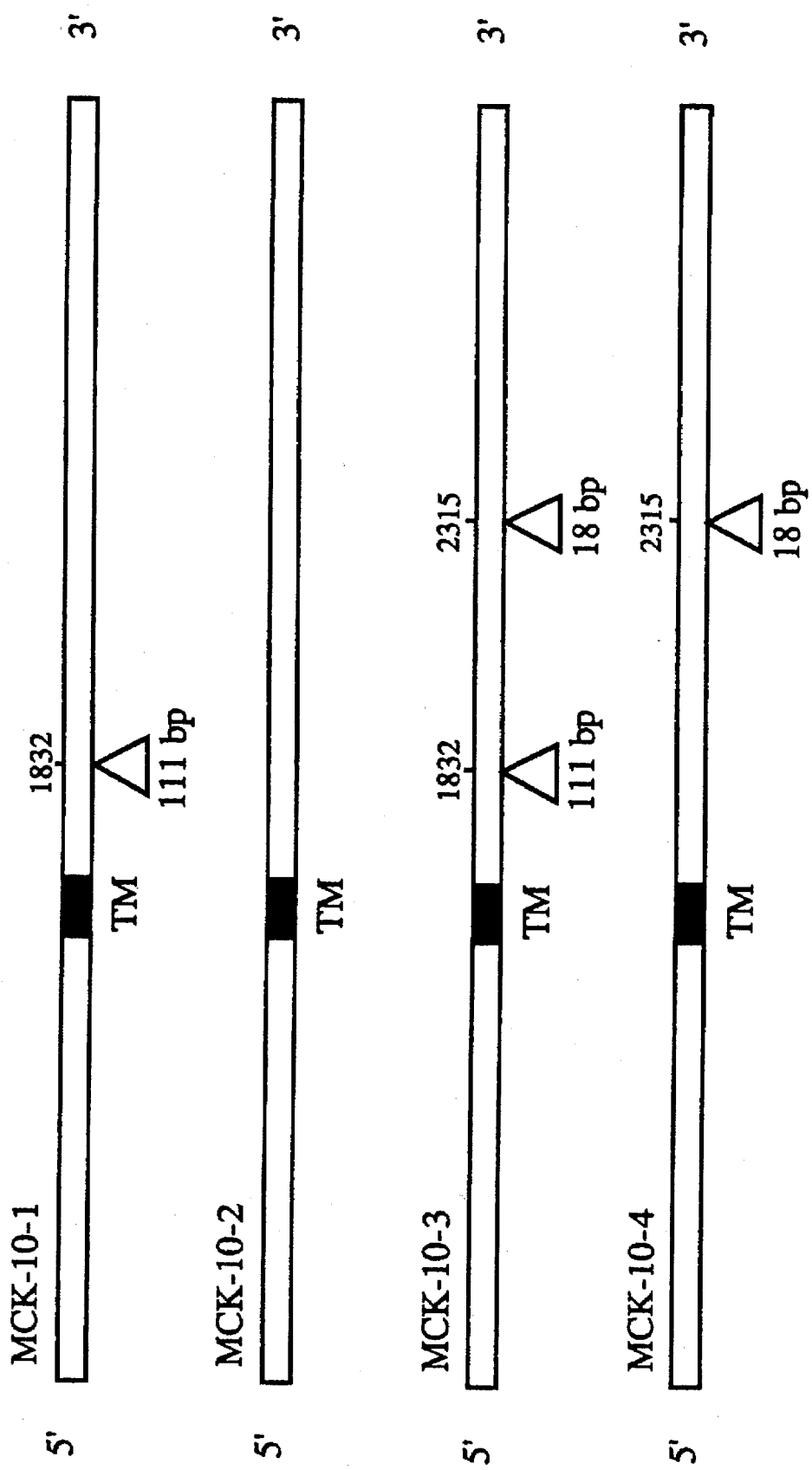

United States Patent [19]

Ullrich et al.

[11] Patent Number: 5,677,144
[45] Date of Patent: Oct. 14, 1997

[54] RECOMBINANT DNA ENCODING CCK 2, A RECEPTOR TYROSINE KINASE

[76] Inventors: Axel Ullrich, Adalbertstr. 108, München; Frauke Hildegard Elisabeth Alves, Rohnsweg 2, Göttingen, both of Germany

[21] Appl. No.: 336,343

[22] Filed: Nov. 8, 1994

Related U.S. Application Data

[63] Continuation-in-part of Ser. No. 153,397, Nov. 16, 1993.

[51] Int. Cl.$^6$ .................. C07K 14/705; C12N 15/62; C12N 15/12
[52] U.S. Cl. .................. 435/69.1; 435/69.7; 435/257.3; 435/320.1; 530/350; 536/23.4; 536/23.5
[58] Field of Search .................. 435/69.1, 69.7, 435/252.3, 320.1; 530/350; 536/23.4, 23.5

[56] References Cited

PUBLICATIONS

Karn et al., *Oncogene* 8(12): 3433–3440, Dec. 1993.

*Primary Examiner*—John Ulm
*Attorney, Agent, or Firm*—Pennie & Edmonds

[57] ABSTRACT

A recombinant nucleic acid molecule encoding a receptor tyrosine kinase identified herein as CCK-2, and specific functional fragments thereof are provided. Also, provided is a nucleic acid encoding a chimeric protein comprising all or a specific part of CCK-2, as well as a process of employing the disclosed nucleic acids to produce the proteins encoded thereby.

25 Claims, 31 Drawing Sheets

```
  1  CGGGCCTGAGACTGGGGTGAGCCTGGGACCTAAGAGAATCCTGAGCTGGAGGCCCCCGACAG
 61  CTGCTCTCGGGAGCCGGCTCCCTCCTCCCGACACCCGAGCCGCTCCTCCCGCTCCCGGCTC
121  CCGGCTCCTGCCTCCGCTCCCTCCGCCCTCGCCCCCGCGCCCGCCCGAAGAGGCCCCGCT
181  CCCGGGTCGGACGCCTGGGTCTGCGGGAGTCGGATGAGAGCCGATGAGAGGTGTCTGAAGGTGGCTAT
241  TCACTGAGCCGATGGGGTTGGAGTTGGACTTGAAGGAATGCCAAGAGATGCTGCCCCACCCCCTTA

1                    M  G  P  E  A  L  S  S  L  L  L  L  L  L
301  GGCCCGAGGGATCAGGAGCTATGGGACCAGAGCTCTGTCATCTTTACTGCTGCTCT

15   V  A  S  G  D  A  D  M  K  G  H  F  D  P  A  K  C  R  Y  A
361  TGGTGGCAAGTGGAGATGCTGACATGAAGGGACATTTTGATCCTGCCAAGTGCCGCTATG

35   L  G  M  Q  D  R  T  I  P  D  S  D  I  S  A  S  S  S  W  S
421  CCCTGGGCATGCAGGACCGGACCATCCCAGACAGTGACATCTCTGCTTCCAGCTCCTGGT

55   D  S  T  A  A  R  H  S  R  L  E  S  S  D  G  D  G  A  W  C
481  CAGATTCCACTGCCGCCCGCCACAGCAGGTTGGAGAGCAGTGACGGGGATGGGGCCTGGT

75   P  A  G  S  V  F  P  K  E  E  Y  L  Q  V  D  L  Q  R  L
541  GCCCCGGCAGGGTCGGTGTTCCCAAGGAGGAGTACTTGCAGGTGGATCTACAACGAC

95   H  L  V  A  L  V  G  T  Q  G  R  H  A  G  G  L  G  K  E  F
601  TCCACCTGGTGGCTCTGGTGGGCACCCAGGGACGGCATGCCGGGGGCCTGGGGAAGGAGT
```

FIG. 1A

```
115        S   R   S   Y   R   L   R   Y   S   R   D   G   R   R   W   M   G   W   K   D
661        TCTCCCGGAGCTACCGGCTGCGTTACTCCCGGGATGGTCGCCGCTGGATGGGCTGGAAGG

135        R   W   G   Q   E   V   I   S   G   N   E   D   P   E   G   V   V   L   K   D
721        ACCGCTGGGGTCAGGAGGTGATCTCAGGCAATGAGGACCCTGAGGAGTGGTGCTGAAGG

155        L   G   P   P   M   V   A   R   L   V   R   F   Y   P   R   A   D   R   V   M
781        ACCTTGGGCCCCCATGGTTGCCCGACTGGTTCGCTTCTACCCCCGGGCTGACCGGGTCA

175        S   V   C   L   R   V   E   L   Y   G   C   L   W   R   D   G   L   L   S   Y
841        TGAGTGTCTGTCTGCGGGTAGAGCTCTATGGCTGCCTCTGGAGGGATGGACTCCTGTCTT

195        T   A   P   V   G   Q   T   M   Y   L   S   E   A   V   Y   L   N   D   S   T
901        ACACCGCCCCTGTGGGCCAGACAATGTATTTATCTGAGGCCGTGTACCTCAACGACTCCA

215        Y   D   G   H   T   V   G   G   L   Q   Y   G   G   L   G   Q   L   A   D   G
961        CCTATGACGGACATACCGTGGGGCGGACTGCAGTATGGGGGTCTGGGCCAGCTGGCAGATG

235        V   V   G   L   D   D   F   R   K   S   Q   E   L   R   V   W   P   G   Y   D
1021       GTGTGGTGGGGCTGGATGACTTTAGGAAGAGTCAGGAGCTGCGGGTCTGGCCAGGCTATG

255        Y   V   G   W   S   N   H   S   F   S   S   G   Y   V   E   M   E   F   E   F
1081       ACTATGTGGGATGGAGCAACCACAGCTTCTCCAGTGGCTATGTGGAGATGGAGTTTGAGT
```

FIG.1B

FIG.1C

```
275   D   R   L   R   A   F   Q   A   M   Q   V   H   C   N   N   M   H   T   L   G
1141  TTGACCGGGCTGAGGCCTTCCAGGCTATGCAGGTCCACTGTAACAACATGCACACGCTGG

295   A   R   L   P   G   G   V   E   C   R   F   R   R   G   P   A   M   A   W   E
1201  GAGCCCGTCTGCCTGGGCGGGGTGGAATGTCGCTTCCGGCGTGGCCCTGCCATGGCCTGGG

315   G   E   P   M   R   H   N   L   G   G   N   L   G   D   P   R   A   R   A   V
1261  AGGGGGAGCCCATGCGCCACAACCTAGGGGGCAACCTGGGGGACCCCAGAGCCCGGGCTG

335   S   V   P   L   G   G   R   V   A   R   F   L   Q   C   R   F   L   F   A   G
1321  TCTCAGTGCCCCTTGGGCGGCCGTGTGGCCCGCTTTCTGCAGTGCCGCTTCCTCTTTGCGG

355   P   W   L   L   F   S   E   I   S   F   I   S   D   V   V   N   N   S   S   P
1381  GGCCCTGGTTACTCTTCAGCGAAATCTCCTTCATCTCTGATGTGGTGAACAATTCCTCTC

375   A   L   G   G   T   F   P   P   A   P   W   P   P   G   P   P   P   T   N
1441  CGGCACTGGGAGGCACCTTCCCGGCCAGCCCTGGTGGCCCTGGCCCTCCCACCA

395   F   S   S   L   E   L   E   P   R   G   Q   Q   P   V   A   K   A   E   G   S
1501  ACTTCAGCAGCTTGGAGCTGGAGCCCAGAGGCCAGCAGCCCGTGGCCAAGGCCGAGGGGA

415   P   T   A   I   L   I   G   C   L   V   A   I   I   L   L   L   L   I   I
1561  GCCCGACCGCCATCCTCATCGGCTGCCTGGTGGCCATCATCCTCCTGCTGCTCATCA
```

```
435   A  L  M  L  W  R  L  H  W  R  R  L  L  S  K  A  E  R  R  V
1621  TTGCCCCTCATGCTCTCTGGCGCTGCACTGGCGCAGGCTCCTCAGCAAGGCTGAACGGAGGG

455   L  E  E  E  L  T  V  H  L  S  V  P  G  D  T  I  L  I  N  N
1681  TGTTGGAAGAGGAGCTGACGGTTCACCTCTGTCCCTGGGACACTATCCTCATCAACA

475   R  P  G  P  R  E  P  P  Y  Q  E  P  P  R  G  N  P  P
1741  ACCGCCCAGGTCCTAGAGAGCCACCCCGTACCAGGAGCCCCGGCCTGTGGGAATCCGC

495   H  S  A  P  C  V  P  N  G  S  A  L  L  L  S  N  P  A  Y  R
1801  CCCACTCCGCTCCCTGTGTCCCCAATGGCTCTGCGTTGCTCTCCAATCCAGCCTACC

515   L  L  L  A  T  Y  A  R  P  P  R  G  P  P  T  P  A  W
1861  GCCTCCTTCTGGCCACTTACGCCCGTCCCCCTCGAGCCCCCACACCCGCCT

535   A  K  P  T  N  T  Q  A  Y  S  G  D  Y  M  E  P  E  K  P  G
1921  GGGCCAAACCCACCAACACCCAGGCCTACAGTGGGGACTATATGGAGCCTGAGAAGCCAG

555   A  P  L  L  P  P  P  Q  N  S  V  P  H  Y  A  E  A  D  I
1981  GCGCCCCGCTTCTGCCCCCACCCCAGAACAGCGTCCCCATTATGCCGAGGCTGACA

575   V  T  L  Q  G  V  T  G  G  N  T  Y  A  V  P  A  L  P  P  G
2041  TTGTTACCCTGCAGGGCGTCACCGGGGGCAACACCTATGCTGTGCCTGCACTGCCCCCAG
```

FIG.1D

```
595   A   V   G   D   G   P   P   R   V   D   F   P   P   R   S   R   L   R   F   K   E
2101  GGGCAGTCGGGGGATGGGCCCCCCAGAGTGGATTTCCCTCGATCTCGACTTCGCTTCAAGG

615   K   L   G   E   G   Q   F   G   E   V   H   L   C   E   V   D   S   P   Q   D
2161  AGAAGCTTGGCGAGGGCCAGTTTGGGGAGGTGCACCTGTGTGAGGTCGACAGCCCTCAAG

635   L   V   S   L   D   F   P   L   N   V   R   K   G   H   P   L   L   V   A   V
2221  ATCTGGTCAGTCTTGATTTCCCCCTTAATGTGCGTAAGGACACCCTTTGCTGGTAGCTG

655   K   I   L   R   P   D   A   T   K   N   A   S   F   S   L   F   S   R   N   D
2281  TCAAGATCTTACGGCCAGATGCCACCAAGAATGCCAGCTTCTCCTTGTTCTCCAGGAATG

675   F   L   K   E   V   K   I   M   S   R   L   K   D   P   N   I   R   L   L
2341  ATTTCCTGAAAGAGGTGAAAGATCATGTCGAGGCTCAAGGACCCCAACATCATTCGGCTGC

695   G   V   C   V   Q   D   D   P   L   C   M   I   T   D   Y   M   E   N   G   D
2401  TGGGCGTGTGTGTGTGCAGGACGACCCTCTGCATGATTACTGACTACATGGAGAACGGCG

715   L   N   Q   F   L   S   A   H   Q   L   E   D   K   A   A   E   G   A   P   G
2461  ACCTCAACCAGTTCCTCAGTGCCCACCAGCTGGAGGACAAGGCAGCCGAGGGCCCCTG

735   D   G   Q   A   A   Q   G   P   T   I   S   Y   P   M   L   L   H   V   A   A
2521  GGGACGGGCAGGCAGGCTGCGCAGGGCCCCACCATCAGCTACCCAATGCTGCTCATGTGGCAG
```

FIG. 1E

```
755           Q   I   A   S   G   M   R   Y   L   A   T   L   N   F   V   H   R   D   L   A
2581         CCAGATGCGCCTCCGGCATGCGCTATCTGGCCACACTCAACTTTGTACATCGGGACCTGG

775           T   R   N   C   L   V   G   E   N   F   T   I   K   I   A   D   F   G   M   S
2641         CCACGCGGGAACTGCCTAGTTGGGGAAAATTCACCATCAAATCGCAGACTTTGGCATGA

795           R   N   L   Y   A   G   D   Y   Y   R   V   Q   G   R   A   V   L   P   I   R
2701         GCCGGAACCTCTATGCTGGGGACTATTACCGTGTGCAGGGCAGTGCCTGCCCATCC

815           W   M   A   W   E   C   I   L   M   G   K   F   T   A   S   D   V   W   A
2761         GCTGGATGGCCTGGGAGTGCATCCTCATGGGGAAGTTCACGACTGCGAGTGACGTGTGGG

835           F   G   V   T   L   W   E   V   L   M   L   C   R   A   Q   P   F   G   Q   L
2821         CCTTTGGTGTGACCCTGTGGGAGGTGCTGATGCTCTGTAGGGCCCAGCCCTTTGGGCAGC

855           T   D   E   Q   V   I   E   N   A   G   E   F   F   R   D   Q   G   R   Q   V
2881         TCACCGACGAGCAGGTCATCGAGAACGCGGGGAGTTCTTCCGGGACCAGGGCCGGCAGG

875           Y   L   S   R   P   P   A   C   P   Q   G   L   Y   E   L   M   L   R   C   W
2941         TGTACCTGTCCCGCCCCGCCTGCCCCCAGGGCCTATATGAGCTGATGCTTCGGTGCT

895           S   R   E   S   E   Q   R   P   P   F   S   Q   L   H   R   F   L   A   E   D
3001         GGAGCCGGGAGTCTGAGCAGCGACCACCCTTTTCCCAGCTGCATCGGTTCCTGGCAGAGG
```

FIG.1F

```
                A  L  N  T  V
 915   ATGCACTCAACACGGTGTGAATCACACATCCAGCTGCCCCTCCCCTCAGGGAGTGATCCAG
3061   GGGAAGCCAGTGACACTAAAACAAGAGGACACCTCTGCCCTTCCCCTCCCGA
3121   CAGCCCATCACCTCTAATAGAGGCAGTGAGACTGAGACTGCAGGTGGGCTGGGCCCACCCAGGGAG
3181   CTGATGCCCCTCTTCTCCCCTTCCTGGACACACTCTCATGTCCCCTTCCTGTTCTTCCTTCC
3241   TAGAAGCCCCCTGTCGCCCACCCAGCTTCCTGTGGATGGGATCCTCTCCACCCCTCCTCT
3301   AGCCATCCCTTGGGGCCCCACTGGAAGGGTGGGAGAGAATATAGGATAGACACTGGACATGCCCCATTG
3361   GAGCACCTGGGCTGGACACTGGACCCCACTGGCTGAGAATCTGGGGGTGAGGAGGACAAGA
3421   TCTCTCCCTGTCACACACTGACACCTCTTGTGCCTGGCTGAGACTGGCTGCTTGGCTTCTTC
3481   AGGAGGAGAAAATGTTCCTTGTGTCCTGCTCCCTGTACTTGTGTCCTCAGCTTGGCTTCTTC
3541   CTCCCCATCACCTGAAACACTGGACCTGGGGGTAGCCCCGCCCCCAGCCCCTCAGTCACCC
3601   CCACTTCCCACTTGCAGTCTCTGTAGCTAGAACTTCTAAGCCTATACGTTTCTGTGGAG
3661   TAAATATTGGGATTGGGGGCCACATTGATTTCTATAATCACTGGGGTTTGTACATTTTGGGG
3721   TCTAGTGTAGCTGCACAGATTTTACACTAATAATATATGGACCTAGCTTGAGGCAATTTAATCCCT
3781   GGAGAGACACAGGTAATAATAAAGGTTGAGTTTTCCACAAAAAAAAAAACCGGAAT
3841   GCACTAGGCAGGTAATAATAAAGGTTGAGTTTTCCACAAAAAAAAAAAACCGGAAT
3901   
3961   TC
```

FIG.1G

```
MCK-10-2  501 PNGS........................................AYSGDYMEP  5
              ||||                   _____              |||||||||
MCK-10-1  501 PNGSALLLSNPAYRLLLATYARPPRGPGPPTPAWAKPTNTQAYSGDYMEP  5

MCK-10-2  614 LVAVKILRPDATKNA......RNDFLKEVKIMSRLKDPNIIRLLGVCVQD  6
              ||||||||||||||       |||||||||||||||||||||||||||||
MCK-10-3  651 LVAVKILRPDATKNASFSLFSRNDFLKEVKIMSRLKDPNIIRLLGVCVQD  7
```

FIG.2B

```
     gcacgagcggcacgagtccatgatctctttccatcctcccttttcctgtttgctcacttct
  2  ————+————+————+————+————+————+— 61
     cgtgctcgccgtgctcaggtactagagaaaggtaggagggaaaggactttcgagtgaaga
  b                                                                — tttcttgctcatcttggagactgtgcaatcccagattaactacaaacagagaagagctgg
 62  ————+————+————+————+————+————+— 121
     aaagaacgagtagaacctctgacacgttagggtctaattgatgtttgtctcttctcgacc
  b                                                                — tgatagctccagagctcagagaaaggaggtctctttacaagaagtctggctctcaaagcc
122  ————+————+————+————+————+————+— 181
     actatcgaggtctcgagtctctttcctccagagaaatgttcttcagaccgagagtttcgg
  b                                                                — tccatcaagggagacctacaagttgcctggggttcagtgctctagaaagttccaaggttt
182  ————+————+————+————+————+————+— 241
     aggtagttccctctggatgttcaacggaccccaagtcacgagatctttcaaggttccaaa
  b                                                                — gtggcttgaattattctaaagaagctgaaataattgaagagaagcagaggccagctgttt
242  ————+————+————+————+————+————+— 301
     caccgaacttaataagatttcttcgactttattaacttctcttcgtctccggtcgacaaa
  b                                                                — ttgaggatcctgctccacagagaatgctctgcacccgttgatactccagttccaacacca
302  ————+————+————+————+————+————+— 361
     aactcctaggacgaggtgtctcttacgagacgtgggcaactatgaggtcaaggttgtggt
  b                                                                — tcttctgagatgatcctgattcccagaatgctcttggtgctgttcctgctgctgcctatc
362  ————+————+————+————+————+————+— 421
     agaagactctactaggactaagggtcttacgagaaccacgacaaggacgacgacggatag
  b         H  I  L  I  P  R  M  L  L  V  L  F  L  L  L  P  I     — ttgagttctgcaaaagctcaggttaatccagctatatgccgctatcctctgggcatgtca
422  ————+————+————+————+————+————+— 481
     aactcaagacgttttcgagtccaattaggtcgatatacggcgataggagacccgtacagt
  b     L  S  S  A  K  A  Q  V  N  P  A  I  C  R  Y  P  L  G  M  S  — ggaggccagattccagatgaggacatcacagcttccagtcagtggtcagagtccacagct
482  ————+————+————+————+————+————+— 541
     cctccggtctaaggtctactcctgtagtgtcgaaggtcagtcaccagtctcaggtgtcga
  b     G  G  Q  I  P  D  E  D  I  T  A  S  S  Q  W  S  E  S  T  A  —
```

FIG.3A

```
        gccaaatatggaaggctggactcagaagaaggggatggagcctggtgccctgagattcca
    542 ────────┼────────┼────────┼────────┼────────┼────────┼──  601
        cggtttatoccttccgacctgagtcttcttcccctacctcggaccacgggactctaaggt b        A  K  Y  G  R  L  D  S  E  E  G  D  G  A  W  C  P  E  I  P     - gtggaacctgatgacctgaaggagtttctgcagattgacttgcacaccctccatttatc
    602 ────────┼────────┼────────┼────────┼────────┼────────┼──  661
        caccttggactactggacttcctcaaagacgtctaactgaacgtgtgggaggtaaaatag b        V  E  P  D  D  L  K  E  F  L  Q  I  D  L  H  T  L  H  F  I     - actctggtggggacccaggggcgccatgcaggaggtcatggcatcgagtttgcccccatg
    662 ────────┼────────┼────────┼────────┼────────┼────────┼──  721
        tgagaccacccctgggtccccgcggtacgtcctccagtaccgtagctcaaacgggggtac b        T  L  V  G  T  Q  G  R  H  A  G  G  H  G  I  E  F  A  P  M     - tacaagatcaattacagtcgggatggcactcgctggatctcttggcggaaccgtcatggg
    722 ────────┼────────┼────────┼────────┼────────┼────────┼──  781
        atgttctagttaatgtcagccctaccgtgagcgacctagagaaccgccttggcagtaccc b        Y  K  I  N  Y  S  R  D  G  T  R  W  I  S  W  R  N  R  H  G     - aaacaggtgctggatggaaatagtaacccctatgacatttttcctaaaggacttggagccg
    762 ────────┼────────┼────────┼────────┼────────┼────────┼──  841
        tttgtccacgacctaccttatcattggggatactgtaaaaggattttcctgaacctcggc b        K  Q  V  L  D  G  N  S  N  P  Y  D  I  F  L  K  D  L  E  P     - cccattgtagccagatttgtccggttcattccagtcaccgaccactccatgaatgtgtgt
    842 ────────┼────────┼────────┼────────┼────────┼────────┼──  901
        gggtaacatcggtctaaacaggccaagtaaggtcagtggctggtgaggtacttacacaca b        P  I  V  A  R  F  V  R  F  I  P  V  T  D  H  S  M  N  V  C     - atgagagtggagctttacggCTGTGTCTGGCTAGATGGCTTGGTGTCTTACAATGCTCCA
    902 ────────┼────────┼────────┼────────┼────────┼────────┼──  961
        tactctcacctcgaaatgccGACACAGACCGATCTACCGAACCACAGAATGTTACGAGGT b        M  R  V  E  L  Y  G  C  V  W  L  D  G  L  V  S  Y  N  A  P     -
```

FIG.3B

```
       GCTGGGCAGCAGTTTGTACTCCCTGGAGGTTCCATCATTTATCTGAATGATTCTGTCTAT
  962  ------+---------+---------+---------+---------+---------+-  1021
       CGACCCGTCGTCAAACATGAGGGACCTCCAAGGTAGTAAATAGACTTACTAAGACAGATA b      A  G  Q  Q  F  V  L  P  G  G  S  I  I  Y  L  N  D  S  V  Y    -

GATGGAGCTGTTGGATACAGCATGACAGAAGGGCTAGGCCAATTGACCGATGGTGTGTCT
 1022  ------+---------+---------+---------+---------+---------+-  1081
       CTACCTCGACAACCTATGTCGTACTGTCTTCCCGATCCGGTTAACTGGCTACCACACAGA b      D  G  A  V  G  Y  S  M  T  E  G  L  G  Q  L  T  D  G  V  S    -

GGCCTGGACGATTTCACCCAGACCCATGAATACCACGTGTGGCCCGGCTATGACTATGTG
 1082  ------+---------+---------+---------+---------+---------+-  1141
       CCGGACCTGCTAAAGTGGGTCTGGGTACTTATGGTGCACACCGGGCCGATACTGATACAC b      G  L  D  D  F  T  Q  T  H  E  Y  H  V  W  P  G  Y  D  Y  V    -

GGCTGGCGGAACGAGAGTGCCACCAATGGCTACATTGAGATCATGTTTGAATTTGACCGC
 1142  ------+---------+---------+---------+---------+---------+-  1201
       CCGACCGCCTTGCTCTCACGGTGGTTACCGATGTAACTCTAGTACAAACTTAAACTGGCG b      G  W  R  N  E  S  A  T  N  G  Y  I  E  I  M  F  E  F  D  R    -

ATCAGGAATTTCACTACCATGAAGGTCCACTGCAACAACATGTTTGCTAAAGGTGTGAAG
 1202  ------+---------+---------+---------+---------+---------+-  1261
       TAGTCCTTAAAGTGATGGTACTTCCAGGTGACGTTGTTGTACAAACGATTTCCACACTTC b      I  R  N  F  T  T  M  K  V  H  C  N  N  M  F  A  K  G  V  K    -

ATCTTTAAGGAGGTACAGTGCTACTTCCGCTCTGAAGCCAGTGAGTGGGAACCTAATGCC
 1262  ------+---------+---------+---------+---------+---------+-  1321
       TAGAAATTCCTCCATGTCACGATGAAGGCGAGACTTCGGTCACTCACCCTTGGATTACGG b      I  F  K  E  V  Q  C  Y  F  R  S  E  A  S  E  W  E  P  N  A    -

ATTTCCTTcccccttgtcctggatgacgtcaaccccagtgctcggtttgtcacggtgcct
 1322  ------+---------+---------+---------+---------+---------+-  1381
       TAAAGGAAggggggaacaggacctactgcagttggggtcacgagccaaacagtgccacgga b      I  S  F  P  L  V  L  D  D  V  N  P  S  A  R  F  V  T  V  P    -
```

FIG.3C

```
      ctccaccaccgaatggccagtgccatcaagtgtcaataccattttgcagatacctggatg
 1382 ------+------+------+------+------+------+ 1441
      gaggtggtggcttaccggtcacggtagttcacagttatggtaaaacgtctatggacctac b     L  H  H  R  M  A  S  A  I  K  C  Q  Y  H  F  A  D  T  W  M   - atgttcagtgagatcaccttccaatcagatgctgcaatgtacaacaactctgaagccctg
 1442 ------+------+------+------+------+------+ 1501
      tacaagtcactctagtggaaggttagtctacgacgttacatgttgttgagacttcgggac b     M  F  S  E  I  T  F  Q  S  D  A  A  M  Y  N  N  S  E  A  L   - cccacctctcctatggcacccacaacctatgatccaatgcttaaagttgatgacagcaac
 1502 ------+------+------+------+------+------+ 1561
      gggtggagaggataccgtgggtgttggatactaggttacgaatttcaactactgtcgttg b     P  T  S  P  M  A  P  T  T  Y  D  P  M  L  K  V  D  D  S  N   - actcggatcctgattggctgcttggtggccatcatctttatcctcctggccatcattgtc
 1562 ------+------+------+------+------+------+ 1621
      tgagcctaggactaaccgacgaaccaccggtagtagaaataggaggaccggtagtaacag b     T  R  I  L  I  G  C  L  V  A  I  I  F  I  L  L  A  I  I  V   - atcatcctctggaggcagttctggcagaaaatgctggagaaggcttctcggaggatgctg
 1622 ------+------+------+------+------+------+ 1681
      tagtaggagacctccgtcaagaccgtctttacgacctcttccgaagagcctcctacgac b     I  I  L  W  R  Q  F  W  Q  K  M  L  E  K  A  S  R  R  M  L   - gatgatgaaatgacagtcagcctttccctgccaagtgattccagcatgttcaacaataac
 1682 ------+------+------+------+------+------+ 1741
      ctactactttactgtcagtcggaaagggacggttcactaagatcgtacaagttgttattg b     D  D  E  M  T  V  S  L  S  L  P  S  D  S  S  M  F  N  N  N   - cgctcctcatcacctagtgaacaagggtccaactcgacttacgatcgcatctttcccctt
 1742 ------+------+------+------+------+------+ 1801
      gcgaggagtagtggatcacttgttcccaggttgagctgaatgctagcgtagaaaggggaa b     R  S  S  S  P  S  E  Q  G  S  N  S  T  Y  G  R  I  F  P  L   -
```

FIG.3D

```
     cgccctgactacCAGGAGCCATCCAGGCTGATACGAAAACTCCCAGAATTTGCTCCAGGG
1802 ------+------+------+------+------+------+- 1861
     gcgggactgatgGTCCTCGGTAGGTCCGACTATGCTTTTGAGGGTCTTAAACGAGGTCCC b     R  P  D  Y  Q  E  P  S  R  L  I  R  K  L  P  E  F  A  P  G   -

GAGGAGGAGTCAGGCTGCAGCGGTGTTGTGAAGCCAGTCCAGCCCAGTGGCCCTGAGGGG
1862 ------+------+------+------+------+------+- 1921
     CTCCTCCTCAGTCCGACGTCGCCACAACACTTCGGTCAGGTCGGGTCACCGGGACTCCCC b     E  E  E  S  G  C  S  G  V  V  K  P  V  Q  P  S  G  P  E  G   -

GTGCCCCACTATGCAGAGGCTGACATAGTGAACCTCCAAGGAGTGACAGGAGGCAACACA
1922 ------+------+------+------+------+------+- 1981
     CACGGGGTGATACGTCTCCGACTGTATCACTTGGAGGTTCCTCACTGTCCTCCGTTGTGT b     V  P  H  Y  A  E  A  D  I  V  K  L  Q  G  V  T  G  G  N  T   -

TACTCAGTGCCTGCCGTCACCATGGACCTGCTCTCAGGAAAAGATGTGGCTGTGGAGGAG
1982 ------+------+------+------+------+------+- 2041
     ATGAGTCACGGACGGCAGTGGTACCTGGACGAGAGTCCTTTTCTACACCGACACCTCCTC b     Y  S  V  P  A  V  T  M  D  L  L  S  G  K  D  V  A  V  E  E   -

TTCCCCAGGAAACTCCTAACTTTCAAAGAGAAGCTGGGAGAAGGACAGTTTGGGGAGGTT
2042 ------+------+------+------+------+------+- 2101
     AAGGGGTCCTTTGAGGATTGAAAGTTTCTCTTCGACCCTCTTCCTGTCAAACCCCTCCAA b     F  P  R  K  L  L  T  F  K  E  K  L  G  E  G  Q  F  G  E  V   -

CATCTCTGTGAAGTGGAGGGAATGGAAAAAATTCAAAGACAAAGATTTTGCCCTAGATGTC
2102 ------+------+------+------+------+------+- 2161
     GTAGAGACACTTCACCTCCCTTACCTTTTTAAGTTTCTGTTTCTAAAACGGGATCTACAG b     H  L  C  E  V  E  G  M  E  K  F  K  D  K  D  F  A  L  D  V   -

AGTGCCAACCAGCCTGTCCTGGTGGCTGTGAAAATGCTCCGAGCAGATGCCAACAAGAAT
2162 ------+------+------+------+------+------+- 2221
     TCACGGTTGGTCGGACAGGACCACCGACACTTCTACGAGGCTCGTCTACGGTTGTTCTTA b     S  A  N  Q  P  V  L  V  A  V  K  M  L  R  A  D  A  N  K  N   -
```

FIG.3E

```
       GCCAGGAATGATTTTCTTAAGGAGATAAAGATCATGTCTCGGCTCAAGGACCCAAACATC
2222   ------+---------+---------+---------+---------+---------+-  2281
       CGGTCCTTACTAAAAGAATTCCTCTATTTCTAGTACAGAGCCGAGTTCCTGGGTTTGTAG
``` b   A  R  N  D  F  L  K  E  I  K  I  M  S  R  L  K  D  P  N  I   -

```
       ATCCATCTATTAGCTGTGTGTATCACTGATGACCCTCTCTGTATGATCACTGAATACATG
2282   ------+---------+---------+---------+---------+---------+-  2341
       TAGGTAGATAATCGACACACATAGTGACTACTGGGAGAGACATACTAGTGACTTATGTAC
``` b   I  H  L  L  A  V  C  I  T  D  D  P  L  C  M  I  T  E  Y  M   -

```
       GAGAATGGAGATCTCAATCAGTTTCTTTCCCGCCACGAGCCCCCTAATTCTTCCTCCAGC
2342   ------+---------+---------+---------+---------+---------+-  2401
       CTCTTACCTCTAGAGTTAGTCAAAGAAAGGGCGGTGCTCGGGGGATTAAGAAGGAGGTCG
```

E  N  G  D  L  N  Q  F  L  S  R  H  E  P  P  N  S  S  S   -

```
       GATGTACGCACTGTCAGTTACACCAATCTGAAGTTTATGGCTACCCAAATTGCCTCTGGC
2402   ------+---------+---------+---------+---------+---------+-  2461
       CTACATGCGTGACAGTCAATGTGGTTAGACTTCAAATACCGATGGGTTTAACGGAGACCG
``` b   D  V  R  T  V  S  Y  T  N  L  K  F  M  A  T  Q  I  A  S  G   -

```
       ATGAAGTACCTTTCCTCTCTTAATTTTGTTCACCGAGATCTGGCCACACGAAACTGTTTA
2462   ------+---------+---------+---------+---------+---------+-  2521
       TACTTCATGGAAAGGAGAGAATTAAAACAAGTGGCTCTAGACCGGTGTGCTTTGACAAAT
``` b   M  K  Y  L  S  S  L  N  F  V  H  R  D  L  A  T  R  N  C  L   -

```
       GTGGGTAAGAACTACACAATCAAGATAGCTGACTTTGGAATGAGCAGGAACCTGTACAGT
2522   ------+---------+---------+---------+---------+---------+-  2581
       CACCCATTCTTGATGTGTTAGTTCTATCGACTGAAACCTTACTCGTCCTTGGACATGTCA
``` b   V  G  K  N  Y  T  I  K  I  A  D  F  G  M  S  R  N  L  Y  S   -

```
       GGTGACTATTACCGGATCCAGGGCCGGGCAGTGCTCCCTATCCGCTGGATGTCTTGGGAG
2582   ------+---------+---------+---------+---------+---------+-  2641
       CCACTGATAATGGCCTAGGTCCCGGCCCGTCACGAGGGATAGGCGACCTACAGAACCCTC
``` b   G  D  Y  Y  R  I  Q  G  R  A  V  L  P  I  R  W  M  S  W  E   -

FIG.3F

```
            AGTATCTTGCTGGGCAAGTTCACTACAGCAAGTGATGTGTGGGCCTTTGGGGTTACTTTG
    2642    ------+---------+---------+---------+---------+---------+--  2701
            TCATAGAACGACCCGTTCAAGTGATGTCGTTCACTACACACCCGGAAACCCCAATGAAAC b            S  I  L  L  G  K  F  T  T  A  S  D  V  W  A  F  G  V  T  L    -

TGGGAGACTTTCACCTTTTGTCAAGAACAGCCCTATTCCCAGCTGTCAGATGAACAGGTT
    2702    ------+---------+---------+---------+---------+---------+--  2761
            ACCCTCTGAAAGTGGAAAACAGTTCTTGTCGGGATAAGGGTCGACAGTCTACTTGTCCAA b            W  E  T  F  T  F  C  Q  E  Q  P  Y  S  Q  L  S  D  E  Q  V    -

ATTGAGAATACTGGAGAGTTCTTCCGAGACCAAGGGAGGCAGACTTACCTCCCTCAACCA
    2762    ------+---------+---------+---------+---------+---------+--  2821
            TAACTCTTATGACCTCTCAAGAAGGCTCTGGTTCCCTCCGTCTGAATGGAGGGAGTTGGT b            I  E  K  T  G  E  F  F  R  D  Q  G  R  Q  T  Y  L  P  Q  P    -

GCCATTTGTCCTGACTCTGTGTATAAGCTGATGCTCAGCTGCTGGAGAAGAGATACGAAG
    2822    ------+---------+---------+---------+---------+---------+--  2881
            CGGTAAACAGGACTGAGACACATATTCGACTACGAGTCGACGACCTCTTCTCTATGCTTC b            A  I  C  P  D  S  V  Y  K  L  M  L  S  C  W  R  R  D  T  K    -

AACCGTCCCTCATTCCAAGAAATCCACCTTCTGCTCCTTCAACAAGGCGACGAGTGATGC
    2882    ------+---------+---------+---------+---------+---------+--  2941
            TTGGCAGGGAGTAAGGTTCTTTAGGTGGAAGACGAGGAAGTTGTTCCGCTGCTCACTACG b            N  R  P  S  F  Q  E  I  H  L  L  L  Q  Q  G  D  E              -

TGTCAGTGCCTGGCCATGTTCCTACGGCTCAGGTCCTCCCTACAAGACCTACCACTCACC
    2942    ------+---------+---------+---------+---------+---------+--  3001
            ACAGTCACGGACCGGTACAAGGATGCCGAGTCCAGGAGGGATGTTCTGGATGGTGAGTGG b                                                                          -

CATGCCTATGCCACTCCATCTGGACATTTAATGAAACTGAGAGACAGAGGCTTGTTTGCT
    3002    ------+---------+---------+---------+---------+---------+--  3061
            GTACGGATACGGTGAGGTAGACCTGTAAATTACTTTGACTCTCTGTCTCCGAACAAACGA
```

FIG.3G

```
b                                                                              -

TTGCCCTCTTTTCCTGGTCACCCCCACTCCCTACCCCTGACTCATATATACTTTTTTTT
3062 ————————+————————+————————+————————+————————+————————+— 3121
     AACGGGAGAAAAGGACCAGTGGGGGTGAGGGATGGGGACTGAGTATATATGAAAAAAAAA b

TTACATTAAAGAACTAAAAAAAAAAAAAAAAAAAGGCG
3122 ————————+————————+————————+————————— 3158
     AATGTAATTTCTTGATTTTTTTTTTTTTTTTTTTCCGC b                                                                              -
```

FIG. 3H

```
CCK-2    MILIPRMLLVLFLLLPILSSA...KAQVNPAI CRYPLGMSGGQIPDEDIT    47
         : |   |  |:|||  : |:.    |:::.|| |||:|||  :  |||.||.
MCK-10   ..MGPEALSSLLLLLLVASGDADMKGHPDPAK CRYALGMQDRTIPDSDIS    48

CCK-2    ASSQWSESTAAKYGRLDSEEGDGAWCPEIPVEPDDLKEFLQIDLHTLHFI    97
         |||  ||:|||||:.:||:|.|:||||||.  .| |.:  .|:||:||: ||::
MCK-10   ASSSWSDSTAARHSRLESSDGDGAWCPAGSVPPKE.EEYLQVDLQRLHLV    97

CCK-2    TLVGTQGRHAGGHGIEFAPMYKINYSRDGTRWISWRNRHGKQVLDGNSNP    147
         .||||||||||  | ||..  |:::.|||||  ||::|:::|  |..:|..||.:|
MCK-10   ALVGTQGRHAGGLGKEFSRSYRLRYSRDGRRWMGWKDRWGQEVISGNEDP    147

CCK-2    YDIFLKDLEPPIVARFVRFIPVTDHSMNVCMRVELYGQVWLDGLVSYNAP    197
         :::.||||:||:|||:|||.|  .|:  |.||:|||||||||:|  |||:||.||
MCK-10   EGVVLKDLGPPMVARLVRFYPRADRVMSVCLRVELYGQLWRDGLLSYTAP    197

CCK-2    AGQQFVLPGGSIIYLNDSVYDG.AVGYSMTEGLGQLTDGVSGLDDFTQTH    246
         .||  :  |.::  :||||||.|||  .||  :||||.|||  |||||  ...:
MCK-10   VGQTMYLSEA..VYLNDSTYDGHTVGGLQYGGLGQLADGVVGLDDFRKSQ    245

CCK-2    EYHVWPGYDYVGWRNESATNGYIEIMFEFDRIRNFTTMKVHCNNMFAKGV    296
         |.:|||||||||||.|.|  ..||:|:  |||||:|.|  .|.|||||| . |.
MCK-10   ELRVWPGYDYVGWSNHSFSSGYVEMEFEFDRLRAFQAMQVHCNNMHTLGA    295

CCK-2    KIFKEVQC.YFRSEASEWEPNAISFPLVLDDVNPSARFVTVPLHHRMASA    345
         ::  :|:|  :  |:.|  .||.::::.  |. : .:|.|| |.|||  |:|.
MCK-10   RLPGGVECRFRRGPAMAWEGEPMRHNLGGNLGDPRARAVSVPLGGRVARF    345

CCK-2    IKCQYHFADTWMMFSEITFQSDAAMYNNSEALPTS.................    380
         :..|.: ||:.|:::||||.| || ..: |.|.|.|...
MCK-10   LQCRFLFAGPWLLFSEISFISD.VVNNSSPALGGTFPPAPWWPPGPPPTN    394

CCK-2    ....PMAPTTYDPMLKVDDSNTRILIGCLVAIIFILLAIIVIILWRQFWQ    426
         .:.| . :|:  |.::| | |||||||||::||  ||..:||| |.
MCK-10   FSSLELEPRGQQPVAKAEGSPTAILIGCLVAIILLLLLIIALMLWRLHWR    444

CCK-2    KMLEKASRRMLDDEMTVSLSLPSDSSMFNNRSSSPSEQGSNSTYDRIFP    476
         ::|.||.||:|::|:|| ||:|:|.  .::||..........
MCK-10   RLLSKAERRVLEEELTVHLSVPGDTILINNRPGPREP............    481
```

FIG.4A

```
CCK-2    LRPDYQEPSRLIRKLPEFAPGEEESGCSG........VVKPVQPSGPEGV   518
         |.||||..  .. .. :...:|::||         ... :.|....::|
MCK-10   ..PPYQEPRPRGNPPHSAPCVPNGSAYSGDYMEPEKPGAPLLPPPPQNSV   529
                                 ↑△   △

CCK-2    PHYAEADIVNLQGVTGGNTYSVPAVTMDLLSGKDVAVEEFPRKLLTFKEK   568
         |||||||||.|||||||||.|||:. : ::: .. | :|||.| ||||
MCK-10   PHYAEADIVTLQGVTGGNTYAVPALPPGAVGDGPPRV.DFPRSRLRFKEK   578
         * * *

CCK-2    LGEGQFGEVHLCEVEGMEKFKDKDFALDVSANQPVLVAVKMLRADANKNA   618
         ||||||||||||||:: :.:  . ||:|:|.  .:|||||:||:||.|||
MCK-10   LGEGQFGEVHLCEVDSPQDLVSLDFPLNVRKGHPLLVAVKILRPDATKNA   628
                                                        ↑

CCK-2    RNDFLKEIKIMSRLKDPNIIHLLAVCITDDPLCMITEYMENGDLNQFLSR   668
         |||||||:|||||||||||:||:||: ||||||||:||||||||||||||
MCK-10   RNDFLKEVKIMSRLKDPNIIRLLGVCVQDDPLCMITDYMENGDLNQFLSA   678

CCK-2    HE.........PPNSSSSDVRTVSYTNLKFMATQIASGMKYLSSLNFVHR   709
         |:         |..::  ....|:||. |  :|.||||||:||..|||||
MCK-10   HQLEDKAAEGAPGDGQAAQGPTISYPMLLHVAAQIASGMRYLATLNFVHR   728

CCK-2    DLATRNCLVGKNYTIKIADFGMSRNLYSGDYYRIQGRAVLPIRWMSWESI   759
         ||||||||||.|:|||||||||||||||.||||:||||||||||||.||:
MCK-10   DLATRNCLVGENFTIKIADFGMSRNLYAGDYYRVQGRAVLPIRWMAWECI   778
                                 △  △△

CCK-2    LLGKFTTASDVWAFGVTLWETFTFCQEQPYSQLSDEQVIENTGEFFRDQG   809
         |:|||||||||||||||||||.: :|..||::||.||||||.||||||||
MCK-10   LMGKFTTASDVWAFGVTLWEVLMLCRAQPFGQLTDEQVIENAGEFFRDQG   828

CCK-2    RQTYLPQPAICPDSVYKLMLSCWRRDTKNRPSFQEIHLLLLQQGDE..    855
         ||.||..|: ||:::|.|||.||.|:...||.| ::| :| :::  :
MCK-10   RQVYLSRPPACPQGLYELMLRCWSRESEQRPPFSQLHRFLAEDALNTV   876
           △       △
```

FIG.4B

| | | | |
|---|---|---|---|
| h MCK-10b | 524 | PRGPGPPTPAW | 534 |
| h ack | 795 | PRVPIPPRPTR | 805 |
| h Fak | 698 | APPKKPPRPGA | 708 |
| v-Fgr | 130 | RPRPLPPLPPT | 140 |
| m3BP1 | 267 | PTMPPPLPPVP | 277 |
| m3BP2 | 200 | PAYPPPPVPVP | 210 |
| h dynamin | 785 | APAVPPARPGS | 795 |
| h dynamin | 811 | GAPPVPSRPGA | 821 |
| h PI3K P85 | 91 | PPRPLPVAPGS | 101 |
| h PI3K P85 | 303 | PAPALPPKPPK | 313 |
| h CDC42 | 250 | APKPMPPRPPL | 260 |
| h mAChR (HM3) | 277 | PALPPPPRPVA | 287 |
| CONSENSUS | | Xp*PpXP | |

FIG.4D

RECOMBINANT DNA ENCODING CCK 2, A RECEPTOR TYROSINE KINASE

This is a continuation-in-part of co-pending U.S. application Ser. No. 08/153,397, filed Nov. 16, 1993 which is incorporated by reference herein in its entirety.

TABLE OF CONTENTS
1. INTRODUCTION
2. BACKGROUND
3. SUMMARY OF THE INVENTION
4. BRIEF DESCRIPTION OF THE FIGURES
5. DETAILED DESCRIPTION
    5.1. The MCK-10 Coding Sequence
    5.2. The CCK-2 Coding Sequence
    5.3. Expression of MCK-10 Receptor and Generation of Cell Lines that Express MCK-10
        5.3.1. Expression Systems
        5.3.2. Identification of Transfectants or Transformants that Express the MCK-10
    5.4. Uses of the MCK-10 Receptor and Engineered Cell Lines
        5.4.1. Screening of Peptide Library with MCK-10 Protein or Engineered Cell Lines
        5.4.2. Antibody Production and Screening
    5.5. Uses of MCK-10 Coding Sequence
        5.5.1. Use of MCK-10 Coding Sequence in Diagnostics and Therapeutics
        5.5.2. Use of Dominant Negative MCK-10 Mutants in Gene Therapy
6. EXAMPLES: CLONING AND CHARACTERIZATION OF MCK-10
    6.1. Materials and Methods
        6.1.1. cDNA Cloning and Characterization of MCK-10
        6.1.2. Full-Length cDNA Cloning
        6.1.3 Northern Blot Analysis of MCK-10
        6.1.4. Generation of MCK-10 Specific Antibodies
        6.1.5. In Situ Hybridization
    6.2. Results
        6.2.1. Characterization of MCK-10 Clone
        6.2.2. Northern Blot Analysis: Expression of MCK-10 in Various Human Tissues and Cell Lines
        6.2.3. In Situ Hybridization
        6.2.4. Transient Expression of MCK-10 in 293 Cells
7. EXAMPLES: CLONING AND CHARACTERIZATION OF CCK-2
    7.1. Materials and Methods
        7.1.1. cDNA Cloning and Characterization of CCK-2
        7.1.2. Northern Blot Analysis
        7.1.3. In Situ Hybridization
        7.1.4. Transient Overexpression of CCK-2 in 293 Cells
    7.2. Results
        7.2.1. Characterization of CCK-2 Clone
        7.2.2. Northern Blot Analysis: Expression of CCK-2 in Various Human Tissues and Cell Lines
        7.2.3. In Situ Hybridization
        7.2.4. Transient Expression of CCK-2 in 293 Cells
8. DEPOSIT OF MICROORGANISMS

1. INTRODUCTION

The present invention relates to the novel family of receptor tyrosine kinases, herein referred to as MCK-10, to nucleotide sequences and expression vectors encoding MCK-10, and to methods of inhibiting MCK-10 activity. The invention relates to differentially spliced isoforms of MCK-10 and to other members of the MCK-10 receptor tyrosine kinase family such as CCK-2. Genetically engineered host cells that express MCK-10 may be used to evaluate and screen drugs involved in MCK-10 activation and regulation. The invention relates to the use of such drugs for modulating the activity of MCK-10. Such drugs may be used in the treatment of proliferative disorders such as cancers and in the treatment of nervous system disorders.

2. BACKGROUND

Receptor tyrosine kinases comprise a large family of transmembrane receptors which are comprised of an extracellular ligand-binding domain and an intracellular tyrosine-kinase domain responsible for mediating receptor activity. The receptor tyrosine kinases are involved in a variety of normal cellular responses which include proliferation, alterations in gene expression, and changes in cell shape.

The binding of ligand to its cognate receptor induces the formation of receptor dimers leading to activation of receptor kinase activity. The activation of kinase activity results in phosphorylation of multiple cellular substrates involved in the cascade of events leading to cellular responses such as cell proliferation.

Genetic alterations in growth factor mediated signalling pathways have been linked to a number of different diseases, including human cancer. For example, the normal homologs of many oncogenes have been found to encode growth factors or growth factor receptors. This is illustrated by the discovery that the B chain of human PDGF is homologous to the transforming protein of simian sarcoma virus (SSV), the EGF (epidermal growth factor) receptor to erb B; the CSF (colony stimulating factor) receptor to fms; and the NGF (nerve growth factor) receptor to T2k. In addition, growth factor receptors are often found amplified and/or overexpressed in cancer cells as exemplified by the observation that the EGF receptor is often found amplified or overexpressed in squamous cell carcinomas and glioblastomas. Similarly, amplification and overexpression of the met gene, encoding the HGF receptor, has been detected in stomach carcinomas.

Recently, a number of cDNAs have been identified that encode receptor tyrosine kinases. One such clone, referred to as DDR (discoidin domain receptor), was isolated from a breast carcinoma cDNA library (Johnson et al., 1993, Proc. Natl. Acad. Sci. USA, 90, 5677–5681) and is homologous to MCK-10. In addition, a mouse homologue of MCK-10 has recently been cloned and characterized (Zerlin, M. et al., 1993, Oncogene, 8: 2731–2739).

The discovery of novel receptor tyrosine kinase receptors, whose expression is associated with proliferative diseases such as cancer, will provide opportunities for development of novel diagnostic reagents. In addition, the identification of aberrantly expressed receptor tyrosine kinases will lead to the development of therapeutic applications designed to inhibit the activity of that receptor, which may be useful for treatment of proliferative diseases such as cancer.

3. SUMMARY OF THE INVENTION

The present invention relates to a novel family of receptor tyrosine kinases, herein referred to as MCK-10 (mammary carcinoma kinase 10), to nucleotide sequences and expression vectors encoding MCK-10, and to methods of inhibiting MCK-10 activity. The invention is based on the isolation of cDNA clones from a human mammary carcinoma cDNA library encoding the MCK-10 receptor tyrosine kinase.

The invention also relates to differentially spliced isoforms of MCK-10 and to other members of the MCK-10 family of receptor tyrosine kinases. More specifically, the invention relates to members of the MCK-10 family of receptors tyrosine kinases that are defined, herein, as those receptors demonstrating 80% homology at the amino acid level in substantial stretches of DNA sequences with MCK-10. In addition, members of the MCK-10 family of tyrosine kinase receptors are defined as those receptors containing an intracellular tyrosine kinase domain and consensus sequences near the extracellular N-terminus of the protein for the discoidin I like family of proteins. The invention as it relates to the members of the MCK-10 family of receptor tyrosine kinases, is based on the isolation and characterization of a cDNA, herein referred to as CCK-2, encoding a member of the MCK-10 family of receptor tyrosine kinases.

Northern Blot analysis indicates that MCK-10 is expressed in a variety of normal tissues including brain tissue. In addition, the MCK-10 family of receptors share homology with the TrK neurotropin tyrosine kinase receptor, indicating that MCK-10 agonists and/or antagonists can be useful for treatment of nervous system disorders.

Additionally, Northern blot analysis and in situ hybridization indicates that MCK-10 and CCK-2 are expressed in a wide variety of cancer cell lines and tumor tissue. Therefore, the present invention relates to inhibitors of MCK-10 or CCK-2 receptor activity which may have therapeutic value in the treatment of proliferative diseases such as cancer.

Modulators of MCK-10 or CCK-2 receptor kinase activity may include antibodies to epitopes of recombinantly expressed MCK-10 or CCK-2 receptor which may regulate the activity of the receptor. In another embodiment of the invention, MCK-10 or CCK-2 anti-sense oligonucleotides may be designed to inhibit synthesis of the encoded proteins through inhibition of translation. In addition, random peptide libraries may be screened using recombinantly produced MCK-10 or CCK-2 protein to identify peptides, synthetic compounds, and natural products that may act as agonists and/or antagonists of the biological activity of the receptors through binding to the ligand binding sites or other functional domains of the MCK-10 or CCK-2 receptor. In a further embodiment of the invention, mutated forms of MCK-10 and CCK-2, having a dominant negative effect, may be expressed in targeted cell populations to regulate the activity of the endogenously expressed receptors.

Furthermore, the MCK-10 or CCK-2 coding sequence may be used for diagnostic purposes for detection of aberrant expression of these genes. For example the MCK-10 or CCK-2 DNA sequence may be used in hybridization assays of biopsied tissue to diagnose abnormalities in gene expression.

4. BRIEF DESCRIPTION OF THE FIGURES

FIGS. 1A, 1B, 1C, 1D, 1E, 1F, and 1G. Human MCK-10-3 nucleotide sequence (SEQ ID NO:1) and deduced amino acid sequence (SEQ ID NO:2). Regions of interest include the signal sequence (amino acids (aa) 1–18); the Discoidin I-like domain (aa 31–185); the putative precursor cleavage site (aa 304–307); the transmembrane region (aa 418–439); the alternatively spliced sequence I (aa 505–541); the alternatively spliced sequence II (aa 666–671); and the peptide antibody recognition sequences: NTα:aa 26–42, NTβ:aa 309–321, CTβ:aa 902–919.

FIG. 2A. MCK-10 splice variants.

FIG. 2B. Alignment of MCK-10, MCK-10-2 and MCK-10-1 (SEQ ID NOS:15–18). The NPXY motif (SEQ ID NO:19) in the insertion region of the MCK-10-1 is underlined with thin and the putative SH3 binding site with solid bars. The TYAXPXXXPG sequence (SEQ ID NO:8) is overlined.

FIGS. 3A, 3B, 3C, 3D, 3E, 3F, 3G and 3H. Human CCK-2 nucleotide sequence (SEQ ID NO:3), complementary strand (SEQ ID NO:5), and deduced amino acid sequence (SEQ ID NO:4).

FIGS. 4A and 4B. Comparison of deduced CCK-2 and MCK-10-2 amino acid sequences. The discoidin I-like domain is boxed with consensus residues of the discoidin I motif shaded. N-linked glycosylation sites of CCK-2 are indicated with solid triangles, and tyrosine residues that are possible autophosphorylation and substrate attachment sites are marked by open triangles. The RXRR protease cleavage motif (SEQ ID NO:20) is underlined and the putative transmembrane region is overlined with a solid bar. Asterisks indicate the consensus residues of the ATP-binding site. Positions of MCK-10-1 and MCK-10-2 alternative splice insertions are indicated by arrows.

Figure 4C:
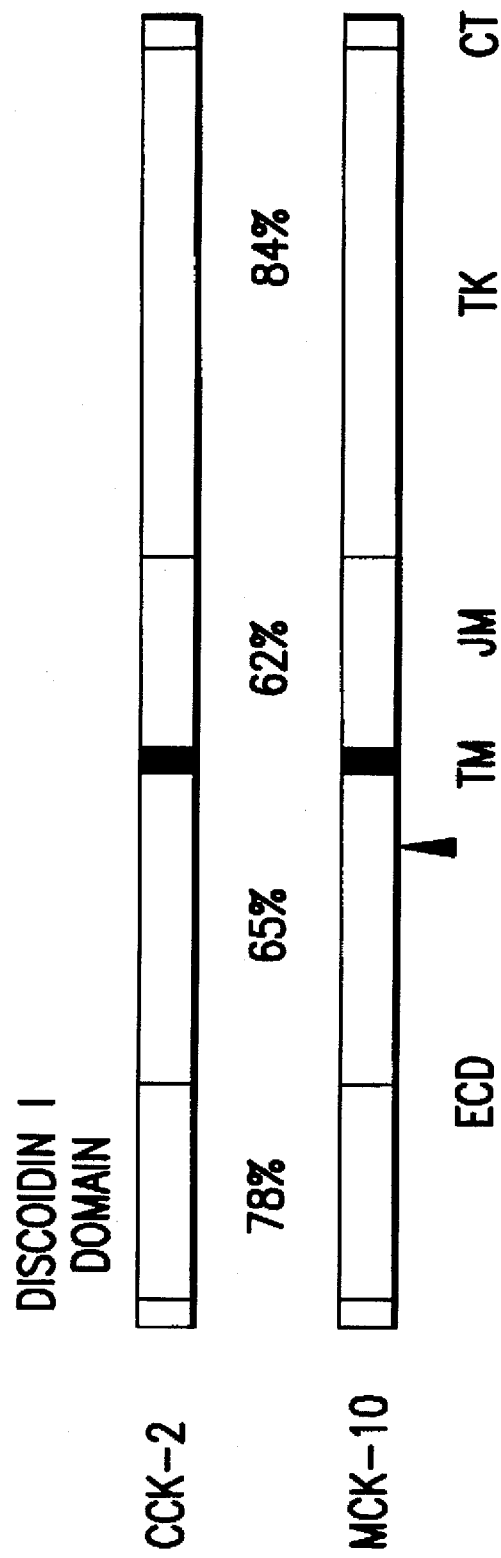

FIG. 4C. Schematic structures of CCK-2 and MCK-10. The percent amino acid identity between CCK-2 and MCK-10 is indicated for the discoidin I domain, part of the extracellular domain (ECD), the juxtamembrane domain (JM), and the tyrosine kinase region (TK). TM: transmembrane region. CT: carboxyl-terminal tail. The arrowhead indicates the location of the predicted protease cleavage site RXRR, which divides the MCK-10 protein into N-terminal α and C-terminal β fragments.

FIG. 4D. Putative SH3 domain binding site in MCK-10-1. Established and predicted SH3 binding sites of various proteins are compared (SEQ ID NO:21–33). X: non-conserved position. *: strong preference for hydrophobic residues. P: invariable position for proline. p: position with preference for proline.

Figure 5A:
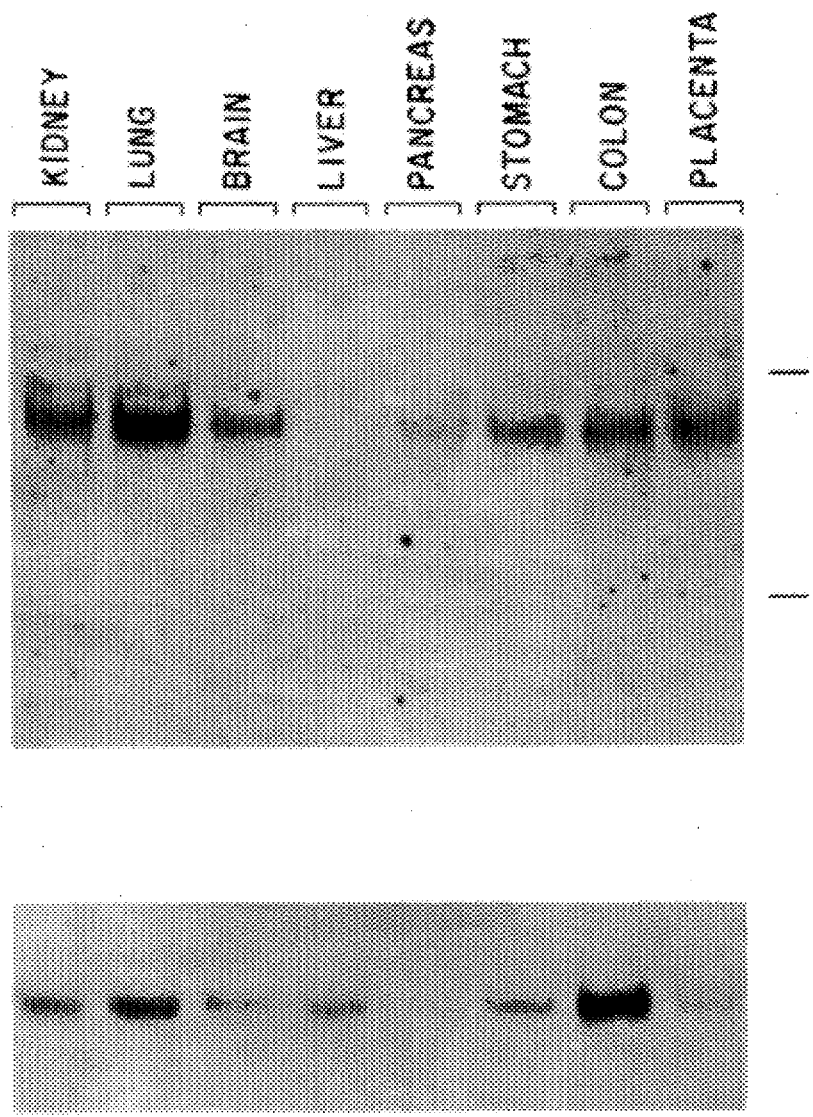

FIG. 5A. Northern blot analysis of MCK-10 mRNA in different human tissues. Three micrograms of poly $(A)^+$ RNA are loaded per lane. The blot is hybridized with a cDNA restriction fragment corresponding to nucleotide 278 to 1983 of MCK-10-2 (FIGS. 1A, 1B and 1C) (excluding the 111 bp insertion). As a control, the blot was rehybridized with a glyceraldehyde phosphate dehydrogenase (GAPDH) cDNA probe (lower panel).

Figure 5B:
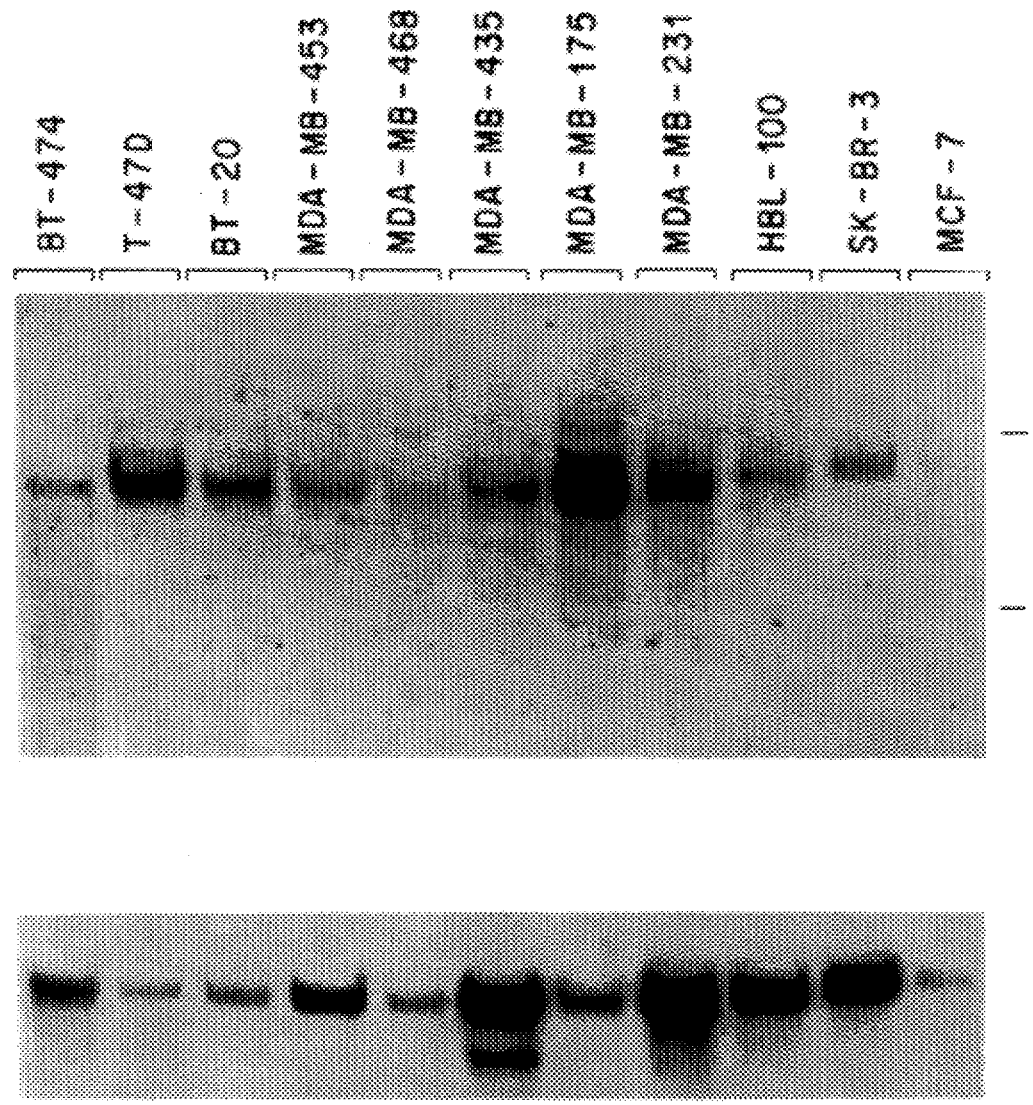

FIG. 5B. Northern blot analysis of MCK-10 gene in various human breast cancer cell lines. Samples containing three micrograms of poly $(A)^+$ RNA isolated from different human breast cancer cell lines were analyzed. The position of 28S and 18S ribosomal RNAs is indicated, the lower panel shows the rehybridization with a GAPDH cDNA probe.

Figure 5C:
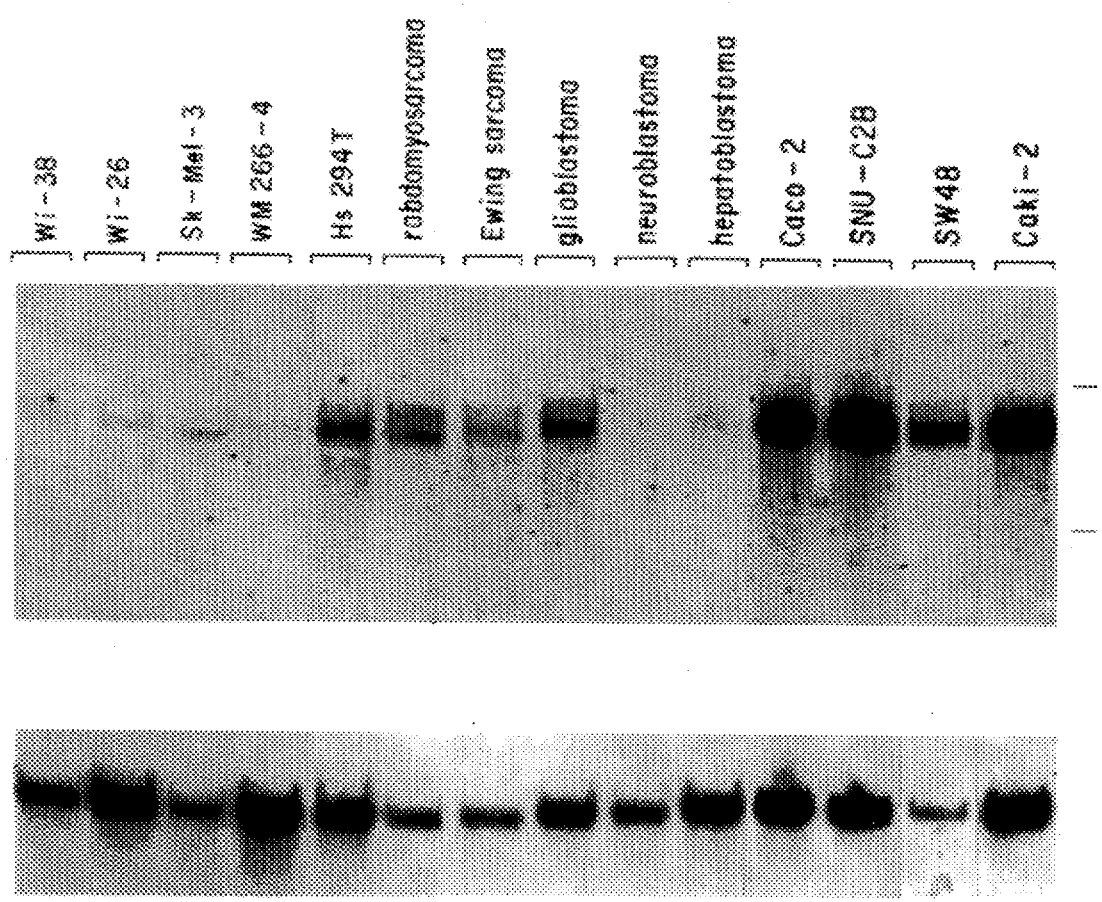

FIG. 5C. Northern blot analysis of MCK-10 mRNA in different human tissues and cell lines of tumor origin. Size markers are indicating 28S and 18S ribosomal RNAs (upper panel). Rehybridization is performed with a GAPDH cDNA probe (lower panel).

Figure 5D:
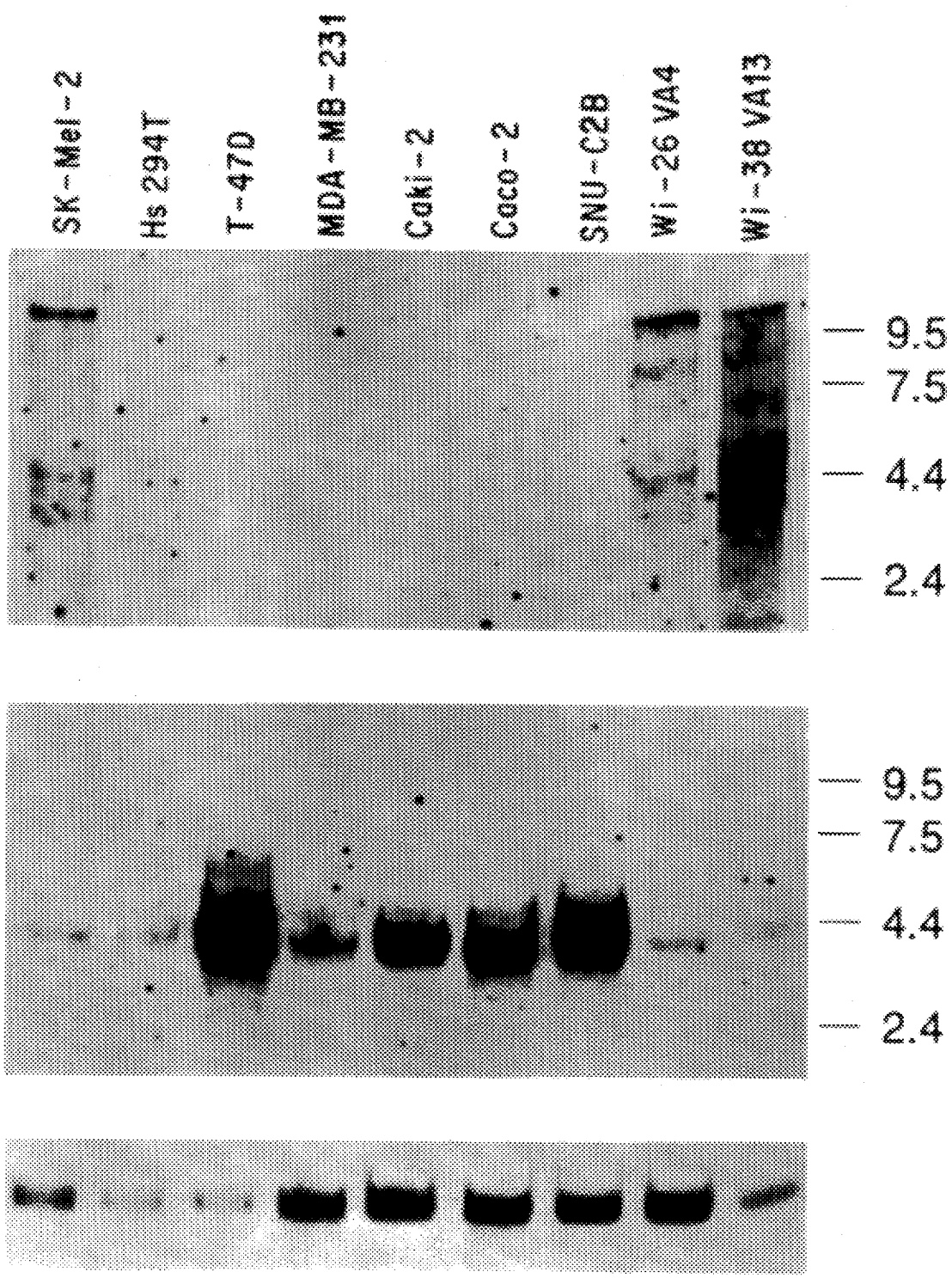

FIG. 5D. Northern blot analysis of CCK-2 and MCK-10 mRNA. Expression of CCK-2 and MCK-10 mRNA in different human carcinoma cell lines is shown. Three micrograms of poly $(A)^+$ RNA were loaded per lane. The blots were hybridized with a cDNA restriction fragment corresponding to the extracellular region of CCK-2 (upper panel) and MCK-10 (middle panel). RNA markers of sizes are indicated in kb. In order to calibrate relative quantities of loaded RNAs, the blots are rehybridized with a GAPDH cDNA probe (lower panel).

Figure 6A:
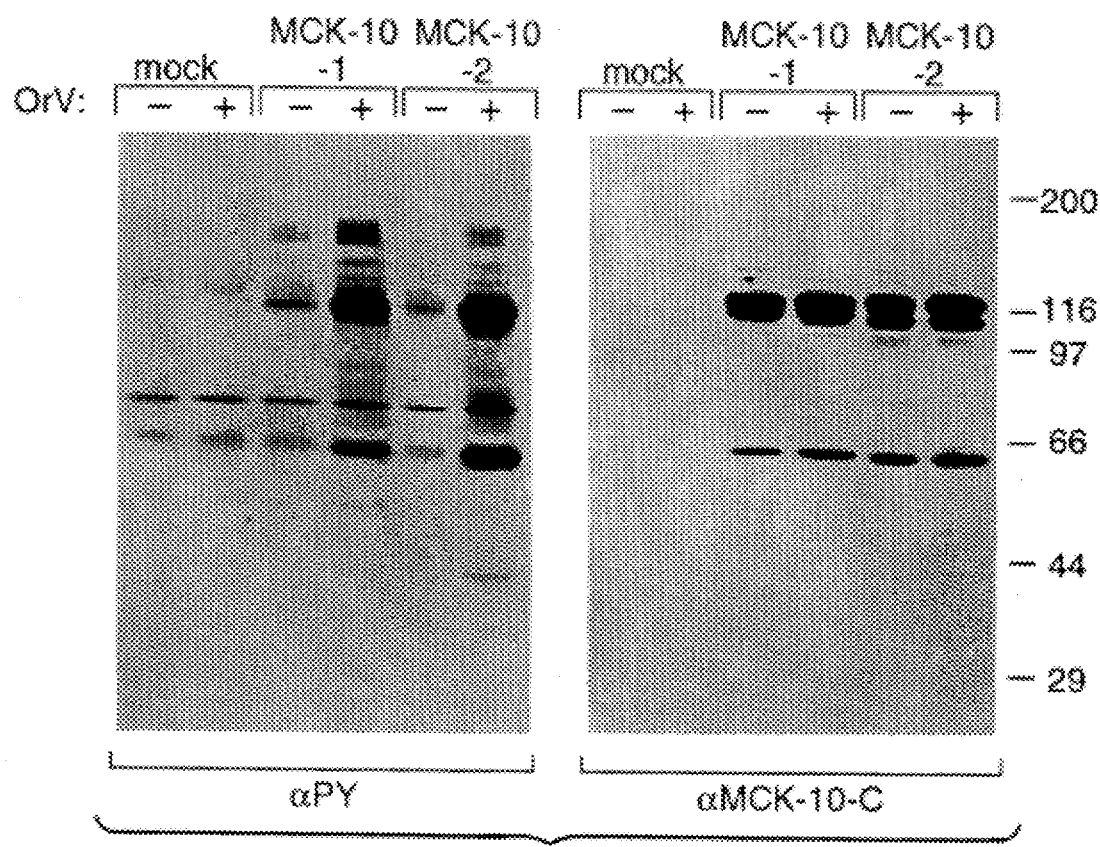

FIG. 6A. Tyrosine phosphorylation of overexpressed MCK-10. The coding cDNAs of MCK-10-1 and MCK-10-2 were cloned into an expression vector and transiently overexpressed in the 293 cell line (human embryonic kidney fibroblasts, ATCC CRL 1573). Portions of cell lysate from either MCK-10-1 or -2 transfected cells or control plasmid transfected cells (mock) were separated on a 10% polyacrylamide gel and transferred to nitrocellulose and probed with anti-phosphotyrosine antibodies (αPY). The incubation of cells with 1 mM sodium ortho-vanadate 90 min. prior to lysis is indicated by ±; (left panel). After removal of the αPY antibody the blot was reprobed with an affinity purified polyclonal antiserum raised against the C-terminal octapeptide of MCK-10 (α MCK-10-C); (right panel). Molecular size markers are indicated in kD.

Figure 6B:
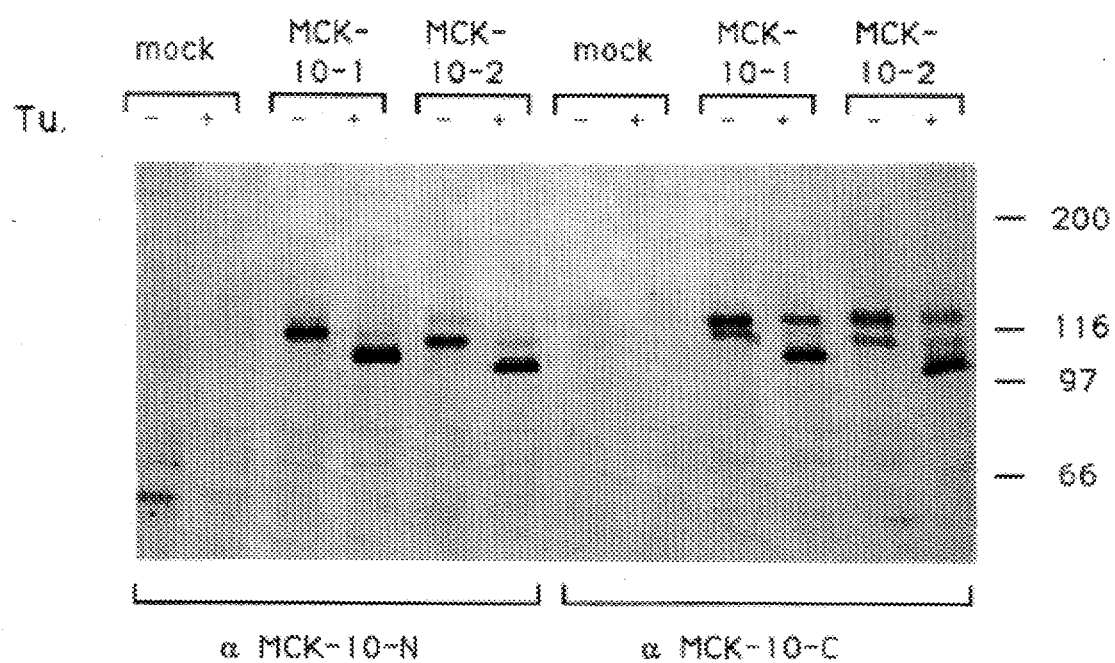

FIG. 6B. Distinct glycosylation of overexpressed MCK-10 splice variants. 293 cells were transfected with MCK-10-1 and -2 as before, metabolically labeled with $[^{35}S]$-L-methionine and treated with 10 μg/ml tunicamycin overnight as indicated (+), lysed and immunoprecipitated with antisera generated against the N-terminal and C-terminal peptides of MCK-10 (α MCK-10-N and α MCK-10-C). The autoradiograph of the SDS-PAGE analysis is shown. Molecular size markers are indicated in kD.

Figure 6C:
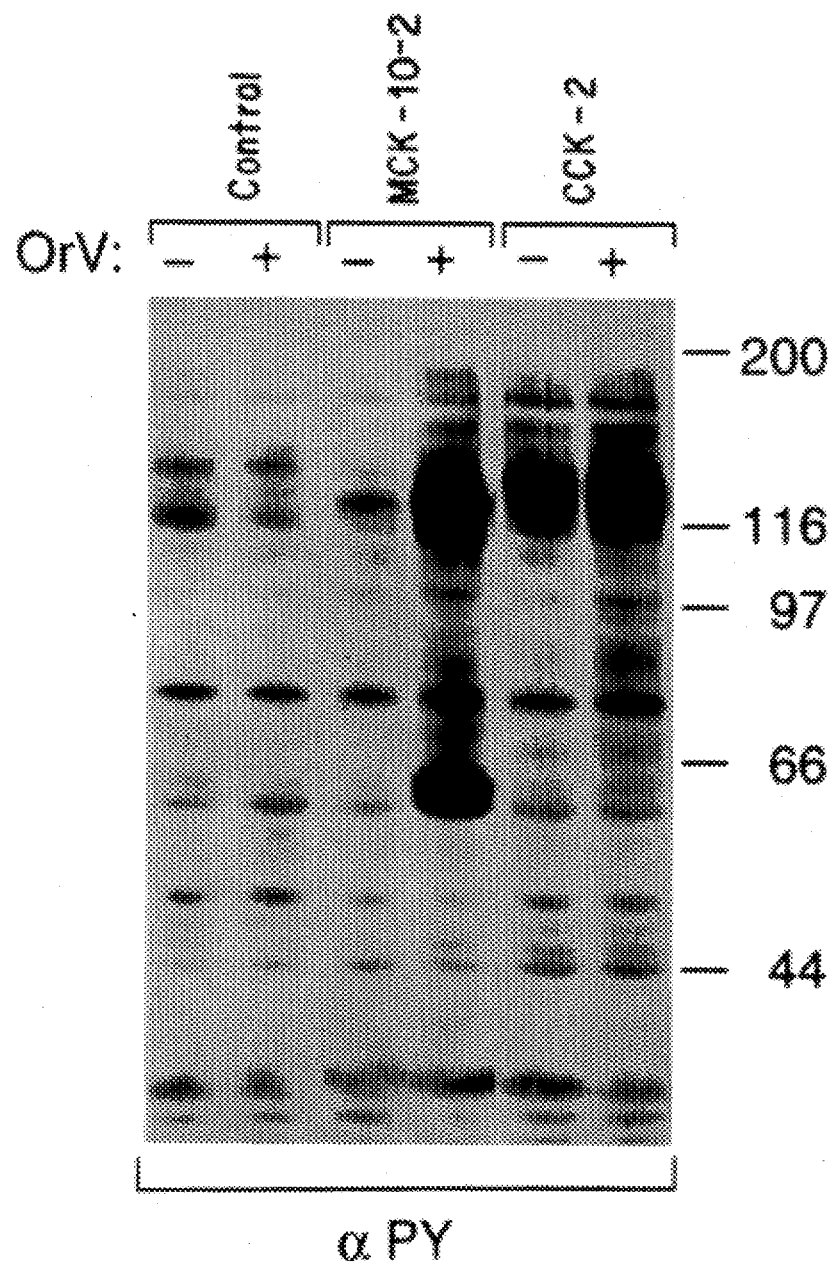

FIG. 6C. Transient overexpression of CCK-2 and MCK-10 receptor proteins. The coding MCK-10-2 and CCK-2 cDNA coding regions were cloned into a cytomegalovirus-based expression vector and transiently overexpressed in the human embryonic kidney fibroblast 293 cell line. Cell lysates from either MCK-10-2 or CCK-2-transfected cells or control plasmid-transfected cells were separated on a 7.5% polyacrylamide gel, transferred to nitrocellulose, and probed with antiphosphotyrosine antibody (αPY). Incubation of cells with 1 mM sodium orthovanadate 90 minutes prior to lysis is indicated by ±.

Figure 6D:
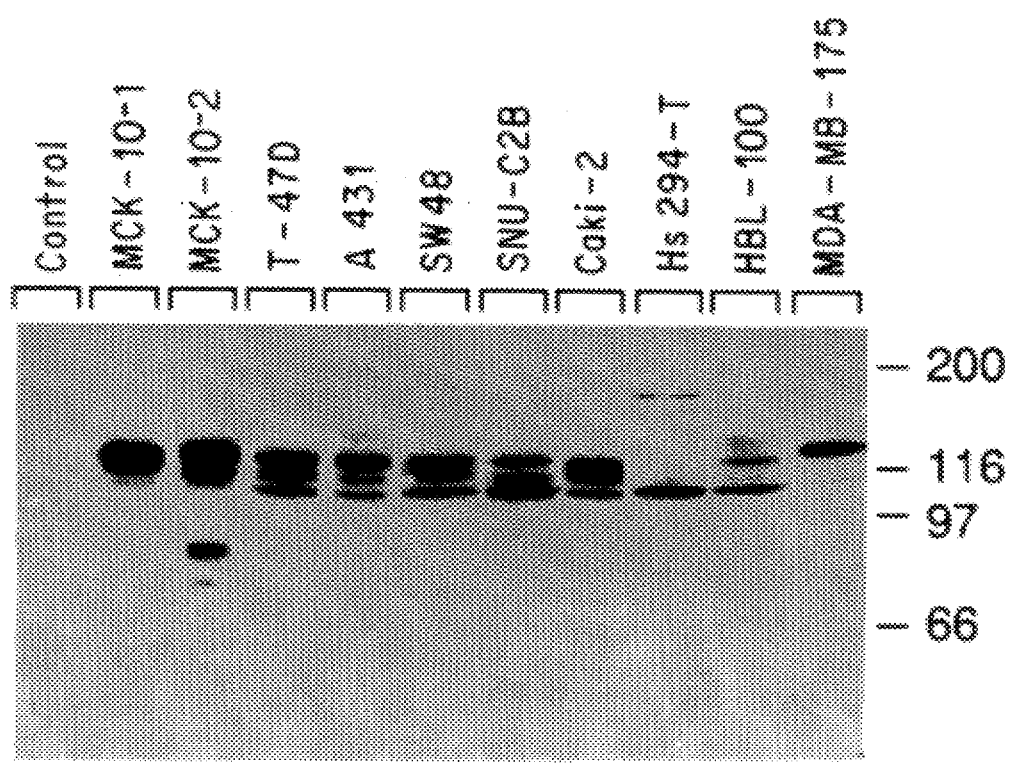

FIG. 6D. Identification of MCK-10 protein isoforms in human carcinoma cell lines. The glycoprotein fraction of equal amounts of cell lysates was bound to concanavalin-A-Sepharose and, after elution, separated by SDS-PAGE. The gel was blotted to nitrocellulose and probed with the polyclonal antibody αMCK-10-N. Lysates of MCK-10-1 and MCK-10-2 overexpressing 293 cells were used as controls. Molecular size markers are indicated in kDa.

Figure 7A:
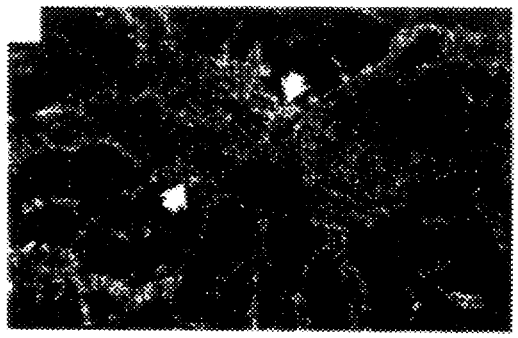
Figure 7B:
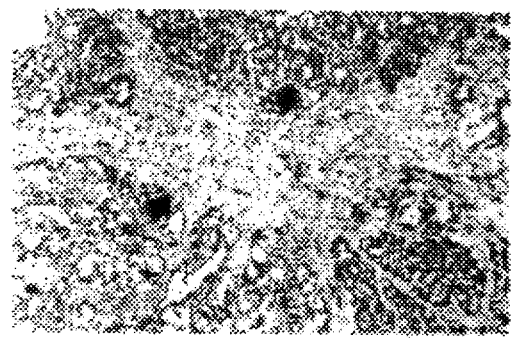
Figure 7C:
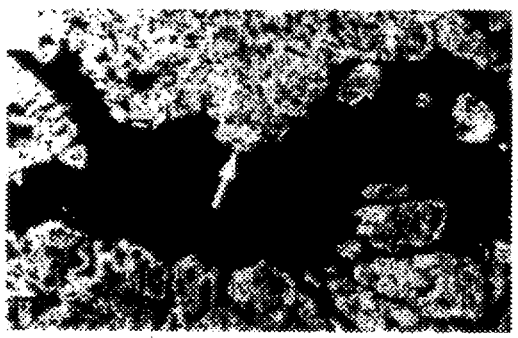
Figure 7D:
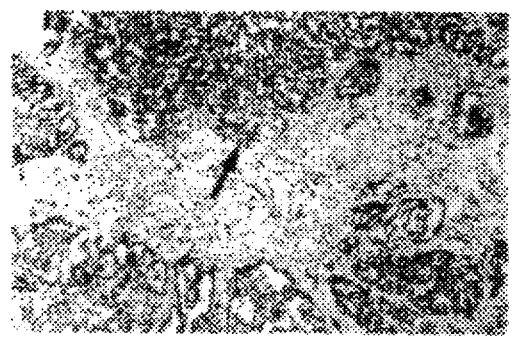
Figure 7E:
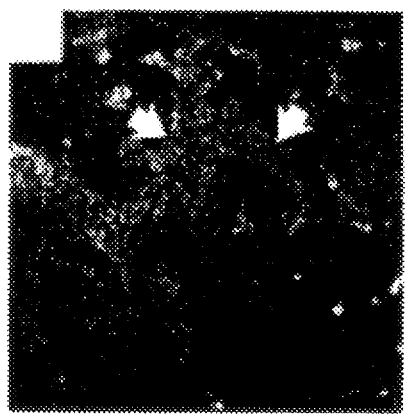
Figure 7F:
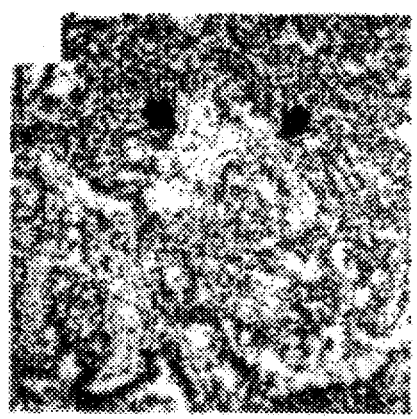
Figure 7G:
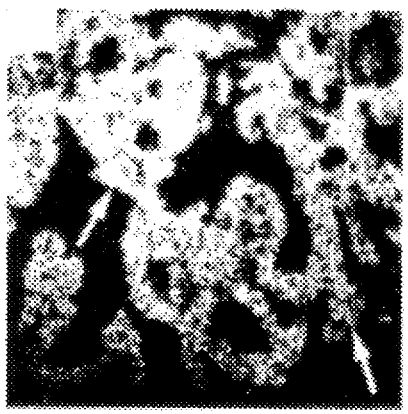
Figure 7H:
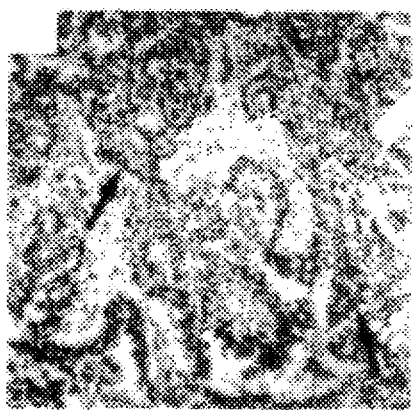

FIGS. 7A, 7B, 7C, 7D, 7E, 7F, 7G and 7H. CCK-2 and MCK-10 gene transcripts in sections of human adenocarcinomas. Adjacent sections of papillary adenocarcinoma of the ovary (FIGS. 7A–7D) and bronchioalveolar adenocarcinoma of the lung (FIGS. 7E–7H) were analyzed by in situ hybridization using antisense MCK-10 and CCK-2 probes. Tumor cells are indicated by long arrows (FIGS. 7C, 7D) infiltrating the connective tissue as indicated by short arrows (FIGS. 7A, 7B). As viewed in dark field, CCK-2 hybridization signals are seen specifically in cells of the connective tissue (FIGS. 7A, 7E), whereas MCK-10 expression is restricted to tumor cells (FIGS. 7C, 7G). FIGS. 7B, 7D, 7F, and 7H show bright-field illumination of respective adjacent sections.

5. DETAILED DESCRIPTION

The present invention relates to a novel family of receptor tyrosine kinases referred to herein as MCK-10. The invention relates to differentially spliced isoforms of MCK-10 and to additional members of the MCK-10 family of receptor tyrosine kinases such as the CCK-2 gene described herein. The invention is based, in part, on the isolation of a cDNA clone encoding the MCK-10 receptor tyrosine kinase and the discovery of differentially spliced isoforms of MCK-10. The invention also relates to the isolation of a cDNA encoding on additional member of MCK-10 receptor tyrosine kinase family, herein referred to as CCK-2.

Results from Northern Blot analysis and in situ hybridization indicates that MCK-10 is expressed in epithelial cells. In addition, MCK-10 expression can be detected in a wide variety of cancer cells lines and in all tested tumors. The invention relates to, expression and production of MCK-10 protein, as well as to inhibitors of MCK-10 receptor activity which may have therapeutic value in the treatment of diseases such as cancer.

Northern Blot analysis also indicates that MCK-10 is expressed in brain tissue. In addition, the MCK-10 gene product shares homology with the TrK neurotropin receptor tyrosine kinase. Therefore, the invention relates to modulators of MCK-10 activity that may be used for treatment of neurological disorders.

For clarity of discussion, the invention is described in the subsections below by way of example for the MCK-10 gene depicted in FIGS. 1A, 1B, 1C, 1D, 1E, 1F and 1G and the CCK-2 gene depicted in FIGS. 3A, 3B, 3C, 3D, 3E, 3F, 3G, and 3H However, the principles may be analogously applied to differentially spliced isoforms of MCK-10 and to other members of the MCK-10 family of receptors.

5.1. The MCK-10 Coding Sequence

The nucleotide coding sequence and deduced amino acid sequence of the human MCK-10 gene is depicted in FIGS. 1A, 1B, 1C, 1D, 1E, 1F and 1G (SEQ. ID NOS: 1–2). In accordance with the invention, any nucleotide sequence which encodes the amino acid sequence of the MCK-10 gene product can be used to generate recombinant molecules which direct the expression of MCK-10. In additional embodiments of the invention, nucleotide sequences which selectively hybridize to the MCK-10 nucleotide sequence shown in FIG. 1A, 1B, 1C, 1D, 1E, 1F and 1G (SEQ ID NO.: 1) may also be used to express gene products with MCK-10 activity. Hereinafter all such variants of the MCK-10 nucleotide sequence will be referred to as the MCK-10 DNA sequence.

In a specific embodiment described herein, the human MCK-10 gene was isolated by performing a polymerase chain reaction (PCR) in combination with two degenerate oligonucleotide primer pools that were designed on the basis of highly conserved sequences within the kinase domain of receptor tyrosine kinases corresponding to the amino acid sequence HRDLAA (SEQ ID NO:6) (sense primer) and SDVWS/FY (SEQ ID NO:7) (antisense primer) (Hanks et al., 1988). As a template cDNA synthesized by reverse transcription of poly-A RNA from the human mammary carcinoma cell line MCF7, was used. A novel RTK, designated MCK-10 (mammary carcinoma kinase 10) was identified that within the tyrosine kinase domain exhibited extensive sequence similarity to the insulin receptor family. The PCR fragment was used to screen a lambda gt11 library of human fetal brain cDNA (Clontech). Several overlapping clones were identified. The composite of these cDNA clones is depicted in FIGS. 1A, 1B, 1C, 1D, 1E, 1F and 1G. Furthermore, screening of a human placental library yielded two cDNA clones, MCK-10-1 and MCK-10-2, which encoded the entire MCK-10 protein but contained a shorter 5' untranslated region starting at position 278 of the MCK-10 sequence (FIGS. 1A, 1B, 1C, 1D, 1E, 1F and 1G). Sequences analysis of the two clones revealed complete identity with the exception of 111 additional nucleotides within the juxtamembrane domain, between nucleotides 1832 and 1943. One of the clones isolated from the human fetal brain library contained an additional 18 nucleotides in the tyrosine kinase domain. These sequences were in-frame with the MCK-10 open reading frame and did not contain any stop codons. The MCK-10 splice isoforms have been designated MCK-10-1 (with the additional 111 bp), MCK-10-2 (without any insertions), MCK-10-3 (with the additional 111 bp and 18 bp), and MCK-10-4 (with the additional 18 bp) (FIG. 2).

As shown in FIGS. 1A, 1B, 1C, 1D, 1E, 1F and 1G and FIGS. 3A, 3B, 3C, 3D, 3E, 3F, 3G and 3H, MCK-10 have all of the characteristics of a receptor PTK: the initiation codon is followed by a stretch of essentially hydrophobic amino acids, which may serve as a signal peptide. Amino acids 418–439 are also hydrophobic in nature, with the characteristics of a transmembrane region. The extracellular domain encompasses 4 consensus N-glycosylation sites (AsnXSer/Thr) and 7 cysteine residues. The extracellular region is shorter than that of the insulin receptor family and shows no homology to other receptor tyrosine kinases, but contains near the N-terminus an approximately 150 amino acid long region with remarkable homology to discoidin I, a lectin of the slime mold *Dictyostelium discoideum* (Poole et al. 1981, J. Mol. Biol. 153: 273–289; Alexander et al., 1992, Differentiation 51: 149–161). A role for this motif in cell-cell interaction is suggested by its previous identification in coagulation factors V and VIII, which mediate aggregation of platelets by binding to anionic lipids on the cell surface (Gilbert et al., 1991 J. Biol. Chem. 266: 17261–17268). Consistent with a role in cell-cell interaction, another factor sharing this motif, the Xenopus A5 protein, is involved in cell recognition during development of the amphibian nervous system (Takagi et al., 1991 Neuron 7: 295–307).

In addition, MCK-10 contains the consensus sequence RXRR (SEQ ID NO:20) at position 304–307, which represents a possible cleavage signal for the endopeptidase furin suggesting that MCK-10 is synthesized as a precursor polypeptide. The unglycosylated primary translation products of MCK-10-1 and MCK-10-2 proreceptors, with predicted molecular weights of 101.13 and 97.17 kD, respectively, can thus be subdivided into a 34.31 kD α subunit and 66.84 or 62.88 kD β-subunits that contain the tyrosine kinase homology and alternative splice sites.

The consensus sequence for an ATP-binding motif is located at positions 617–627 (FIGS. 1A, 1B and 1C). When compared with other kinases, the ATP binding domain is 176 amino acids (including the additional 37 amino acids) further from the transmembrane domain than any other tyrosine kinase. The additional 37 amino acids are located in the long and proline/glycine-rich juxtamembrane region (JM) and contain an NPAY sequence (where A can be exchanged for any amino acid), which is found in cytoplasmic domains of several cell surface proteins, including RTKs of the EGF and insulin receptor families (Chen et al. 1990, J. Biol. Chem., 265: 3116–3123). This consensus motif is followed by the sequence TYAXPXXXPG, (SEQ ID NO:8) which is repeated downstream in MCK-10 in the juxtamembrane domain at positions 585–595. Recently it has been shown that this motif is deleted in the cytoplasmic juxtamembrane region of the activin receptor, serine/threonine kinase, resulting in reduced ligand binding affinity (Attisano et al. 1992, Cell, 68: 97–108).

In comparison with other RTKs, the catalytic domain shows the highest homology to the TrkA receptor. The YY-motifs (position 802/803) and the tyrosine at position 798, representing putative autophosphorylation sites, characterize MCK-10 as a member of the insulin receptor family (FIGS. 1A, 1B and 1C). MCK-10 shares homology with the Trk neurotrophin receptor subfamily of receptor tyrosine kinase with their characteristic short carboxyl-terminal tail of 9 amino acids.

Several tyrosine residues in the kinase and JM domains of MCK-10-2 are flanked by consensus sequences that suggest a role as autophosphorylation and substrate attachment sites. The sequences flanking Tyr-844 in MCK-10 (YELM) (SEQ ID NO:34) in the COOH-terminal region of the kinase core domain contain the YXXM (SEQ ID NO:35) binding motif for association of the p85 subunit of phosphatidylinositol 3'-kinase (P13-kinase). Another potential substrate binding site is found 12 amino acids upstream at position Tyr 832 in MCK-10-2 (YLSR) (SEQ ID NO:36). Moreover, analogous to TrK, Tyr-506 (YSGD) (SEQ ID NO:37) in the JM region of MCK-10-2 could serve as a receptor binding site for SHC, an oncogenic SH2 domain-containing molecule (Obermeier et al. 1993, J. Biol. Chem. 268: 22963–22966), and sequences flanking Tyr 510 (YMEP) (SEQ ID NO:38) in MCK-10 qualify as the binding site for the GTPase-activating protein (GAP) because of similarity to the GAP binding site in the platelet-derived growth factor receptor (PDGF-R).

To characterize the receptor proteins encoded by MCK-10 cDNAs, the human embryonic kidney cell line 293 was transfected for transient overexpression. Subconfluent cell monolayers were transfected with equal amounts of respective cDNAs which had been cloned into a cytomegalovirus early promoter-based mammalian expression vector (pCMV) and incubated either in the presence of absence of 1 mM orthovanadate for 90 minutes prior to lysis. FIG. 6A shows an antiphosphotyrosine immunoblot of crude cell lysates separated by polyacrylamide gel electrophoresis (SDS-PAGE). In comparison with pCMV vector-transfected controls, two prominent tyrosine-phosphorylated bands were detected in pCMV/MCK-10-2-transfected cells. While based on molecular weight estimates and immunoblot analysis with αMCK-10-C, an antibody directed against a C-terminal peptide (FIG. 6A), the 124 kDa band represented the glycosylated MCK-10 receptor polypeptide, while the 63 kDa band, which was strongly tyrosine-phosphorylated in the MCK-10-2 and to a lesser extent in MCK-10-1-expressing cells, appeared to be a processing product of MCK-10 that included the C-terminal peptide epitope (FIG. 6A). The apparent molecular weight of 63,000 was in agreement with the location of a consensus site for putative proteolytic cleavage by furin in the extracellular region, which indicated that this band represented the β fragment of MCK-10 (FIGS. 6A, 6C and 4B). Detection of a MCK-10-N antibody reactive 54 kD protein, presumably representing the glycosylated extracellular α fragment in conditioned media of transfected NIH 3T3 overexpressing MCK 10-2 and T47D mammary carcinoma cells, supports this interpretation.

Comparison of transiently-expressed MCK-10-2 and MCK-10-1 by immunoblot analysis with the αMCK-10-C antibody revealed approximately equal amounts of a protein doublet for both isoforms (FIG. 6A, right panel) of which only the upper band appeared to be phosphorylated upon stimulation with orthovanadate. The lower band likely represented an intracellular, incompletely glycosylated form of the primary translation product. The antiphosphotyrosine immunoblot further revealed that the 63 kDa putative β subunit was less efficiently phosphorylated than that of MCK-10-2 (FIG. 6A, left panel), although comparable amounts of protein were present. Moreover, this cleavage product of MCK-10-2 appeared to be phosphorylated to a higher extent than the 124 kDa precursor, as judged by comparing antiphosphotyrosine and anti-MCK-10-C immunoblots (FIG. 6A). An additional phosphorylated protein of unknown identity with an apparent molecular weight of 165 kDa was readily detected in lysates of MCK-10-1-transfected 293 cells, whereas it was not detected in cells transfected with the shorter isoform.

In order to examine the extent of MCK-10-2 and MCK-10-1 receptor glycosylation, pCMV expression constructs of both isoforms were transfected into 293 cells and, after metabolic labeling with [$^{35}$S]-L-methionine and treatment with tunicamycin, immunoprecipitates obtained with affinity-purified antibodies against either the N- or C-terminus of MCK-10 were analyzed by gel electrophoresis and autoradiography. From tunicamycin-treated cells, both antibodies precipitated 102 kDa MCK-10-2 and 106 kDa MCK-10-1 bands, presumably representing unglycosylated receptor isoforms and processing intermediates from untreated cells (FIG. 6B). Only the antibody directed against the MCK-10 C-terminus efficiently precipitated the fully processed isoforms. Surprisingly, comparison of mature forms and glycosylation intermediates with the major bands from tunicamycin-treated cells indicated that the absence of the 37 amino acid insertion in the MCK-10-1 cytoplasmic domain correlated with more extensive glycosylation of the extracellular portion of the receptor.

To evaluate the expression of MCK-10 in tumor cell lines, the αMCK-10-N antibody was used for Western blot analysis. As shown in FIG. 6D membrane preparations of T-47D breast carcinoma cells, A431 epidermoid carcinoma cells, SW48 and SNU-C2B colon carcinoma cells, and Caki-2 kidney carcinoma cells contained multiple bands that were recognized by the antibody, including proteins with the same apparent molecular weights as those identified in MCK-10-2 and MCK-10-1 overexpressing 293 cells. The melanoma cell line Hs 294T and the breast carcinoma cell lines HBL-100 and MDA-MB-175, however, displayed unique antigen patterns. Interestingly, Hs 294T cells contained a large MCK-10 form of approximately 165 kDa in addition to a shorter band of 72 kDa.

To determine whether the additional 111 nucleotides present in MCK-10-1 and -3 were ubiquitously expressed or expressed only in specific human tissues, a PCR analysis on different human cDNAs using oligonucleotide primers corresponding to sequences flanking the insertion site was carried out. Parallel PCR amplifications were performed on plasmid DNAs of MCK-10-1/MCK-10-2 as controls. Expression of both isoforms were identified in brain, pancreas, placenta, colon, and kidney, and in the cell lines Caki-2 (kidney ca), SW48 (colon ca), and HBL-100 and T-47D (breast ca). The PCR products were subcloned into the Bluescript vector to confirm the nucleotide sequence.

Using a hybridization probe comprising the 5' 1694 bp cDNA fragment of MCK-10 (excluding the 111 bp insert), which encompasses the extracellular, transmembrane, and juxtamembrane domains, the MCK-10 gene revealed the existence of multiple transcript sizes with a major form of 4.3 kb. The highest expression of MCK-10 mRNA was detected in lung, intermediate levels were found in kidney, colon, stomach, placenta and brain, low levels in pancreas, and no MCK-10 mRNA was detected in liver (FIG. 5A). FIG. 5B illustrates the levels of expression of MCK-10 in a variety of breast cancer cell lines and FIG. 5C presents the levels of MCK-10 expression in different tumor cell lines. A summary of the expression patterns of MCK-10 in different cell lines is presented in TABLE 1.

TABLE 1

MCK-10 EXPRESSION IN DIFFERENT CELL LINES

| BREAST CANCER CELL LINES | |
|---|---|
| BT-474 | + |
| T-47D | ++++ |
| BT-20 | +++ |
| MDA-MB-453 | ++ |
| MDA-MB-468 | ++ |
| MDA-MB-435 | ++ |
| MDA-MB-175 | ++++ |
| MDA-MB-231 | ++ |
| HBL 100 | + |
| SK-BR-3 | + |
| MCF-7 | ++ |
| EMBRYONIC LUNG CANCER,CELL LINES, SV40 TRANSFORMED | |
| WI-38 A13 | + |
| WI-26 A4 | + |
| MELANOMA CELL LINES | |
| SK-Mel-3 | + |
| Wm 266-4 | + |
| HS 294T | ++ |
| COLON CANCER CELL LINES | |
| Caco-2 | +++ |
| SNU-C2B | +++ |
| SW48 | ++ |
| KIDNEY CANCER CELL LINE | +++ |
| CAKI-2 | |
| EPIDERMOID CANCER CELL LINE | ++ |
| A431 | |
| OTHER CANCERS | |
| rhabdomyosarcoma | ++ |
| Ewing sarcoma | ++ |
| glioblastoma | ++ |
| neuroblastoma | − |
| hepatoblastoma | + |
| HEMAPOIETIC CELL LINES | |
| EB3 | − |
| CEM | − |
| MOLT4 | − |
| DAUDI | − |
| RAJI | − |
| MEG01 | − |
| KG1 | − |
| K562 | − |

In situ hybridization analysis with the 5' 1865 bp of MCK-10-2 indicated that MCK-10 was expressed specifically in epithelial cells of various tissues including:

cuboidal epithelial cells lining the distal kidney tubulus columnar epithelial cells lining the large bowel tract deep layer of epithelial cells lining the stomach epithelial cells lining the mammary ducts islet cells of the pancreas epithelial cells of the thyroid gland, which produces thyroid hormones No detectable MCK-10 expression was observed in connective tissues, endothelial cells, adipocytes, muscle cells, or hemopoietic cells.

MCK-10 expression was also detected in all tumors investigated which included:

adenocarcinoma of the colon adenocarcinoma of the stomach adenocarcinoma of the lung infiltrating ductal carcinoma of the breast cystadenoma of the ovary multi endocrine tumor of the pancreas
carcinoid tumor of the pancreas
tubular cells of renal cell carcinoma
transitional cell carcinoma (a malignant epithelial tumor of the bladder)
meningiothelial tumor
medulloblastoma with hyperchromatic atypical nuclei and spare cytoplasm (MCK-10 expression is only seen in cells with well developed cytoplasm)
glioblastoma (a tumor of the neuroepithelial tissue)

The in situ hybridization experiments revealed the highest expression of MCK-10 in malignant cells of the ductal breast carcinoma, in the tumor cells of a multi-endocrine tumor, and in the tumor cells of a transitional cell carcinoma of the bladder.

5.2 The CCK-2 Coding Sequence

The present invention also relates to other members of the MCK-10 family of receptor kinases. Members of the MCK-10 family are defined herein as those proteins coded for by DNA sequences capable of hybridizing to MCK-10 DNA sequences as presented in FIGS. 1A, 1B, 1C, 1D, 1E, 1F and 1G under highly or less highly stringent hybridization conditions. Highly stringent hybridization conditions may be defined as hybridization to filter-bound DNA in 0.5M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wilsy & Sons, Inc., New York, at p. 2.10.3). Less highly stringent conditions, such as moderately stringent conditions, may be defined as hybridizations carried out as described above, followed by washing in 0.2×SSC/0.1% SDS at 42° C. (Ausubel et al., 1989, supra). In instances wherein the nucleic acid molecules are deoxyoligonucleotides ("oligos"), highly stringent conditions may refer, i.e., to washing in 6×SSC/0.5% sodium pyrophosphate at 37° C. (for 14-base oligos), 48° C. (for 17-base oligos) 55° C. (for 20-base oligos), and 60° C. (for 23-base oligos). Such receptors may demonstrate 80% homology at the amino acid level in substantial stretches of DNA sequences. In addition, such receptors can be defined as those receptors containing an intracellular tyrosine kinase domain and a discoidin I sequence located near the amino-terminal end of the protein. The discoidin I domain is defined as that region of MCK-10 located between amino acid 31–185 as presented in FIG. 4A.

In a specific embodiment of the invention described herein, an additional member of the MCK-10 family of receptor tyrosine kinases was cloned and characterized. The nucleotide coding sequence and deduced amino acid sequence of the novel receptor tyrosine kinase, herein referred to as CCK-2, is presented in FIGS. 3A, 3B, 3C, 3D, 3E, 3F, 3G and 3H (SEQ ID NOS:3–4). In accordance with the invention, any nucleotide sequence which encodes the amino acid sequence of the CCK-2 gene product can be used to generate recombinant molecules which direct the expression of CCK-2. In additional embodiments of the invention, nucleotide sequences which selectively hybridize to the CCK-2 nucleotide sequence as shown in FIGS. 3A, 3B, 3C, 3D, 3E, 3F, 3G, 3H (SEQ. ID NO.: 3) may also be used to express gene products with CCK-2 activity.

Analysis of the CCK-2 sequence revealed significant homology to the extracellular, transmembrane and intracellular region of the MCK-10 receptor indicating that it was a member of the MCK-10 family of receptors. The shared homology between CCK-2 and MCK-10 is depicted in FIG. 4A and 4B.

Northern Blot hybridization analysis, indicated that MCK-10 mRNA was highly expressed in cell lines of tumor epithelial origin (FIG. 5D). In contrast, CCK-2 mRNA was found to be expressed in fibroblast-like cell types (FIG. 5D). Comparative in situ hybridization studies revealed an even more defined expression pattern in tissue slices. MCK-10 expression was restricted to subsets of epithelial cells, where no CCK-2 hybridization signal was detected, which was particularly evident in the pancreas, where only endocrine cells types of the islets of Langerhans but not exocrine acini exhibited MCK-10 expression (FIG. 7).

The distinct tissue specificity of MCK-10 and CCK-2 expression was confirmed and even more clearly demonstrated in various sections of primary human carcinomas. Both receptors were expressed in an apparently mutually exclusive manner in different cell types of the same tumor. CCK-2 was predominantly found in all stromal cells, which provide an environment conducive to proliferation, invasion, and even metastasis of epithelial cells, whereas MCK-10 expression was strongly confined to the neoplastic cells themselves. The distinct expression patterns for MCK-10 and CCK-2 suggest that these closely related receptors are involved in interactions between neoplastic epithelial cells and surrounding stroma during tumor progression, and the presence of the discoidin I motif in their extracellular domains strongly indicates an important role for these receptors in processes involved in cell-cell communications.

5.3. Expression of MCK-10 Receptor and Generation of Cell Lines that Express MCK-10

For clarity of discussion the expression of receptors and generation of cell lines expressing receptors are described by way of example for the MCK-10 gene. However, the principles may be analogously applied to expression and generation of cell lines expressing spliced isoforms of MCK-10 or to other members of the MCK-10 family of receptors, such as CCK-2.

In accordance with the invention, MCK-10 nucleotide sequences which encode MCK-10, peptide fragments of MCK-10, MCK-10 fusion proteins or functional equivalents thereof may be used to generate recombinant DNA molecules that direct the expression of MCK-10 protein or a functionally equivalent thereof, in appropriate host cells. Alternatively, nucleotide sequences which hybridize to portions of the MCK-10 sequence may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the MCK-10 protein. Such DNA sequences include those which are capable of hybridizing to the human MCK-10 sequence under stringent conditions.

Altered DNA sequences which may be used in accordance with the invention include deletions, additions or substitutions of different nucleotide residues resulting in a sequence that encodes the same or a functionally equivalent gene product. These alterations would in all likelihood be in regions of MCK-10 that do not constitute functionally conserved regions such as the discodin I domain or the tyrosine kinase domain. In contrast, alterations, such as deletions, additions or substitutions of nucleotide residues in functionally conserved MCK-10 regions would possibly result in a nonfunctional MCK-10 receptor. The gene product itself may contain deletions, additions or substitutions of amino acid residues within the MCK-10 sequence, which result in a silent change thus producing a functionally equivalent MCK-10. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The DNA sequences of the invention may be engineered in order to alter the MCK-10 coding sequence for a variety of ends including but not limited to alterations which modify processing and expression of the gene product. For example, mutations may be introduced using techniques which are well known in the art, e.g. site-directed mutagenesis, to insert new restriction sites, to alter glycosylation patterns, phosphorylation, etc. For example, in certain expression systems such as yeast, host cells may over glycosylate the gene product. When using such expression systems it may be preferable to alter the MCK-10 coding sequence to eliminate any N-linked glycosylation site.

In another embodiment of the invention, the MCK-10 or a modified MCK-10 sequence may be ligated to a heterologous sequence to encode a fusion protein. For example, for screening of peptide libraries it may be useful to encode a chimetic MCK-10 protein expressing a heterologous epitope that is recognized by a commercially available antibody. A fusion protein may also be engineered to contain a cleavage site located between the MCK-10 sequence and the heterologous protein sequence, so that the MCK-10 may be cleaved away from the heterologous moiety.

In an alternate embodiment of the invention, the coding sequence of MCK-10 could be synthesized in whole or in part, using chemical methods well known in the art. See, for example, Caruthers, et al., 1980, Nuc. Acids Res. Symp. Ser. 7: 215–233; Crea and Horn, 180, Nuc. Acids Res. 9 (10): 2331; Matteucci and Caruthers, 1980, Tetrahedron Letters 21: 719; and Chow and Kempe, 1981, Nuc. Acids Res. 9(12): 2807–2817. Alternatively, the protein itself could be produced using chemical methods to synthesize the MCK-10 amino acid sequence in whole or in part. For example, peptides can be synthesized by solid phase techniques, cleaved from the resin, and purified by preparative high performance liquid chromatography. (E.g., see Creighton, 1983, Proteins Structures And Molecular Principles, W. H. Freeman and Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49.

In order to express a biologically active MCK-10, the nucleotide sequence coding for MCK-10, or a functional equivalent, is inserted into an appropriate expression vector, i.e., a vector which contains the necessary elements for the transcription and translation of the inserted coding sequence. The MCK-10 gene products as well as host cells or cell lines transfected or transformed with recombinant MCK-10 expression vectors can be used for a variety of purposes. These include but are not limited to generating antibodies (i.e., monoclonal or polyclonal) that bind to the receptor, including those that competitively inhibit binding of MCK-10 ligand and "neutralize" activity of MCK-10 and the screening and selection of drugs that act via the MCK-10 receptor; etc.

5.3.1. Expression Systems

Methods which are well known to those skilled in the art can be used to construct expression vectors containing the MCK-10 coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the MCK-10 coding sequence. These include but are not limited to microorganisms such as bacteria transformed with recombinant bacteriophage DNA, plasmid DNA or cosmid DNA expression vectors containing the MCK-10 coding sequence; yeast transformed with recombinant yeast expression vectors containing the MCK-10 coding sequence; insect cell systems infected with recombinant virus expression vectors (e.g., baculovirus) containing the MCK-10 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the MCK-10 coding sequence; or animal cell systems. The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the MCK-10 DNA, SV40-, BPV- and EBV-based vectors may be used with an appropriate selectable marker.

In bacterial systems a number of expression vectors may be advantageously selected depending upon the use intended for the MCK-10 expressed. For example, when large quantities of MCK-10 are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2: 1791), in which the MCK-10 coding sequence may be ligated into the vector in frame with the lac Z coding region so that a hybrid AS-lac Z protein is produced; pIN vectors (Inouye & Inouye, 1985, Nucleic acids Res. 13: 3101–3109; Van Heeke & Schuster, 1989, J. Biol. Chem. 264: 5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the MCK-10 coding sequence may be driven by any of a number of promoters. For example, viral promoters such as the 35S RNA and 19S RNA promoters of CaMV (Brisson et al., 1984, Nature 310: 511–514), or the coat protein promoter of TMV (Takamatsu et al., 1987, EMBO J. 6: 307–311) may be used; alternatively, plant promoters such as the small subunit of RUBISCO (Coruzzi et al., 1984, EMBO J. 3: 1671–1680; Broglie et al., 1984, Science 224: 838–843); or heat shock promoters, e.g., soybean hsp17.5-E or hsp17.3-B (Gurley et al., 1986, Mol. Cell. Biol. 6: 559–565) may be used. These constructs can be introduced into plant cells using Ti plasmids, Ri plasmids, plant virus vectors, direct DNA transformation, microinjection, electropotation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express MCK-10 is an insect system. In one such system, *Autographa californica* nuclear polyhidrosis virus (AcNPV) is used as a vector to express foreign genes. The virus grows in *Spodoptera frugiperda* cells. The MCK-10 coding sequence may be cloned into non-essential regions (for example the polyhedrin gene) of the virus and placed under control of an AcNPV promoter (for example the polyhedrin promoter). Successful insertion of the MCK-10 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Viol. 46: 584; Smith, U.S. Pat. No. 4,215,051).

In mammalian host cells, a number of viral based expression systems may be utilized. In cases where an adenovirus is used as an expression vector, the MCK-10 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing MCK-10 in infected hosts. (e.g., See Logan & Shenk, 1984, Proc. Natl. Acad. Sci. (USA) 81: 3655-3659). Alternatively, the vaccinia 7.5K promoter may be used. (See, e.g., Mackett et al., 1982, Proc. Natl. Acad. Sci. (USA) 79: 7415–7419; Mackett et al., 1984, J. Virol. 49: 857–864; Panicali et al., 1982, Proc. Natl. Acad. Sci. 79: 4927–4931).

Specific initiation signals may also be required for efficient translation of inserted MCK-10 coding sequences. These signals include the ATG initiation codon and adjacent sequences. In cases where the entire MCK-10 gene, including its own initiation codon and adjacent sequences, is inserted into the appropriate expression vector, no additional translational control signals may be needed. However, in cases where only a portion of the MCK-10 coding sequence is inserted, exogenous translational control signals, including the ATG initiation codon, must be provided. Furthermore, the initiation codon must be in phase with the reading frame of the MCK-10 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153: 516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of four consensus N-glycosylation sites in the MCK-10 extracellular domain support that proper modification may be important for MCK-10 function. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the MCK-10 may be engineered. Rather than using expression vectors which contain viral origins of replication, host cells can be transformed with the MCK-10 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the MCK-10 on the cell surface. Such engineered cell lines are particularly useful in screening for drugs that affect MCK-10.

A number of selection systems may be used, including but not limited to the herpes simplex virus thymidine kinase (Wigler, et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817) genes can be employed in tk⁻, hgprt⁻ or aprt⁻ cells, respectively. Also, antimetabolite resistance can be used as the basis of selection for dhfr, which confers resistance to methotrexate (Wigler, et al., 1980, Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981), Proc. Natl. Acad. Sci. USA 78: 2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85: 8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.3.2. Identification of Transfectants or Transformants that Express the MCK-10

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of MCK-10 mRNA transcripts in the host cell; and (d) detection of the gene product as measured by immunoassay or by its biological activity.

In the first approach, the presence of the MCK-10 coding sequence inserted in the expression vector can be detected by DNA-DNA or DNA-RNA hybridization using probes comprising nucleotide sequences that are homologous to the MCK-10 coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the MCK-10 coding sequence is inserted within a marker gene sequence of the vector, recombinants containing the MCK-10 coding sequence can be identified by the absence of the marker gene function. Alternatively, a marker gene can be placed in tandem with the MCK-10 sequence under the control of the same or different promoter used to control the expression of the MCK-10 coding sequence. Expression of the marker in response to induction or selection indicates expression of the MCK-10 coding sequence.

In the third approach, transcriptional activity for the MCK-10 coding region can be assessed by hybridization assays. For example, RNA can be isolated and analyzed by Northern blot using a probe homologous to the MCK-10 coding sequence or particular portions thereof. Alternatively, total nucleic acids of the host cell may be extracted and assayed for hybridization to such probes.

In the fourth approach, the expression of the MCK-10 protein product can be assessed immunologically, for example by Western blots, immunoassays such as radioimmuno-precipitation, enzyme-linked immunoassays and the like.

5.4. Uses of the MCK-10 Receptor and Engineered Cell Lines

MCK-10 is expressed in a variety of normal tissues, including brain tissue. The MCK-10 receptor tyrosine kinase shares homology with the TrK neurotropin receptor, indicating that modulators of MCK-10 may be used to treat a variety of neurological disorders characterized by one or more of the following symptoms: astasia, aphasia, paralysis, paresa and paralegies. Such nervous system disorders include, but are not limited to, Alzheimer's disease, Parkinson's disease, Lou Gehrig's disease (ALS), trauma, damaged or severed nerve injuries, Huntington's chorea, multiple sclerosis, muscular dystrophy syringomiplia, Tabes Dorsalis and cardiovascular accidents.

Northern blot analysis and in situ hybridization also indicates that MCK-10 and CCK-2 are expressed in a wide variety of cancer cells and tumor tissue. Thus, the present invention relates to inhibitors of MCK-10 and CCK-2 receptor activity which may have therapeutic value in the treatment of proliferative diseases such as cancer.

For clarity of discussion the uses of the expressed receptors and engineered cell lines expressing the receptors is described by way of example for MCK-10. The described uses may be equally applied to expression of MCK-10 spliced isoforms or additional members of the MCK-10 gene family such as CCK-2.

In an embodiment of the invention the MCK-10 receptor and/or cell lines that express the MCK-10 receptor may be used to screen for antibodies, peptides, or other ligands that act as agonists or antagonists of the MCK-10 receptor. For example, anti-MCK-10 antibodies may be used to inhibit MCK-10 function. Alternatively, screening of peptide libraries with recombinantly expressed soluble MCK-10 protein or cell lines expressing MCK-10 protein may be useful for identification of therapeutic molecules that function by modulating the biological activity of MCK-10. The uses of the MCK-10 receptor and engineered cell lines, described in the subsections below, may be employed equally well for MCK-10 family of receptor tyrosine kinases.

In an embodiment of the invention, engineered cell lines which express the entire MCK-10 coding region or its ligand binding domain may be utilized to screen and identify ligand antagonists as well as agonists. Synthetic compounds, natural products, and other sources of potentially biologically active materials can be screened in a number of ways.

5.4.1. Screening of Peptide Library with MCK-10 Protein or Engineered Cell Lines Random peptide libraries consisting of all possible combinations of amino acids attached to a solid phase support may be used to identify peptides that are able to bind to the ligand binding site of a given receptor or other functional domains of a receptor such as kinase domains (Lam, K. S. et al., 1991, Nature 354: 82–84). The screening of peptide libraries may have therapeutic value in the discovery of pharmaceutical agents that act to inhibit the biological activity of receptors through their interactions with the given receptor.

Identification of molecules that are able to bind to the MCK-10 may be accomplished by screening a peptide library with recombinant soluble MCK-10 protein. Methods for expression and purification of MCK-10 are described in Section 5.2.1 and may be used to express recombinant full length MCK-10 or fragments of MCK-10 depending on the functional domains of interest. For example, the kinase and extracellular ligand binding domains of MCK-10 may be separately expressed and used to screen peptide libraries.

To identify and isolate the peptide/solid phase support that interacts and forms a complex with MCK-10, it is necessary to label or "tag" the MCK-10 molecule. The MCK-10 protein may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label, to MCK-10, may be performed using techniques that are routine in the art. Alternatively, MCK-10 expression vectors may be engineered to express a chimeric MCK-10 protein containing an epitope for which a commercially available antibody exist. The epitope specific antibody may be tagged using methods well known in the art including labeling with enzymes, fluorescent dyes or colored or magnetic beads.

The "tagged" MCK-10 conjugate is incubated with the random peptide library for 30 minutes to one hour at 22° C. to allow complex formation between MCK-10 and peptide species within the library. The library is then washed to remove any unbound MCK-10 protein. If MCK-10 has been conjugated to alkaline phosphatase or horseradish peroxidase the whole library is poured into a petri dish containing substrates for either alkaline phosphatase or peroxidase, for example, 5-bromo-4-chloro-3-indoyl phosphate (BCIP) or 3,3',4,4"-diamnobenzidine (DAB), respectively. After incubating for several minutes, the peptide/solid phase-MCK-10 complex changes color, and can be easily identified and isolated physically under a dissecting microscope with a micromanipulator. If a fluorescent tagged MCK-10 molecule has been used, complexes may be isolated by fluorescent activated sorting. If a chimeric MCK-10 protein expressing a heterologous epitope has been used, detection of the peptide/MCK-10 complex may be accomplished by using a labeled epitope specific antibody. Once isolated, the identity of the peptide attached to the solid phase support may be determined by peptide sequencing.

In addition to using soluble MCK-10 molecules, in another embodiment, it is possible to detect peptides that bind to cell surface receptors using intact cells. The use of intact cells is preferred for use with receptors that are multi-subunits or labile or with receptors that require the lipid domain of the cell membrane to be functional. Methods for generating cell lines expressing MCK-10 are described in Sections 5.2.1. and 5.2.2. The cells used in this technique may be either live or fixed cells. The cells will be incubated with the random peptide library and will bind to certain peptides in the library to form a "rosette" between the target cells and the relevant solid phase support/peptide. The rosette can thereafter be isolated by differential centrifugation or removed physically under a dissecting microscope.

As an alternative to whole cell assays for membrane bound receptors or receptors that require the lipid domain of the cell membrane to be functional, the receptor molecules can be reconstituted into liposomes where label or "tag" can be attached.

5.4.2. Antibody Production and Screening

Various procedures known in the art may be used for the production of antibodies to epitopes of the recombinantly produced MCK-10 receptor. Such antibodies include but are not limited to polyclonal, monoclonal, chimeric, single chain, Fab fragments and fragments produced by an Fab expression library. Neutralizing antibodies i.e., those which compete for the ligand binding site of the receptor are especially preferred for diagnostics and therapeutics.

Monoclonal antibodies that bind MCK-10 may be radioactively labeled allowing one to follow their location and distribution in the body after injection. Radioactivity tagged antibodies may be used as a non-invasive diagnostic tool for imaging de novo cells of tumors and metastases.

Immunotoxins may also be designed which target cytotoxic agents to specific sites in the body. For example, high affinity MCK-10 specific monoclonal antibodies may be covalently complexed to bacterial or plant toxins, such as diphtheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate MCK-10 expressing tumor cells.

For the production of antibodies, various host animals may be immunized by injection with the MCK-10 protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to MCK-10 may be prepared by using any technique which provides for the production of antibody molecules by continuous cell lines in culture. These include but are not limited to the hybridoma technique originally described by Kohler and Milstein, (Nature, 1975, 256: 495–497), the human B-cell hybridoma technique (Kosbor et al., 1983, Immunology Today, 4: 72; Cote et al., 1983, Proc. Natl. Acad. Sci., 80: 2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81: 6851–6855; Neuberger et al., 1984, Nature, 312: 604–608; Takeda et al., 1985, Nature, 314: 452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946, 778) can be adapted to produce MCK-10-specific single chain antibodies.

Antibody fragments which contain specific binding sites of MCK-10 may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246: 1275–1281) to allow rapid and easy identification of monoclonal Fab fragments with the desired specificity to MCK-10.

5.5. Uses of MCK-10 Coding Sequence

The MCK-10 coding sequence may be used for diagnostic purposes for detection of MCK-10 expression. Included in the scope of the invention are oligoribonucleotide sequences, that include antisense RNA and DNA molecules and ribozymes that function to inhibit translation of MCK-10. In addition, mutated forms of MCK-10, having a dominant negative effect, may be expressed in targeted cell populations to inhibit the activity of endogenously expressed MCK-10. The uses described below may be equally well adapted for MCK-10 spliced isoform coding sequences and sequences encoding additional members of the MCK-10 family of receptors, such as CCK-2.

5.5.1. Use of MCK-10 Coding Sequence in Diagnostics and Therapeutics

The MCK-10 DNA may have a number of uses for the diagnosis of diseases resulting from aberrant expression of MCK-10. For example, the MCK-10 DNA sequence may be used in hybridization assays of biopsies or autopsies to diagnose abnormalities of MCK-10 expression; e.g., Southern or Northern analysis, including in situ hybridization assays.

Also within the scope of the invention are oligoribonucleotide sequences, that include anti-sense RNA and DNA molecules and ribozymes that function to inhibit the translation of MCK-10 mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the MCK-10 nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of MCK-10 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

5.5.2. Use of Dominant Negative MCK-10 Mutants in Gene Therapy

Receptor dimerization induced by ligands, is thought to provide an allosteric regulatory signal that functions to couple ligand binding to stimulation of kinase activity. Defective receptors can function as dominant negative mutations by suppressing the activation and response of normal receptors by formation of unproductive heterodimers. Therefore, defective receptors can be engineered into recombinant viral vectors and used in gene therapy in individuals that inappropriately express MCK-10.

In an embodiment of the invention, mutant forms of the MCK-10 molecule having a dominant negative effect may be identified by expression in selected cells. Deletion or missense mutants of MCK-10 that retain the ability to form dimers with wild type MCK-10 protein but cannot function in signal transduction may be used to inhibit the biological activity of the endogenous wild type MCK-10. For example, the cytoplasmic kinase domain of MCK-10 may be deleted resulting in a truncated MCK-10 molecule that is still able to undergo dimerization with endogenous wild type receptors but unable to transduce a signal.

Recombinant viruses may be engineered to express dominant negative forms of MCK-10 which may be used to inhibit the activity of the wild type endogenous MCK-10. These viruses may be used therapeutically for treatment of diseases resulting from aberrant expression or activity of MCK-10, such as cancers.

Expression vectors derived from viruses such as retroviruses, vaccinia virus, adeno-associated virus, herpes viruses, or bovine papilloma virus, may be used for delivery of recombinant MCK-10 into the targeted cell population. Methods which are well known to those skilled in the art can be used to construct those recombinant viral vectors containing MCK-10 coding sequence. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant MCK-10 molecules can be reconstituted into liposomes for delivery to target cells.

6. EXAMPLES: CLONING AND CHARACTERIZATION OF MCK-10

The subsection below describes the isolation and characterization of a cDNA clones encoding the novel receptor tyrosine kinase designated MCK-10 and differentially spliced isoforms of MCK-10.

6.1. Materials and Methods

6.1.1. cDNA Cloning and Characterization of MCK-10

Confluent plates of the human breast cancer cell line MCF7 (American Type Culture Collection HTB22) were lysed by treatment with guanidinium-thiocyanate according to Chirgwin et al. (1979, Biochemistry 18: 5294–5299). Total RNA was isolated by CsCl-gradient centrifugation. First-strand cDNA was synthesized from 20 µg total RNA with avian myeloblastosis virus (AMV) reverse transcriptase (Boehringer Mannheim).

cDNA was used in a polymerase chain reaction under standard conditions (PCR Technology-Principles and Applications for DNA Amplifications, H. E. Erlich, ed., Stockton Press, New York 1989). The following pool of primers were used for the amplification:

```
Sense Primer (SEQ ID NO:9)
corresponding to the amino acid sequence HRDLAA
     EcoRI
5'   GGAATTCC    CAC  AGN  GAC  TTN  GCN  GCN  AG 3'
                      T    C    A    T    C    A    A    C
Antisense Primer (SEQ ID NO:10)

corresponding to the amino acid sequence SDVWS
F/Y
EcoRI
3'   TCN  GAC  GTN  TGG  ACN    TTC    CCTTAAGG 5'
      G         G          TG    CAT
```

Thirty-five PCR cycles were carried out using 8 µg (0.8 µg) of the pooled primers. (Annealing 55° C., 1 min; Extension 72° C., 2 min; Denaturation 94° C., 1 min). The reaction product was subjected to polyacrylamide gel electrophoresis. Fragments of the expected size (~210 bp) were isolated, digested with the restriction enzyme EcoRI, and subcloned into the pBluescript vector (Stratagene) using standard techniques (*Current Protocols in Molecular Biology*, eds. F. M. Ausubel et al., John Wiley & Sons, New York, 1988).

The recombinant plasmids were transformed into the competent *E. coli* strain designated 298.

The subcloned PCR products were sequenced by the method of Sanger et al. (Proc. Natl. Acad. Sci. USA 74, 5463–5467) using Sequenase (United States Biochemical, Cleveland, Ohio 44111 USA). One clone, designated MCK-10 was identified as novel RTK.

6.1.2. Full-Length cDNA Cloning

The partial cDNA sequence of the new MCK-10 RTK, which was identified by PCR, was used to screen a λgt11 library from human fetal brain cDNA (Clontech) (complexity of $1\times10^{10}$ recombinant phages). One million independent phage clones were plated and transferred to nitrocellulose filters following standard procedures (Sambrook, H. J., Molecular Cloning, Cold Spring Harbor Laboratory Press, USA, 1989). The filters were hybridized to the EcoRI/EcoRI fragment of clone MCK-10, which had been radioactively labeled using 50 µCi [$\alpha^{32}$P]ATP and the random-primed DNA labeling kit (Boehringer Mannheim). The longest cDNA insert (8) of ~3500 bp was digested with the restriction enzymes EcoRI/SacI to obtain a 5' end probe of ~250 bp. This probe was used to rescreen the human fetal brain library and several overlapping clones were isolated. The composite of the cDNA clones are shown in FIGS. 1A, 1B, 1C, 1D, 1E, 1F and 1G. Some of the clones had a deletion of 6 amino acids at position 2315 in the MCK-10 sequence.

The 1.75 million independent phage clones of a human placenta library, λZAP were plated and screened with the 5' end probe (EcoRI/SacI) of clone 8. Two clones were full-length with a shorter 5' end starting at position 278 of the nucleotide sequence shown in FIGS. 1A, 1B, 1C, 1D, 1E, 1F and 1G (SEQ ID NO:1). Subcloning of positive bacteriophages clones into pBluescript vector was done by the in vivo excision protocol (Stratagene).

The composite cDNA sequence and the predicted amino acid sequence of MCK-10 are shown in FIGS. 1A, 1B, 1C, 1D, 1E, 1F and 1G (SEQ ID NOS:1–2). Different cDNA sequence variations of MCK-10 is presented in FIG. 2A.

6.1.3. Northern Blot Analysis of MCK-10

Total RNA was isolated from the following human tissues: lung, pancreas, stomach, kidney, spleen, liver, colon and placenta. RNA was also isolated from various breast cancer cell lines and cell lines of tumor origin.

PolyA$^+$ RNA was isolated on an oligo (dT) column (Aviv and Leder, 1972, Proc. Natl. Acad. Sci. USA 69, 1408–1412). The RNA was separated on an agarose gel containing 2.2M formaldehyde and blotted on a nitrocellulose filter (Schleicher and Schuell). 3 µg of poly A$^+$ RNA was loaded per lane. The filters were either hybridized with a $^{32}$P-labeled EcoRI/EcoRI DNA fragment obtained by PCR or by a 1694 bp cDNA fragment of MCK-10-2 (excluding the 111 bp insert) which encompasses the extracellular, transmembrane and juxtamembrane domain. Subsequently, the filter was exposed to x-ray film at –70° C. with an intensifying screen. The results are depicted in FIGS. 5A, 5B and 5C.

6.1.4. Generation of MCK-10 Specific Antibodies

Antisera was generated against synthetic peptides corresponding to the amino acid sequence of MCK-10-2. αMCK-10-N antisera was generated against the following N-terminal peptide located between amino acids 26–42 (SEQ ID NO:11)

H-F-D-P-A-K-D-C-R-Y-A-L-G-M-Q-D-R-T-I.

αMCK-10-c antisera was generated against the following C-terminal peptide located between amino acids 902–919 (SEQ ID NO:12)

R-P-P-F-S-Q-L-H-R-F-L-A-E-D-A-L-N-T-V.

αMCK-10-β antisera was generated against the following peptide near the processing site of β-subunit of MCK-10 located between amino acids 309–322 (SEQ ID NO:13):

P-A-M-A-W-E-G-E-P-M-R-H-N-L.

αMCK-10-C2 antisera was generated against the C-terminal peptide located between amino acids 893–909 (SEQ ID NO:14):

C-W-S -R-E-S-E-Q-R-P-P-F-S-Q-L-H-R.

Peptides were coupled to keyhole limpet hemocyanin and injected with Freunds adjuvant into Chinchilla rabbits. After the second boost, the rabbits were bled and the antisera were tested in immunoprecipitations using lysates of 293 cells transiently overexpressing MCK-10-1 and MCK-10-2.

The samples were loaded on a 7.5% polyacrylamide gel and after electrophoresis transferred onto a nitrocellulose filter (Schleicher and Schuell). The blot was probed with the different antibodies as above and developed using the ECL Western blotting detection system according the manufacturer's instructions (Cat no. RPN 2108 Amersham International, UK).

6.1.5. In Situ Hybridization

The 5' located cDNA fragment corresponding to nucleotides 278–1983 of clone MCK-10-2, excluding the 111 base pair insert, were subcloned in the bluescript SK+ (Stratagene). For in situ hybridization, a single-strand antisense DNA probe was prepared as described by Schnürch and Risau (Development 1991, 111, 1143–1154). The plasmid was linearized at the 3'end of the cDNA and a sense transcript was synthesized using SP6 RNA polymerase (Boehringer). The DNA was degraded using DNase (RNase-free preparation, Boehringer Mannheim). With the transcript, a random-primed cDNA synthesis with α-$^{35}$S ATP (Amersham) was performed by reverse transcription with MMLV reverse transcriptase (BRL). To obtain small cDNA fragments of about 100 bp in average, suitable for in situ hybridization, a high excess of primer was used. Subsequently, the RNA transcript was partially hydrolyzed in 100 nM NaOH for 20 min at 70° C., and the probe was neutralized with the same amount of HCL and purified with a Sephadex-G50 column. After ethanol precipitation the probe was dissolved at a final specific activity of $5 \times 10^5$ cpm. For control hybridization, a sense probe was prepared using the same method.

Sectioning, postfixation and hybridization was essentially performed according to Hogan et al. (1986, Manipulating the Mouse Embryo: A Laboratory Manual, New York: Cold Spring Harbor Laboratory Press). 10 µm thick sections were cut at −18° C. on a Leitz cryostat. For hybridization treatment, no incubation with 0.2M HCL for removing the basic proteins was performed. Sections were incubated with the $^{35}$S-cDNA probe ($5 \times 10^4$ cpm/µl) at 52° C. in a buffer containing 50% formamide, 300 mM NaCl, 10 mM Tris-HCL, 10 mM NaPO$_4$ (pH 6.8), 5 mM EDTA, 2% Ficoll 400, 0.2% polyvinylpyrrolidone, 0.02% BSA, 10 mg/ml yeast RNA, 10% dextran sulfate, and 10 mM DTT. Posthybridization washing was performed at high stringency (50% formamide, 300 mM NaCl, 10 mM Tris-HCL, 10 mM NaPO$_4$ (pH6.8), 5 mM EDTA, 10 mM DTT at 52° C.). For autoradiography, slides were created with Kodak NTB2 film emulsion and exposed for eight to ten days. After developing, the sections were counterstained with toluidine blue.

6.2. Results

6.2.1. Characterization of MCK-10 Clone

To identify novel receptor tyrosine kinases (RTKs) that are expressed in mammary carcinoma cell lines, we used the polymerase chain reaction in combination with two degenerate oligonucleotide primer pools based on highly conserved sequences within the kinase domain of RTKs, corresponding to the amino acid sequence HRDLAA (SEQ ID NO:6) (sense primer) and SDVWS/FY (SEQ ID NO:7) (antisense primer) (Hanks et al. 1988, Science 241, 42–52), in conjunction with cDNA synthesized by reverse transcription of poly A RNA from the human mammary carcinoma cell line MCF7. We identified a novel RTK, designated MCK-10 (mammary carcinoma kinase 10), that within the tyrosine kinase domain exhibited extensive sequence similarity to the insulin receptor family. The PCR fragment was used to screen a lambda gt11 library of human fetal brain cDNA (Clontech). Several overlapping clones were identified and their composite sequence is shown in FIGS. 1A, 1B and 1C. Furthermore, screening of a human placenta library yielded two cDNA clones which encoded the entire MCK-10 protein but whose 5' nucleotide sequence began at nucleotide 278 in the sequence shown in FIG. 1. Sequence analysis of the two clones revealed complete identity with the exception of 111 additional nucleotides within the juxtamembrane domain, between nucleotides 1832 and 1943. One of the clones isolated from the human fetal brain library contained an additional 18 nucleotides in the tyrosine kinase domain. These sequences were in-frame with the MCK-10 open reading frame and did not contain any stop codons. We designated these MCK-10 splice isoforms MCK-10-1 (with the additional 111 bp), MCK-10-2 (without any insertions), MCK-10-3 (with the additional 111 bp and 18 bp), and MCK-10-4 (with the additional 18 bp). This new receptor tyrosine kinase was recently described by Johnson et al. (1993, Proc. Natl. Acad. Sci. USA, 90, 5677–5681) as DDR.

As shown in FIG. 1, MCK-10 has all of the characteristics of a receptor PTK: the initiation codon is followed by a stretch of essentially hydrophobic amino acids, which may serve as a signal peptide. Amino acids 418-439 are also hydrophobic in nature, with the characteristics of a transmembrane region. The extracellular domain encompasses 4 consensus N-glycosylation sites (AsnXSer/Thr) and 7 cysteine residues. The extracellular region is shorter than that of the insulin receptor family and shows no homology to other receptor tyrosine kinases, but contains near the N-terminus the consensus sequences for the discoidin 1 like family (Poole et al. 1981, J. Mol. Biol. 153, 273–289), which are located as tandem repeats in MGP and BA46, two milk fat globule membrane proteins (Stubbs et al. 1990, proc. Natl. Acad. Sci. USA, 87, 8417–8421, Larocca et al. 1991, Cancer Res. 51, 4994–4998), in the light chains of factor V (Kane et al. 1986, Proc. Natl. Acad. Sci. USA, 83, 6800–6804) and VIII (Toole et al. 1984, Nature, 312, 342–347), and in the A5 protein (Takagi et al. 1987, Dev. Biol., 122, 90–100).

The protein backbone of MCK-10-1 and MCK-10-2 proreceptors, with predicted molecular weights of 101.13 and 97.17 kD, respectively, can thus be subdivided into a 34.31 kD α subunit, and a 66.84 kD and a 62.88 kD β-subunit, respectively, that contain the tyrosine kinase homology and alternative splice sites.

The consensus sequence for the ATP-binding motif is located at positions 617–627 (FIGS. 1A, 1B, 1C, 1D, 1E, 1F and 1G). When compared with other kinases, the ATP binding domain is 176 amino acids (including the additional 37 amino acids) further from the transmembrane domain than any other tyrosine kinase. The additional 37 amino acids are located in the long and proline/glycine-rich juxtamembrane region and contain an NPAY sequence (where A can be exchanged for any amino acid), which is found in cytoplasmic domains of several cell surface proteins, including RTKs of the EGF and insulin receptor families (Chen et al. 1990, J. Biol. Chem., 265, 3116–3123). This consensus motif is followed by the sequence TYAXPXXXPG (SEQ ID NO:8), which is repeated downstream in MCK-10 in the juxtamembrane domain at positions 585–595. Recently it has been shown that this motif is deleted in the cytoplasmic juxtamembrane region of the activin receptor, a serine/threonine kinase, resulting in reduced ligand binding affinity (Attisano et al. 1992, Cell, 68, 97–108).

In comparison with other RTKs, the catalytic domain shows the highest homology to the TrkA receptor. The yy-motifs (position 802/803) and the tyrosine at position 798, representing putative autophosphorylation sites, characterize MCK-10 as a member of the insulin receptor family (FIGS. 1A, 1B, 1C, 1D, 1E, 1F and 1G). Finally, MCK-10 shares with the Trk kinases their characteristic short caraboxy-terminal tail of 9 amino acids.

To determine whether the additional 111 nucleotides present in MCK-10-1 and -3 were ubiquitously expressed or expressed only in specific human tissues, we performed PCR on different human cDNAs using oligonucleotide primers corresponding to sequences flanking the insertion site. Parallel PCR amplifications were performed on plasmid DNAs of MCK-10-1/MCK-10-2 as controls. Expression of both isoforms was identified in brain, pancreas, placenta, colon, and kidney, and in the cell lines Caki-2 (kidney ca), SW48 (colon ca), and HBL-100 and T-47D (breast ca). The PCR products were subcloned into the Bluescript vector to confirm the nucleotide sequence.

6.2.2. Northern Blot Analysis: Expression of MCK-10 in Various Human Tissues and Cell Lines Using as a hybridization probe a 5' 1694 bp cDNA fragment of MCK-10 (excluding the 111 base pair insert), which encompasses the extracellular, transmembrane, and juxtamembrane domains, the MCK-10 gene revealed the existence of multiple transcript sizes with a major form of 4.3 kb. The highest expression of MCK-10 mRNA was detected in lung, intermediate levels were found in kidney, colon, stomach, placenta, and brain, low levels in pancreas, and no MCK-10 mRNA was detected in liver (FIG. 5A). MCK-10 mRNA was also detected in a variety of different tumor cell lines as depicted in FIG. 5B and FIG. 5C. Northern blot analysis with the GAPDH gene was carried out as a control.

6.2.3. In Situ Hybridization

To determine which cells in the different human tissues contain MCK-10 transcripts, in situ hybridization of various human tissues and of tissues of different tumors were carried out. Hybridization analyses with the 5' 1694 bp of MCK-10 (excluding the 111 base pair insert) indicated that MCK-10 expression was specifically detected in epithelial cells of various tissues:

cuboidal epithelial cells lining the distal kidney tubulus columnar epithelial cells lining the large bowl tract deep layer of epithelial cells lining the stomach epithelial cells lining the mammary ducts islet cells of the pancreas epithelial cells of the thyroid gland, which produces thyroid hormones No detectable MCK-10 expression was observed in connective tissues, endothelial cells, adipocytes, muscle cells, or hemapoletic cells.

MCK-10 expression was detected in all tumors investigated:

adenocarcinoma of the colon adenocarcinoma of the stomach adenocarcinoma of the lung infiltrating ductal carcinoma of the breast cystadenoma of the ovary multi endocrine tumor of the pancreas carcinoid tumor of the pancreas tubular cells of renal cell carcinoma transitional cell carcinoma (a malignant epithelial tumor of the bladder)

meninglothelial tumor medulloblastoma with hyperchromatic atypical nuclei and spare cytoplasm (MCK-10 expression is only seen in cells with well developed cytoplasm)

glioblastoma (a tumor of the neuroepithelial tissue)

These in situ hybridization experiments revealed the highest expression of MCK-10 in malignant cells of the ductal breast carcinoma, in the tumor cells of a multi endocrine tumor, and in the tumor cells of a transitional cell carcinoma of the bladder.

6.2.4. Transient Expression of MCK-10 in 293 Cells

To analyze the MCK-10 protein in detail, we used the 293 cell system for transient overexpression. The cDNAs of MCK-10-1 and MCK-10-2 were cloned into an expression vector. Cells were transfected in duplicate with the two splice variants or a control plasmid and starved overnight. One part was incubated prior to lysis with 1 mM sodium-orthovanadate for 90 min. This agent is known to be a potent inhibitor of phosphotyrosine phosphatases, thereby enhancing the tyrosine phosphorylation of cellular protein.

The precursor and the β-subunit of MCK-10 showed strong tyrosine phosphorylation after orthovanadate treatment, (FIG. 6A, left panel). Surprisingly, the MCK-10-1, containing the 37 amino acid insertion, exhibited lower kinase activity than MCK-10-2. Reprobing the same blot with a peptide antibody raised against the MCK-10 C-terminus revealed equal amounts of expressed receptor and a slight shift of MCK-10-1 precursor and β-subunit due to the additional 37 amino acids of the insertion (FIG. 6A, right panel).

We further analyzed the N-linked glycosylation of the splice variants. Transfected cells were treated overnight with tunicamycin, which inhibits the maturation of proteins by glycosylation. Two affinity purified antibodies raised against peptide sequence of MCK-10 N- and C-terminus, respectively, were used for subsequent immunoprecipitations. Both antibodies precipitated the predicted 101 kD or 97 kD polypeptides from tunicamycin-treated cells (FIG. 6B). Interestingly, the size of the fully glycosylated forms of MCK-10-1 and MCK-10-2 suggested that the latter was more extensively glycosylated than the putative alternative splice form.

In summary, transient overexpression experiments demonstrate significant effects of the 37 amino acid insertion on receptor function. Both receptor kinase activity and extracellular glycosylation appeared to be significantly affected by the additional sequences present in MCK-10-1 which may influence ligand binding. Although orthovanadate-induced tyrosine phosphorylation was reduced for both the 124 kD form as well as the 63 kD cleavage product, possibly representing a β subunit, surprisingly, the MCK-10-1 type receptor was less extensively glycosylated than the MCK-10-2 isoform, which resulted in an approximately equal apparent molecular weight for the mature forms of both variants. The latter phenomenon may be mediated by either or all of the protein binding motifs and may lead, through interaction with cytoskeletal components for which both NXXY and SH3 domain involvement has been suggested (Reszka et al. 1992, J. Cell Biol. 117: 1321–1330; Musacchio et al., 1992, FEBS letters 307: 55–61), to differential sorting, modification, and possibly even cellular localization. Moreover, the resulting differences in extracellular carbohydrate side chain modification pattern may affect ligand binding and therefore autophosphorylation of MCK-10 alternative splice forms.

A potentially even greater diversity of MCK-10 gene products than suggested by cDNA cloning results became apparent through immunoblot analysis of human tumor cell lines, which indicated cell line-characteristic quantitative and qualitative differences. The expression pattern complexity revealed by the extracellular domain-specific MCK-10-N antibody may be the result of either differential glycosylation or the existence of additional alternative splicing variants or both. This remarkable complexity of MCK-10 isoforms in tumor cells in conjunction with the presence of a discoidin I domain potentially involved in cell adhesion, and the possibility of SH3 protein-mediated connections with the cytoskeleton suggests an intricately regulated role of MCK-10 in cell-cell interaction and possibly tumor invasion or metastasis. Interestingly, cleavage of the MCK-10 extracellular domain at the RXRR consensus sequence, yielding a soluble 54 kD α-subunit with putative adhesion properties due to the presence of the discoidin I-like domain may represent another regulatory mechanism in tumor progression, when cancer cells adhere to, as well as detach from, the extracellular matrix. Similar post-translational processing by endoprotease cleavage has been shown for cell adhesion molecules such as Ng-CAM (Burgoon et al., 1992, J. Cell Biol. 112: 1017–1029) and for the receptor phosphatases PTPμ and PTPκ, which mediate hemophilic intercellular interactions (Brady-Kalnay et al., 1993, J. Cell Biol. 122: 961–972; Jiang et al., 1993, Mol. Cell Biol. 13: 2942–2951; Sap et al., 1994, Mol Cell Biol. 14: 1–9).

7. EXAMPLES: CLONING AND CHARACTERIZATION OF CCK-2

The following subsection describes methods for isolation and characterization of the CCK-2 gene, an additional member of the MCK-10 receptor tyrosine kinase gene family.

7.1. Materials and Methods

7.1.1. cDNA Cloning and Characterization of CCK-2 cDNA was synthesized using avian myeloblastosis virus reverse transcriptase and 5 μg of poly A$^+$ RNA prepared from tissue of a primary colonic adenocarcinoma, sigmoid colon, moderately well differentiated grade II, staging pT3, pN1, removed from a 69 year old white female of blood type O, RH positive. The patient had not received therapy.

The tissue was minced and lysed by treatment with guanidinium-thiocyanate according to Chirgwin, J. M. et al. (1979, Biochemistry 18: 5294–5299). Total RNA was isolated by guanidinium thiocyanate-phenol-chloroform extraction (Chomczyrski et al. 1987, Anal. Biochem. 162: 156–159). Poly A$^+$ RNA was isolated on an oligo-dT column (Aviv and Leder, 1972, Proc. Natl. Acad. Sci. USA 69: 1408–1412).

One tenth of the cDNA was subjected to the polymerase chain reaction using standard conditions (PCR Technology-Principles and Applications for DNA Amplifications, H. E. Erlich, ed. Stockton Press, New York, 1989) and the same pool of primers used for amplification of MCK-10 (See, Section 6.1.1., page 46, lines 4–16). Thirty-five cycles were carried out (Annealing 55° C., 1 min; Extension 72° C., 2 min: Denaturation 94° C. 1 min.). The reaction products were subjected to polyacrylamide gel electrophoresis. Fragments of the expected size were isolated, digested with the restriction enzyme EcoRI, and subcloned into pBluescript vector (Stratagene) using standard techniques (Current Protocols in Molecules Biology, eds. M. Ausubel et al., John Wiley & Sons, New York, 1988). The subcloned PCR products were sequenced by the method of Sanger et al. (1977, Proc. Natl. Acad. Sci. USA 74, 5463–5467) using T7-Polymerase (Boehringer Mannheim).

The CCK-2 PCR fragment was used to screen a human placenta library in lambda ZAP. The longest cDNA insert ~1300 bp was digested with the restriction enzymes EcoRI/Ncol to obtain a 5' end probe of 200 bp. Rescreening of the human placenta library yielded in a cDNA clone which encoded the entire CCK-2 protein (subcloning of positive bacteriophages clones into pBluescript vector was done by the in vivo excision protocol (Stratagene)). The DNA sequence and the deduced aminoacid sequence of CCK-2 is shown in FIG. 3 (SEQ ID NOS:3–4).

7.1.2. Northern Blot Analysis

The 5' located 1260 bp of CCK-2 was subcloned into the pBluescript SK$^+$-vector (pBSK$^+$; Stratagene). For Northern blot analysis, the probe was prepared by labeling the cDNA fragment with α-$^{32}$PdATP using a random hexanucleotide priming kit (United States Biochemical) and purified with Sephadex-G50 column.

7.1.3. In Situ Hybridization

For in situ hybridization, single-stranded antisense DNA probes were prepared as described by Schnürch & Risau (1991 Development 111: 1143–1154). The pBSK$^+$ CCK-2 plasmid was linearized at the 3' end of the cDNA by restriction digest with EcoRI and antisense transcripts were synthesized using SP6 RNA polymerase (Boehringer). The DNA was degraded using DNAase (RNAase-free preparation, Boehringer Mannheim). With the transcripts, random-primed cDNA synthesis with α-$^{35}$S ATP (Amersham) was performed by reverse transcription with MMLV reverse transcriptase (BRL). A high excess of primer was used to obtain small cDNA fragments of about 100 bp in average. Subsequently, the RNA transcripts were partially hydrolyzed in 100 nM NaOH for 20 minutes at 70° C., neutralized with the same amount of HCL, and purified with a Sephadex-G50 column. After ethanol precipitation, probes were dissolved at a final specific activity of 5×10$^5$ cpm. Sense probes for control hybridization were prepared using the same method.

7.1.4. Transient Overexpression of CCK-2 in 293 Cells

The cDNA insert containing the entire open reading frame of CCK-2 was subcloned into a cytomegalovirus promoter-based expression plasmid and semiconfluent human embryonic kidney fibroblast 293 cell line were transfected. Cell lysates from CCK-2-transfected cells were separated on a 7.5% polyacrylamide gel, transferred to nitrocellulose, and probed with the 5E2 monoclonal antibody against antiphosphotyrosine (α PY). Incubation of cells with 1 mM sodium orthovanadate was carried out 90 minutes prior to lysis.

7.2. Results

7.2.1. and Characterization of CCK-2 Clone

An additional member of the MCK-10 receptor tyrosine kinase family was identified using a polymerase chain reaction and cDNA prepared from colonic adenocarcinoma RNA. The nucleotide sequence of the novel receptor, designated CCK-2, is presented in FIGS. 3A, 3B, 3C and 3D (SEQ ID NO:3). Analysis of the CCK-2, nucleotide sequence and encoded amino acid sequence indicated significant homology with MCK-10 throughout the extracellular, transmembrane and intracellular region of the MCK-10 receptor. The regions of homology between CCK-2 and MCK-10 extend into the N-terminus consensus sequence for the discoidin I like family of proteins. (Poole et al. 1981, J. Mol. Biol. 153, 273–289). The homology between CCK-2 and MCK-10-2 is diagramed in FIG. 4A and 4B.

Between the two RTKs, the juxtamembrane region is the region of most extensive sequence divergence. The importance of this region for the signaling capacity of the MCK-10/CCK-2 subclass of RTKs is further emphasized by several structural and functional criteria. CCK-2 displays a serine-rich stretch between amino acids 430 and 470 that includes among other possible phosphorylation sites a potential protein kinase C substrate site at position 433 (EKASRR) (SEQ ID NO:39). While a similar sequence including a serine residue is found at approximately the same location in MCK-10-2 (Ser 448, RRLLSKAERR) (SEQ ID NO:40), the serine content of its JM domain is comparatively lower but instead features a remarkably high number of proline residues. These are arranged in either PXXP (SEQ ID NO:41) or PXXXP (SEQ ID NO:42) repeats, suggesting a random coil structure for this highly hydrophilic region, which is in the likelihood a major domain for interactions with cellular substrates and other regulatory proteins and therefore may be the functional homolog to the C-tail region of the EGF-R, the kinase insertion domain of the PDGF-R, and the auxiliary signal transmission factor IRS-1 of the insulin receptor (for review see Williamson et al., 1994, Biochem J., 297: 249–260). The striking differences between MCK-10 and CCK-2 in this region suggest that determinants within this region define their distinct biological functions. This prediction is supported by the 37 amino acid MCK-10-2 insertion, which includes "signal" motifs for internalization (NPXY) (SEQ ID NO:19), ligand binding modulation (TYAXPXXXPG) (SEQ ID NO:8), and SH3 domain interaction (PXPPXP) (SEQ ID NO:43). This latter motif is very similar to the SH3 binding site of the murine 3BP2 protein (Ren et al., 1993, Science 259: 1157–1161) and matches the most favorable SH3 binding structure proposed by Yu et al. (1994, Cell 76: 933–945) (FIG. 4C). The alternative splicing of this regulatory sequence may define distinct protein interactions and thereby modulate receptor function and ultimately the response of the cell. Moreover, the proline-rich sequences that flank the 37-residue insertion in MCK-10 are distinct from those in the CCK-2 JM domain and, therefore, may play a role in RTK-characteristic function. Similar putative SH3 domain docking sites have previously been found in tyrosine kinases of the non-receptor type such as Fgr. ack, and Fak (FIG. 4C; Naharro et al., 1984, Science, 233: 63–66; Manser et al., 1993, Nature 363: 364–367; Andre & Becker-Andre, 1993, Biochem. Biophys. Res. Comm. 190: 140–147) but are described here for the first time in RTKs.

7.2.2. Northern Blot Analysis: Expression of CCK-2 in Various Human Tissues and Cell Lines CCK-2 expression in human tumor cell lines was investigated using Northern blot analysis. While varying levels of 4.3 Kb MCK-10 mRNA expression were detected in epithelial type tumor cell lines T-470, MDA-MB-231, CaKi-2, Caco-2 and SNW-C2B, the CCK-2 probe hybridized predominantly to multiple RNAs in SK-Mel-2, Wi-26VA4, and Wi-38VA13, which expressed only low levels of MCK-10 mRNA (FIG. 5D).

7.2.3. In Situ Hybridization

For a more detailed expression analysis in situ hybridization on human normal and tumor tissues, were performed using single-stranded antisense CCK-2 DNA fragments. In situ hybridization analysis of human carcinomas of different origin revealed a remarkably distinct pattern of CCK-2 and MCK-10 mRNA expression, as demonstrated by in situ hybridization on serial-sections. Both receptors were expressed in an apparently mutually exclusive manner in different cell types of the same tumor. CCK-2 was predominantly found in all stromal cells, which provide an environment conducive to proliferation, invasion, and even metastasis of epithelial cells, whereas MCK-10 expression was strongly confined to the neoplastic cells themselves (Liotta et al., 1983, Laboratory Investigation 49: 636–649; Iozzo and Cohen, 1993, Experientia 49: 447–455). As shown in FIG. 23A, MCK-10 mRNA was abundant in epithelial tumor cells of a poorly differentiated, grade III, papillary adenocarcinoma of the ovary, whereas CCK-2 gene expression was only detected in stromal cells within the tumor. Hybridization signals of CCK-2 appeared to be more dispersed, in accordance with the fact that cells of the connective tissue, which contain a large amount of extracellular matrix, are more separated in contrast to tumor epithelia, where cells are closely associated. A similar expression pattern was found in a moderately differentiated, grade II, bronchioalveolar adenocarcinoma of the lung (FIG. 23B). Consistent with the hybridization signal distribution in the ovarian carcinoma, MCK-10 mRNA was restricked to epithelial tumor cells, whereas CCK-2 positive hybridization signals were observed only in stromal cells, although at a lower level than in the ovarian carcinoma. These findings parallel the observations of Zerlin et al. (1993, Oncogene 8: 2731–2739), who demonstrated that NEP, the mouse homologue to MCK-10, was abundant in embryonic-proliferating neuroepithelial cells and significantly lower or absent in differentiated cells that had migrated away from proliferating zones. The idea that invading cancer cells may use the same signaling system as neuroepithelial cells during embryogenesis further supports a role for MCK-10 in cell recognition mediated proliferation and migration. In normal epithelial and tumor cells MCK-10 may promote cell adhesion in a hemophilic manner, similar to the Drosophila homologue of Trk, Dtrk (Pulido et al., 1992, EMBO J. 11: 391–404), by binding to the same receptor expressed in adjacent cells or by interacting heterophilically with other molecules involved in cell-cell interaction, such as CCK-2.

7.2.4. Transient Expression of CCK-2 in 293 Cells

Transfection of 293 cells with pCMV CCK-2, yielded a single 126 K Da band which was phosphorylated, even in the absence of orthovanadate, presumably representing the glycosylated CCK-2 receptor protein (FIG. 6C).

In summary, the distinct expression pattern of CCK-2 and MCK-10 suggests that these closely related receptors are involved in interactions between neoplastic epithelial cells and surrounding stroma during tumor progression, and the presence of the discoidin I motif in their extracellular domains indicates that these receptors play an important role in processes involved in cell-cell communications.

8. DEPOSIT OF MICROORGANISMS

The following organisms were deposited with the American Type Culture Collection (ATCC), 12301 Parklawn Drive, Rockville, Md. 20852.

| Strain Designation | Containing | Accession No. |
|---|---|---|
| CCK-2 | pCCK-2 | 69468 |
| MCK-10-1 | pMCK-10-1 | 69464 |
| MCK-10-2 | pMCK-10-2 | 69465 |
| MCK-10-3 | pMCK-10-3 | 69466 |
| MCK-10-4 | pMCK-10-4 | 69467 |

The present invention is not to be limited in scope by the exemplified embodiments or deposited organisms which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description.

---

What is claimed is:

1. A recombinant vector containing a nucleotide sequence that encodes a truncated CCK-2 having an amino acid sequence of SEQ ID NO:4.

2. The recombinant vector of claim 1 in which the vector is a retrovirus vector.

3. An engineered cell line that contains the recombinant DNA vector of claim 1 or 2 and expresses truncated CCK-2.

4. An engineered cell line that contains the recombinant vector of claim 2 and produces infectious retrovirus particles expressing truncated CCK-2.

5. A recombinant truncated CCK-2 receptor protein of SEQ ID NO:4, which lacks one or more amino acid residues in the cytoplasmic domain.

6. An isolated nucleic acid molecule comprising a nucleotide sequence that encodes (a) a polypeptide having the amino acid sequence of SEQ ID NO:4; or (b) a nucleic acid molecule having a nucleotide sequence complementary to the nucleotide sequence of a nucleic acid molecule of (a).

7. An isolated nucleic acid molecule that hybridizes under highly stringent conditions to the nucleic acid molecule of claim 6 and encodes a naturally occurring CCK-2 protein.

8. An isolated nucleic acid molecule comprising a nucleotide sequence that hybridizes under stringent conditions to the nucleic acid of claim 6 and encodes a naturally occurring CCK-2 protein, or an extracellular or kinase domain thereof, linked uninterrupted by stop codons to a nucleotide sequence that encodes a heterologous protein or peptide.

9. An isolated nucleic acid molecule comprising the nucleotide sequence of SEQ ID NO:3.

10. A nucleic acid molecule encoding (a) a deletion mutant of SEQ ID NO:4 missing one or more amino acids residues of the extracellular, transmembrane, or cytoplasmic domain; or (b) a nucleic acid molecule having a nucleotide sequence complementary to the nucleotide sequence of a nucleic acid molecule of (a).

11. The nucleic acid molecule of claim 10 wherein the missing amino acid residue(s) is in the tyrosine kinase region of the cytoplasmic domain.

12. The nucleic acid molecule of claim 10 wherein the missing amino acid residue(s) is in the Discoidin I-like region of the extracellular domain.

13. A recombinant vector containing the nucleic acid molecule of claim 10 wherein the vector is a retrovirus vector.

14. A genetically engineered cell line that contains the recombinant vector of claim 13.

15. The engineered cell line of claim 14 that produces infectious retrovirus particles.

16. A nucleic acid molecule encoding (a) a polypeptide corresponding to the extracellular, transmembrane, or cytoplasmic domain of SEQ ID NO:4; or (b) a nucleic acid molecule having a nucleotide sequence complementary to the nucleotide sequence of a nucleic acid molecule of (a).

17. The nucleic acid molecule of claim 16 wherein the encoded polypeptide corresponds to the tyrosine kinase region of the cytoplasmic domain.

18. The nucleic acid molecule of claim 16 wherein the encoded polypeptide corresponds to the Discoidin I-like region of the extracellular domain.

19. A recombinant vector containing the nucleic acid molecule of claim 6, 7, 9, 8, 10 or 16.

20. An expression vector containing the nucleic acid molecule of claim 6, 7, 9, 8, 10 or 16 operatively associated with a regulatory nucleotide sequence containing transcriptional and translational regulatory information that controls expression of the nucleic acid molecule in a host cell.

21. A genetically engineered host cell containing the nucleic acid molecule of claim 6, 7, 9, 8, 10 or 16.

22. A genetically engineered host cell containing the nucleic acid molecule of claim 6, 7, 9, 8, 10 or 16 operatively associated with a regulatory nucleotide sequence containing transcriptional and translational regulatory information that controls expression of the nucleic acid molecule in a host cell.

23. A method for producing recombinant CCK-2, comprising:

(a) culturing a host cell transformed with the expression vector of claim 20 and which expresses the CCK-2; and (b) recovering the CCK-2 gene product from the cell culture.

24. The genetically engineered host cell of claim 22 in which the host cell is prokaryotic.

25. The genetically engineered host cell of claim 22 in which the host cell is eukaryotic.

* * * * *

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
        ( A ) LENGTH: 3962 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 321..3077

( x i ) SEQUENCE DESCRIPTION: SEQ ID NO:1:

```
CGGGCCTGAG ACTGGGGTGA CTGGGACCTA AGAGAATCCT GAGCTGGAGG CCCCCGACAG         60

CTGCTCTCGG GAGCCGCCTC CCGACACCCG AGCCCCGCCG GCGCCTCCCG CTCCCGGCTC        120

CCGGCTCCTG GCTCCCTCCG CCTCCCCCGC CCCTCGCCCC GCCGCCGAAG AGGCCCCGCT        180

CCCGGGTCGG ACGCCTGGGT CTGCCGGGAA GAGCGATGAG AGGTGTCTGA AGGTGGCTAT        240

TCACTGAGCG ATGGGGTTGG ACTTGAAGGA ATGCCAAGAG ATGCTGCCCC CACCCCCTTA        300

GGCCCGAGGG ATCAGGAGCT ATG GGA CCA GAG GCC CTG TCA TCT TTA CTG            350
                        Met Gly Pro Glu Ala Leu Ser Ser Leu Leu
                         1               5                  10

CTG CTG CTC TTG GTG GCA AGT GGA GAT GCT GAC ATG AAG GGA CAT TTT          398
Leu Leu Leu Leu Val Ala Ser Gly Asp Ala Asp Met Lys Gly His Phe
             15                  20                  25

GAT CCT GCC AAG TGC CGC TAT GCC CTG GGC ATG CAG GAC CGG ACC ATC          446
Asp Pro Ala Lys Cys Arg Tyr Ala Leu Gly Met Gln Asp Arg Thr Ile
             30                  35                  40

CCA GAC AGT GAC ATC TCT GCT TCC AGC TCC TGG TCA GAT TCC ACT GCC          494
Pro Asp Ser Asp Ile Ser Ala Ser Ser Ser Trp Ser Asp Ser Thr Ala
             45                  50                  55

GCC CGC CAC AGC AGG TTG GAG AGC AGT GAC GGG GAT GGG GCC TGG TGC          542
Ala Arg His Ser Arg Leu Glu Ser Ser Asp Gly Asp Gly Ala Trp Cys
         60                  65                  70

CCC GCA GGG TCG GTG TTT CCC AAG GAG GAG GAG TAC TTG CAG GTG GAT          590
Pro Ala Gly Ser Val Phe Pro Lys Glu Glu Glu Tyr Leu Gln Val Asp
 75                  80                  85                  90

CTA CAA CGA CTC CAC CTG GTG GCT CTG GTG GGC ACC CAG GGA CGG CAT          638
```

| | | | | | | | | | | | | | | | | |
|---|---|---|---|---|---|---|---|---|---|---|---|---|---|---|---|---|
| Leu | Gln | Arg | Leu | His 95 | Leu | Val | Ala | Leu 100 | Val | Gly | Thr | Gln | Gly 105 | Arg | His | |
| GCC | GGG | GGC | CTG | GGC | AAG | GAG | TTC | TCC | CGG | AGC | TAC | CGG | CTG | CGT | TAC | 686 |
| Ala | Gly | Gly | Leu 110 | Gly | Lys | Glu | Phe 115 | Ser | Arg | Ser | Tyr | Arg 120 | Leu | Arg | Tyr | |
| TCC | CGG | GAT | GGT | CGC | CGC | TGG | ATG | GGC | TGG | AAG | GAC | CGC | TGG | GGT | CAG | 734 |
| Ser | Arg | Asp 125 | Gly | Arg | Arg | Trp | Met 130 | Gly | Trp | Lys | Asp | Arg 135 | Trp | Gly | Gln | |
| GAG | GTG | ATC | TCA | GGC | AAT | GAG | GAC | CCT | GAG | GGA | GTG | GTG | CTG | AAG | GAC | 782 |
| Glu | Val | Ile | Ser 140 | Gly | Asn | Glu | Asp | Pro 145 | Glu | Gly | Val | Val 150 | Leu | Lys | Asp | |
| CTT | GGG | CCC | CCC | ATG | GTT | GCC | CGA | CTG | GTT | CGC | TTC | TAC | CCC | CGG | GCT | 830 |
| Leu 155 | Gly | Pro | Pro | Met | Val 160 | Ala | Arg | Leu | Val | Arg 165 | Phe | Tyr | Pro | Arg | Ala 170 | |
| GAC | CGG | GTC | ATG | AGT | GTC | TGT | CTG | CGG | GTA | GAG | CTC | TAT | GGC | TGC | CTC | 878 |
| Asp | Arg | Val | Met | Ser 175 | Val | Cys | Leu | Arg | Val 180 | Glu | Leu | Tyr | Gly | Cys 185 | Leu | |
| TGG | AGG | GAT | GGA | CTC | CTG | TCT | TAC | ACC | GCC | CCT | GTG | GGG | CAG | ACA | ATG | 926 |
| Trp | Arg | Asp | Gly 190 | Leu | Leu | Ser | Tyr | Thr 195 | Ala | Pro | Val | Gly | Gln 200 | Thr | Met | |
| TAT | TTA | TCT | GAG | GCC | GTG | TAC | CTC | AAC | GAC | TCC | ACC | TAT | GAC | GGA | CAT | 974 |
| Tyr | Leu | Ser 205 | Glu | Ala | Val | Tyr | Leu 210 | Asn | Asp | Ser | Thr | Tyr 215 | Asp | Gly | His | |
| ACC | GTG | GGC | GGA | CTG | CAG | TAT | GGG | GGT | CTG | GGC | CAG | CTG | GCA | GAT | GGT | 1022 |
| Thr | Val 220 | Gly | Gly | Leu | Gln | Tyr 225 | Gly | Gly | Leu | Gly | Gln 230 | Leu | Ala | Asp | Gly | |
| GTG | GTG | GGG | CTG | GAT | GAC | TTT | AGG | AAG | AGT | CAG | GAG | CTG | CGG | GTC | TGG | 1070 |
| Val 235 | Val | Gly | Leu | Asp | Asp 240 | Phe | Arg | Lys | Ser | Gln 245 | Glu | Leu | Arg | Val | Trp 250 | |
| CCA | GGC | TAT | GAC | TAT | GTG | GGA | TGG | AGC | AAC | CAC | AGC | TTC | TCC | AGT | GGC | 1118 |
| Pro | Gly | Tyr | Asp | Tyr 255 | Val | Gly | Trp | Ser | Asn 260 | His | Ser | Phe | Ser | Ser 265 | Gly | |
| TAT | GTG | GAG | ATG | GAG | TTT | GAG | TTT | GAC | CGG | CTG | AGG | GCC | TTC | CAG | GCT | 1166 |
| Tyr | Val | Glu | Met 270 | Glu | Phe | Glu | Phe | Asp 275 | Arg | Leu | Arg | Ala | Phe 280 | Gln | Ala | |
| ATG | CAG | GTC | CAC | TGT | AAC | AAC | ATG | CAC | ACG | CTG | GGA | GCC | CGT | CTG | CCT | 1214 |
| Met | Gln | Val 285 | His | Cys | Asn | Asn | Met 290 | His | Thr | Leu | Gly | Ala 295 | Arg | Leu | Pro | |
| GGC | GGG | GTG | GAA | TGT | CGC | TTC | CGG | CGT | GGC | CCT | GCC | ATG | GCC | TGG | GAG | 1262 |
| Gly | Gly 300 | Val | Glu | Cys | Arg | Phe 305 | Arg | Arg | Gly | Pro | Ala 310 | Met | Ala | Trp | Glu | |
| GGG | GAG | CCC | ATG | CGC | CAC | AAC | CTA | GGG | GGC | AAC | CTG | GGG | GAC | CCC | AGA | 1310 |
| Gly 315 | Glu | Pro | Met | Arg 320 | His | Asn | Leu | Gly | Gly 325 | Asn | Leu | Gly | Asp | Pro 330 | Arg | |
| GCC | CGG | GCT | GTC | TCA | GTG | CCC | CTT | GGC | GGC | CGT | GTG | GCT | CGC | TTT | CTG | 1358 |
| Ala | Arg | Ala | Val | Ser 335 | Val | Pro | Leu | Gly | Gly 340 | Arg | Val | Ala | Arg | Phe 345 | Leu | |
| CAG | TGC | CGC | TTC | CTC | TTT | GCG | GGG | CCC | TGG | TTA | CTC | TTC | AGC | GAA | ATC | 1406 |
| Gln | Cys | Arg | Phe 350 | Leu | Phe | Ala | Gly | Pro 355 | Trp | Leu | Leu | Phe | Ser 360 | Glu | Ile | |
| TCC | TTC | ATC | TCT | GAT | GTG | GTG | AAC | AAT | TCC | TCT | CCG | GCA | CTG | GGA | GGC | 1454 |
| Ser | Phe | Ile 365 | Ser | Asp | Val | Val | Asn 370 | Asn | Ser | Ser | Pro | Ala 375 | Leu | Gly | Gly | |
| ACC | TTC | CCG | CCA | GCC | CCC | TGG | TGG | CCG | CCT | GGC | CCA | CCT | CCC | ACC | AAC | 1502 |
| Thr | Phe | Pro 380 | Pro | Ala | Pro | Pro 385 | Trp | Trp | Pro | Pro | Gly 390 | Pro | Pro | Pro | Thr | Asn | |
| TTC | AGC | AGC | TTG | GAG | CTG | GAG | CCC | AGA | GGC | CAG | CAG | CCC | GTG | GCC | AAG | 1550 |
| Phe 395 | Ser | Ser | Leu | Glu | Leu 400 | Glu | Pro | Arg | Gly | Gln 405 | Gln | Pro | Val | Ala | Lys 410 | |
| GCC | GAG | GGG | AGC | CCG | ACC | GCC | ATC | CTC | ATC | GGC | TGC | CTG | GTG | GCC | ATC | 1598 |

|  |  |
|---|---|
| Ala Glu Gly Ser Pro Thr Ala Ile Leu Ile Gly Cys Leu Val Ala Ile<br>415                                   420                         425 |  |
| ATC CTG CTC CTG CTG CTC ATC ATT GCC CTC ATG CTC TGG CGG CTG CAC<br>Ile Leu Leu Leu Leu Leu Ile Ile Ala Leu Met Leu Trp Arg Leu His<br>                  430                             435                          440 | 1646 |
| TGG CGC AGG CTC CTC AGC AAG GCT GAA CGG AGG GTG TTG GAA GAG GAG<br>Trp Arg Arg Leu Leu Ser Lys Ala Glu Arg Arg Val Leu Glu Glu Glu<br>            445                             450                          455 | 1694 |
| CTG ACG GTT CAC CTC TCT GTC CCT GGG GAC ACT ATC CTC ATC AAC AAC<br>Leu Thr Val His Leu Ser Val Pro Gly Asp Thr Ile Leu Ile Asn Asn<br>460                                  465                          470 | 1742 |
| CGC CCA GGT CCT AGA GAG CCA CCC CCG TAC CAG GAG CCC CGG CCT CGT<br>Arg Pro Gly Pro Arg Glu Pro Pro Pro Tyr Gln Glu Pro Arg Pro Arg<br>475                                  480                          485                          490 | 1790 |
| GGG AAT CCG CCC CAC TCC GCT CCC TGT GTC CCC AAT GGC TCT GCG TTG<br>Gly Asn Pro Pro His Ser Ala Pro Cys Val Pro Asn Gly Ser Ala Leu<br>                          495                          500                          505 | 1838 |
| CTG CTC TCC AAT CCA GCC TAC CGC CTC CTT CTG GCC ACT TAC GCC CGT<br>Leu Leu Ser Asn Pro Ala Tyr Arg Leu Leu Leu Ala Thr Tyr Ala Arg<br>                510                             515                          520 | 1886 |
| CCC CCT CGA GGC CCG GGC CCC CCC ACA CCC GCC TGG GCC AAA CCC ACC<br>Pro Pro Arg Gly Pro Gly Pro Pro Thr Pro Ala Trp Ala Lys Pro Thr<br>            525                             530                          535 | 1934 |
| AAC ACC CAG GCC TAC AGT GGG GAC TAT ATG GAG CCT GAG AAG CCA GGC<br>Asn Thr Gln Ala Tyr Ser Gly Asp Tyr Met Glu Pro Glu Lys Pro Gly<br>540                                  545                          550 | 1982 |
| GCC CCG CTT CTG CCC CCA CCT CCC CAG AAC AGC GTC CCC CAT TAT GCC<br>Ala Pro Leu Leu Pro Pro Pro Pro Gln Asn Ser Val Pro His Tyr Ala<br>555                                  560                          565                          570 | 2030 |
| GAG GCT GAC ATT GTT ACC CTG CAG GGC GTC ACC GGG GGC AAC ACC TAT<br>Glu Ala Asp Ile Val Thr Leu Gln Gly Val Thr Gly Gly Asn Thr Tyr<br>                        575                          580                          585 | 2078 |
| GCT GTG CCT GCA CTG CCC CCA GGG GCA GTC GGG GAT GGG CCC CCC AGA<br>Ala Val Pro Ala Leu Pro Pro Gly Ala Val Gly Asp Gly Pro Pro Arg<br>              590                            595                            600 | 2126 |
| GTG GAT TTC CCT CGA TCT CGA CTC CGC TTC AAG GAG AAG CTT GGC GAG<br>Val Asp Phe Pro Arg Ser Arg Leu Arg Phe Lys Glu Lys Leu Gly Glu<br>            605                             610                          615 | 2174 |
| GGC CAG TTT GGG GAG GTG CAC CTG TGT GAG GTC GAC AGC CCT CAA GAT<br>Gly Gln Phe Gly Glu Val His Leu Cys Glu Val Asp Ser Pro Gln Asp<br>              620                            625                          630 | 2222 |
| CTG GTC AGT CTT GAT TTC CCC CTT AAT GTG CGT AAG GGA CAC CCT TTG<br>Leu Val Ser Leu Asp Phe Pro Leu Asn Val Arg Lys Gly His Pro Leu<br>635                                  640                          645                          650 | 2270 |
| CTG GTA GCT GTC AAG ATC TTA CGG CCA GAT GCC ACC AAG AAT GCC AGC<br>Leu Val Ala Val Lys Ile Leu Arg Pro Asp Ala Thr Lys Asn Ala Ser<br>                        655                          660                          665 | 2318 |
| TTC TCC TTG TTC TCC AGG AAT GAT TTC CTG AAA GAG GTG AAG ATC ATG<br>Phe Ser Leu Phe Ser Arg Asn Asp Phe Leu Lys Glu Val Lys Ile Met<br>              670                            675                          680 | 2366 |
| TCG AGG CTC AAG GAC CCC AAC ATC ATT CGG CTG CTG GGC GTG TGT GTG<br>Ser Arg Leu Lys Asp Pro Asn Ile Ile Arg Leu Leu Gly Val Cys Val<br>                685                             690                          695 | 2414 |
| CAG GAC GAC CCC CTC TGC ATG ATT ACT GAC TAC ATG GAG AAC GGC GAC<br>Gln Asp Asp Pro Leu Cys Met Ile Thr Asp Tyr Met Glu Asn Gly Asp<br>            700                             705                          710 | 2462 |
| CTC AAC CAG TTC CTC AGT GCC CAC CAG CTG GAG GAC AAG GCA GCC GAG<br>Leu Asn Gln Phe Leu Ser Ala His Gln Leu Glu Asp Lys Ala Ala Glu<br>715                                  720                          725                          730 | 2510 |
| GGG GCC CCT GGG GAC GGG CAG GCT GCG CAG GGG CCC ACC ATC AGC TAC | 2558 |

```
Gly Ala Pro Gly Asp Gly Gln Ala Ala Gln Gly Pro Thr Ile Ser Tyr
            735             740                 745

CCA ATG CTG CTG CAT GTG GCA GCC CAG ATC GCC TCC GGC ATG CGC TAT    2606
Pro Met Leu Leu His Val Ala Ala Gln Ile Ala Ser Gly Met Arg Tyr
            750             755                 760

CTG GCC ACA CTC AAC TTT GTA CAT CGG GAC CTG GCC ACG CGG AAC TGC    2654
Leu Ala Thr Leu Asn Phe Val His Arg Asp Leu Ala Thr Arg Asn Cys
            765             770                 775

CTA GTT GGG GAA AAT TTC ACC ATC AAA ATC GCA GAC TTT GGC ATG AGC    2702
Leu Val Gly Glu Asn Phe Thr Ile Lys Ile Ala Asp Phe Gly Met Ser
            780             785                 790

CGG AAC CTC TAT GCT GGG GAC TAT TAC CGT GTG CAG GGC CGG GCA GTG    2750
Arg Asn Leu Tyr Ala Gly Asp Tyr Tyr Arg Val Gln Gly Arg Ala Val
795             800             805                 810

CTG CCC ATC CGC TGG ATG GCC TGG GAG TGC ATC CTC ATG GGG AAG TTC    2798
Leu Pro Ile Arg Trp Met Ala Trp Glu Cys Ile Leu Met Gly Lys Phe
            815             820                 825

ACG ACT GCG AGT GAC GTG TGG GCC TTT GGT GTG ACC CTG TGG GAG GTG    2846
Thr Thr Ala Ser Asp Val Trp Ala Phe Gly Val Thr Leu Trp Glu Val
            830             835                 840

CTG ATG CTC TGT AGG GCC CAG CCC TTT GGG CAG CTC ACC GAC GAG CAG    2894
Leu Met Leu Cys Arg Ala Gln Pro Phe Gly Gln Leu Thr Asp Glu Gln
            845             850                 855

GTC ATC GAG AAC GCG GGG GAG TTC TTC CGG GAC CAG GGC CGG CAG GTG    2942
Val Ile Glu Asn Ala Gly Glu Phe Phe Arg Asp Gln Gly Arg Gln Val
            860             865                 870

TAC CTG TCC CGG CCG CCT GCC TGC CCG CAG GGC CTA TAT GAG CTG ATG    2990
Tyr Leu Ser Arg Pro Pro Ala Cys Pro Gln Gly Leu Tyr Glu Leu Met
875             880             885                 890

CTT CGG TGC TGG AGC CGG GAG TCT GAG CAG CGA CCA CCC TTT TCC CAG    3038
Leu Arg Cys Trp Ser Arg Glu Ser Glu Gln Arg Pro Pro Phe Ser Gln
            895             900                 905

CTG CAT CGG TTC CTG GCA GAG GAT GCA CTC AAC ACG GTG TGAATCACAC     3087
Leu His Arg Phe Leu Ala Glu Asp Ala Leu Asn Thr Val
            910             915

ATCCAGCTGC CCCTCCCTCA GGGAGTGATC CAGGGGAAGC CAGTGACACT AAAACAAGAG  3147
GACACAATGG CACCTCTGCC CTTCCCCTCC CGACAGCCCA TCACCTCTAA TAGAGGCAGT  3207
GAGACTGCAG GTGGGCTGGG CCCACCCAGG GAGCTGATGC CCCTTCTCCC CTTCCTGGAC  3267
ACACTCTCAT GTCCCCTTCC TGTTCTTCCT TCCTAGAAGC CCCTGTCGCC CACCCAGCTG  3327
GTCCTGTGGA TGGGATCCTC TCCACCCTCC TCTAGCCATC CCTTGGGGAA GGGTGGGGAG  3387
AAATATAGGA TAGACACTGG ACATGGCCCA TTGGAGCACC TGGGCCCCAC TGGACAACAC  3447
TGATTCCTGG AGAGGTGGCT GCGCCCCAGC TTCTCTCTCC CTGTCACACA CTGGACCCCA  3507
CTGGCTGAGA ATCTGGGGGT GAGGAGGACA AGAAGGAGAG GAAAATGTTT CCTTGTGCCT  3567
GCTCCTGTAC TTGTCCTCAG CTTGGGCTTC TTCCTCCTCC ATCACCTGAA ACACTGGACC  3627
TGGGGGTAGC CCGCCCCAG CCCTCAGTCA CCCCACTTC CCACTTGCAG TCTTGTAGCT   3687
AGAACTTCTC TAAGCCTATA CGTTTCTGTG GAGTAAATAT TGGGATTGGG GGGAAAGAGG  3747
GAGCAACGGC CCATAGCCTT GGGGTTGGAC ATCTCTAGTG TAGCTGCCAC ATTGATTTTT  3807
CTATAATCAC TTGGGGTTTG TACATTTTTG GGGGAGAGA CACAGATTTT TACACTAATA   3867
TATGGACCTA GCTTGAGGCA ATTTTAATCC CCTGCACTAG GCAGGTAATA ATAAAGGTTG  3927
AGTTTTCCAC AAAAAAAAAA AAAAAACCGG AATTC                             3962
```

( 2 ) INFORMATION FOR SEQ ID NO:2:

(i) SEQUENCE CHARACTERISTICS:
  (A) LENGTH: 919 amino acids
  (B) TYPE: amino acid
  (D) TOPOLOGY: unknown (ii) MOLECULE TYPE: protein (xi) SEQUENCE DESCRIPTION: SEQ ID NO:2:

| Met | Gly | Pro | Glu | Ala | Leu | Ser | Ser | Leu | Leu | Leu | Leu | Leu | Leu | Val | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Gly | Asp | Ala | Asp | Met | Lys | Gly | His | Phe | Asp | Pro | Ala | Lys | Cys | Arg |
|     |     | 20  |     |     |     |     | 25  |     |     |     |     | 30  |     |     |     |
| Tyr | Ala | Leu | Gly | Met | Gln | Asp | Arg | Thr | Ile | Pro | Asp | Ser | Asp | Ile | Ser |
|     |     | 35  |     |     |     |     | 40  |     |     |     |     | 45  |     |     |     |
| Ala | Ser | Ser | Ser | Trp | Ser | Asp | Ser | Thr | Ala | Ala | Arg | His | Ser | Arg | Leu |
|     | 50  |     |     |     |     | 55  |     |     |     |     | 60  |     |     |     |     |
| Glu | Ser | Ser | Asp | Gly | Asp | Gly | Ala | Trp | Cys | Pro | Ala | Gly | Ser | Val | Phe |
| 65  |     |     |     |     | 70  |     |     |     | 75  |     |     |     |     |     | 80  |
| Pro | Lys | Glu | Glu | Glu | Tyr | Leu | Gln | Val | Asp | Leu | Gln | Arg | Leu | His | Leu |
|     |     |     |     | 85  |     |     |     |     | 90  |     |     |     |     | 95  |     |
| Val | Ala | Leu | Val | Gly | Thr | Gln | Gly | Arg | His | Ala | Gly | Gly | Leu | Gly | Lys |
|     |     |     | 100 |     |     |     |     |     | 105 |     |     |     |     | 110 |     |
| Glu | Phe | Ser | Arg | Ser | Tyr | Arg | Leu | Arg | Tyr | Ser | Arg | Asp | Gly | Arg | Arg |
|     |     |     | 115 |     |     |     |     | 120 |     |     |     |     | 125 |     |     |
| Trp | Met | Gly | Trp | Lys | Asp | Arg | Trp | Gly | Gln | Glu | Val | Ile | Ser | Gly | Asn |
|     | 130 |     |     |     |     | 135 |     |     |     |     | 140 |     |     |     |     |
| Glu | Asp | Pro | Glu | Gly | Val | Val | Leu | Lys | Asp | Leu | Gly | Pro | Pro | Met | Val |
| 145 |     |     |     |     | 150 |     |     |     |     | 155 |     |     |     |     | 160 |
| Ala | Arg | Leu | Val | Arg | Phe | Tyr | Pro | Arg | Ala | Asp | Arg | Val | Met | Ser | Val |
|     |     |     |     | 165 |     |     |     |     | 170 |     |     |     |     | 175 |     |
| Cys | Leu | Arg | Val | Glu | Leu | Tyr | Gly | Cys | Leu | Trp | Arg | Asp | Gly | Leu | Leu |
|     |     |     | 180 |     |     |     |     | 185 |     |     |     |     | 190 |     |     |
| Ser | Tyr | Thr | Ala | Pro | Val | Gly | Gln | Thr | Met | Tyr | Leu | Ser | Glu | Ala | Val |
|     |     | 195 |     |     |     |     | 200 |     |     |     |     | 205 |     |     |     |
| Tyr | Leu | Asn | Asp | Ser | Thr | Tyr | Asp | Gly | His | Thr | Val | Gly | Gly | Leu | Gln |
|     | 210 |     |     |     |     | 215 |     |     |     |     | 220 |     |     |     |     |
| Tyr | Gly | Gly | Leu | Gly | Gln | Leu | Ala | Asp | Gly | Val | Val | Gly | Leu | Asp | Asp |
| 225 |     |     |     |     | 230 |     |     |     |     | 235 |     |     |     |     | 240 |
| Phe | Arg | Lys | Ser | Gln | Glu | Leu | Arg | Val | Trp | Pro | Gly | Tyr | Asp | Tyr | Val |
|     |     |     |     | 245 |     |     |     |     | 250 |     |     |     |     | 255 |     |
| Gly | Trp | Ser | Asn | His | Ser | Phe | Ser | Ser | Gly | Tyr | Val | Glu | Met | Glu | Phe |
|     |     |     | 260 |     |     |     |     | 265 |     |     |     |     | 270 |     |     |
| Glu | Phe | Asp | Arg | Leu | Arg | Ala | Phe | Gln | Ala | Met | Gln | Val | His | Cys | Asn |
|     |     | 275 |     |     |     |     | 280 |     |     |     |     | 285 |     |     |     |
| Asn | Met | His | Thr | Leu | Gly | Ala | Arg | Leu | Pro | Gly | Gly | Val | Glu | Cys | Arg |
|     | 290 |     |     |     |     | 295 |     |     |     |     | 300 |     |     |     |     |
| Phe | Arg | Arg | Gly | Pro | Ala | Met | Ala | Trp | Glu | Gly | Glu | Pro | Met | Arg | His |
| 305 |     |     |     |     | 310 |     |     |     |     | 315 |     |     |     |     | 320 |
| Asn | Leu | Gly | Gly | Asn | Leu | Gly | Asp | Pro | Arg | Ala | Arg | Ala | Val | Ser | Val |
|     |     |     |     | 325 |     |     |     |     | 330 |     |     |     |     | 335 |     |
| Pro | Leu | Gly | Gly | Arg | Val | Ala | Arg | Phe | Leu | Gln | Cys | Arg | Phe | Leu | Phe |
|     |     |     | 340 |     |     |     |     | 345 |     |     |     |     | 350 |     |     |
| Ala | Gly | Pro | Trp | Leu | Leu | Phe | Ser | Glu | Ile | Ser | Phe | Ile | Ser | Asp | Val |
|     |     | 355 |     |     |     |     | 360 |     |     |     |     | 365 |     |     |     |
| Val | Asn | Asn | Ser | Ser | Pro | Ala | Leu | Gly | Gly | Thr | Phe | Pro | Pro | Ala | Pro |
|     | 370 |     |     |     |     | 375 |     |     |     |     | 380 |     |     |     |     |

-continued

```
Trp Trp Pro Pro Gly Pro Pro Pro Thr Asn Phe Ser Ser Leu Glu Leu
385             390             395                         400

Glu Pro Arg Gly Gln Gln Pro Val Ala Lys Ala Glu Gly Ser Pro Thr
                405             410                     415

Ala Ile Leu Ile Gly Cys Leu Val Ala Ile Ile Leu Leu Leu Leu Leu
            420             425                     430

Ile Ile Ala Leu Met Leu Trp Arg Leu His Trp Arg Arg Leu Leu Ser
        435             440             445

Lys Ala Glu Arg Arg Val Leu Glu Glu Glu Leu Thr Val His Leu Ser
    450             455             460

Val Pro Gly Asp Thr Ile Leu Ile Asn Asn Arg Pro Gly Pro Arg Glu
465             470             475             480

Pro Pro Pro Tyr Gln Glu Pro Arg Pro Arg Gly Asn Pro Pro His Ser
            485             490             495

Ala Pro Cys Val Pro Asn Gly Ser Ala Leu Leu Leu Ser Asn Pro Ala
            500             505             510

Tyr Arg Leu Leu Leu Ala Thr Tyr Ala Arg Pro Pro Arg Gly Pro Gly
        515             520             525

Pro Pro Thr Pro Ala Trp Ala Lys Pro Thr Asn Thr Gln Ala Tyr Ser
530             535             540

Gly Asp Tyr Met Glu Pro Glu Lys Pro Gly Ala Pro Leu Leu Pro Pro
545             550             555             560

Pro Pro Gln Asn Ser Val Pro His Tyr Ala Glu Ala Asp Ile Val Thr
            565             570             575

Leu Gln Gly Val Thr Gly Gly Asn Thr Tyr Ala Val Pro Ala Leu Pro
            580             585             590

Pro Gly Ala Val Gly Asp Gly Pro Arg Val Asp Phe Pro Arg Ser
            595             600             605

Arg Leu Arg Phe Lys Glu Lys Leu Gly Glu Gly Gln Phe Gly Glu Val
610             615             620

His Leu Cys Glu Val Asp Ser Pro Gln Asp Leu Val Ser Leu Asp Phe
625             630             635             640

Pro Leu Asn Val Arg Lys Gly His Pro Leu Leu Val Ala Val Lys Ile
            645             650             655

Leu Arg Pro Asp Ala Thr Lys Asn Ala Ser Phe Ser Leu Phe Ser Arg
            660             665             670

Asn Asp Phe Leu Lys Glu Val Lys Ile Met Ser Arg Leu Lys Asp Pro
            675             680             685

Asn Ile Ile Arg Leu Leu Gly Val Cys Val Gln Asp Asp Pro Leu Cys
690             695             700

Met Ile Thr Asp Tyr Met Glu Asn Gly Asp Leu Asn Gln Phe Leu Ser
705             710             715             720

Ala His Gln Leu Glu Asp Lys Ala Ala Glu Gly Ala Pro Gly Asp Gly
            725             730             735

Gln Ala Ala Gln Gly Pro Thr Ile Ser Tyr Pro Met Leu Leu His Val
            740             745             750

Ala Ala Gln Ile Ala Ser Gly Met Arg Tyr Leu Ala Thr Leu Asn Phe
        755             760             765

Val His Arg Asp Leu Ala Thr Arg Asn Cys Leu Val Gly Glu Asn Phe
770             775             780

Thr Ile Lys Ile Ala Asp Phe Gly Met Ser Arg Asn Leu Tyr Ala Gly
785             790             795             800

Asp Tyr Tyr Arg Val Gln Gly Arg Ala Val Leu Pro Ile Arg Trp Met
```

| | | | | 805 | | | | | 810 | | | | | 815 |
|---|---|---|---|---|---|---|---|---|---|---|---|---|---|---|
| Ala | Trp | Glu | Cys<br>820 | Ile | Leu | Met | Gly | Lys<br>825 | Phe | Thr | Thr | Ala | Ser<br>830 | Asp | Val |
| Trp | Ala | Phe<br>835 | Gly | Val | Thr | Leu | Trp<br>840 | Glu | Val | Leu | Met | Leu<br>845 | Cys | Arg | Ala |
| Gln | Pro<br>850 | Phe | Gly | Gln | Leu | Thr<br>855 | Asp | Glu | Gln | Val | Ile<br>860 | Glu | Asn | Ala | Gly |
| Glu<br>865 | Phe | Phe | Arg | Asp | Gln<br>870 | Gly | Arg | Gln | Val | Tyr<br>875 | Leu | Ser | Arg | Pro | Pro<br>880 |
| Ala | Cys | Pro | Gln | Gly<br>885 | Leu | Tyr | Glu | Leu | Met<br>890 | Leu | Arg | Cys | Trp | Ser<br>895 | Arg |
| Glu | Ser | Glu | Gln<br>900 | Arg | Pro | Pro | Phe | Ser<br>905 | Gln | Leu | His | Arg | Phe<br>910 | Leu | Ala |
| Glu | Asp | Ala<br>915 | Leu | Asn | Thr | Val | | | | | | | | | |

( 2 ) INFORMATION FOR SEQ ID NO:3:

( i ) SEQUENCE CHARACTERISTICS:
        ( A ) LENGTH: 3157 base pairs
        ( B ) TYPE: nucleic acid
        ( C ) STRANDEDNESS: both
        ( D ) TOPOLOGY: unknown ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 370..2934

( x i ) SEQUENCE DESCRIPTION: SEQ ID NO:3:

| | | | | | |
|---|---|---|---|---|---|
| GCACGAGCGG | CACGAGTCCA | TGATCTCTTT | CCATCCTCCC | TTTCCTGTTT | GCTCACTTCT | 60 |
| TTTCTTGCTC | ATCTTGGAGA | CTGTGCAATC | CCAGATTAAC | TACAAACAGA | AAGAGCTGG | 120 |
| TGATAGCTCC | AGAGCTCAGA | GAAAGGAGGT | CTCTTTACAA | GAAGTCTGGC | TCTCAAAGCC | 180 |
| TCCATCAAGG | GAGACCTACA | AGTTGCCTGG | GGTTCAGTGC | TCTAGAAAGT | TCCAAGGTTT | 240 |
| GTGGCTTGAA | TTATTCTAAA | GAAGCTGAAA | TAATTGAAGA | GAAGCAGAGG | CCAGCTGTTT | 300 |
| TTGAGGATCC | TGCTCCACAG | AGAATGCTCT | GCACCCGTTG | ATACTCCAGT | TCCAACACCA | 360 |

| TCTTCTGAG | ATG<br>Met<br>1 | ATC<br>Ile | CTG<br>Leu | ATT<br>Ile | CCC<br>Pro<br>5 | AGA<br>Arg | ATG<br>Met | CTC<br>Leu | TTG<br>Leu | GTG<br>Val<br>10 | CTG<br>Leu | TTC<br>Phe | CTG<br>Leu | 408 |
|---|---|---|---|---|---|---|---|---|---|---|---|---|---|---|
| CTG<br>Leu | CTG<br>Leu<br>15 | CCT<br>Pro | ATC<br>Ile | TTG<br>Leu | AGT<br>Ser | TCT<br>Ser<br>20 | GCA<br>Ala | AAA<br>Lys | GCT<br>Ala | CAG<br>Gln | GTT<br>Val<br>25 | AAT<br>Asn | CCA<br>Pro | GCT<br>Ala | ATA<br>Ile | 456 |
| TGC<br>Cys<br>30 | CGC<br>Arg | TAT<br>Tyr | CCT<br>Pro | CTG<br>Leu | GGC<br>Gly<br>35 | ATG<br>Met | TCA<br>Ser | GGA<br>Gly | GGC<br>Gly | CAG<br>Gln<br>40 | ATT<br>Ile | CCA<br>Pro | GAT<br>Asp | GAG<br>Glu | GAC<br>Asp<br>45 | 504 |
| ATC<br>Ile | ACA<br>Thr | GCT<br>Ala | TCC<br>Ser | AGT<br>Ser<br>50 | CAG<br>Gln | TGG<br>Trp | TCA<br>Ser | GAG<br>Glu | TCC<br>Ser<br>55 | ACA<br>Thr | GCT<br>Ala | GCC<br>Ala | AAA<br>Lys | TAT<br>Tyr<br>60 | GGA<br>Gly | 552 |
| AGG<br>Arg | CTG<br>Leu | GAC<br>Asp | TCA<br>Ser<br>65 | GAA<br>Glu | GAA<br>Glu | GGG<br>Gly | GAT<br>Asp | GGA<br>Gly<br>70 | GCC<br>Ala | TGG<br>Trp | TGC<br>Cys | CCT<br>Pro | GAG<br>Glu<br>75 | ATT<br>Ile | CCA<br>Pro | 600 |
| GTG<br>Val | GAA<br>Glu | CCT<br>Pro<br>80 | GAT<br>Asp | GAC<br>Asp | CTG<br>Leu | AAG<br>Lys | GAG<br>Glu<br>85 | TTT<br>Phe | CTG<br>Leu | CAG<br>Gln | ATT<br>Ile | GAC<br>Asp<br>90 | TTG<br>Leu | CAC<br>His | ACC<br>Thr | 648 |

| | | | | | | | | | | | | | | | | |
|---|---|---|---|---|---|---|---|---|---|---|---|---|---|---|---|---|
| CTC | CAT | TTT | ATC | ACT | CTG | GTG | GGG | ACC | CAG | GGG | CGC | CAT | GCA | GGA | GGT | 696 |
| Leu | His | Phe | Ile | Thr | Leu | Val | Gly | Thr | Gln | Gly | Arg | His | Ala | Gly | Gly | |
| | 95 | | | | 100 | | | | | 105 | | | | | | |
| CAT | GGC | ATC | GAG | TTT | GCC | CCC | ATG | TAC | AAG | ATC | AAT | TAC | AGT | CGG | GAT | 744 |
| His | Gly | Ile | Glu | Phe | Ala | Pro | Met | Tyr | Lys | Ile | Asn | Tyr | Ser | Arg | Asp | |
| 110 | | | | | 115 | | | | | 120 | | | | | 125 | |
| GGC | ACT | CGC | TGG | ATC | TCT | TGG | CGG | AAC | CGT | CAT | GGG | AAA | CAG | GTG | CTG | 792 |
| Gly | Thr | Arg | Trp | Ile | Ser | Trp | Arg | Asn | Arg | His | Gly | Lys | Gln | Val | Leu | |
| | | | | 130 | | | | | 135 | | | | | 140 | | |
| GAT | GGA | AAT | AGT | AAC | CCC | TAT | GAC | ATT | TTC | CTA | AAG | GAC | TTG | GAG | CCG | 840 |
| Asp | Gly | Asn | Ser | Asn | Pro | Tyr | Asp | Ile | Phe | Leu | Lys | Asp | Leu | Glu | Pro | |
| | | | 145 | | | | | 150 | | | | | 155 | | | |
| CCC | ATT | GTA | GCC | AGA | TTT | GTC | CGG | TTC | ATT | CCA | GTC | ACC | GAC | CAC | TCC | 888 |
| Pro | Ile | Val | Ala | Arg | Phe | Val | Arg | Phe | Ile | Pro | Val | Thr | Asp | His | Ser | |
| | | 160 | | | | | 165 | | | | | 170 | | | | |
| ATG | AAT | GTG | TGT | ATG | AGA | GTG | GAG | CTT | TAC | GGC | TGT | GTC | TGG | CTA | GAT | 936 |
| Met | Asn | Val | Cys | Met | Arg | Val | Glu | Leu | Tyr | Gly | Cys | Val | Trp | Leu | Asp | |
| 175 | | | | | 180 | | | | | 185 | | | | | | |
| GGC | TTG | GTG | TCT | TAC | AAT | GCT | CCA | GCT | GGG | CAG | CAG | TTT | GTA | CTC | CCT | 984 |
| Gly | Leu | Val | Ser | Tyr | Asn | Ala | Pro | Ala | Gly | Gln | Gln | Phe | Val | Leu | Pro | |
| 190 | | | | | 195 | | | | | 200 | | | | | 205 | |
| GGA | GGT | TCC | ATC | ATT | TAT | CTG | AAT | GAT | TCT | GTC | TAT | GAT | GGA | GCT | GTT | 1032 |
| Gly | Gly | Ser | Ile | Ile | Tyr | Leu | Asn | Asp | Ser | Val | Tyr | Asp | Gly | Ala | Val | |
| | | | | 210 | | | | | 215 | | | | | 220 | | |
| GGA | TAC | AGC | ATG | ACA | GAA | GGG | CTA | GGC | CAA | TTG | ACC | GAT | GGT | GTG | TCT | 1080 |
| Gly | Tyr | Ser | Met | Thr | Glu | Gly | Leu | Gly | Gln | Leu | Thr | Asp | Gly | Val | Ser | |
| | | | | 225 | | | | | 230 | | | | | 235 | | |
| GGC | CTG | GAC | GAT | TTC | ACC | CAG | ACC | CAT | GAA | TAC | CAC | GTG | TGG | CCC | GGC | 1128 |
| Gly | Leu | Asp | Asp | Phe | Thr | Gln | Thr | His | Glu | Tyr | His | Val | Trp | Pro | Gly | |
| | | 240 | | | | | 245 | | | | | 250 | | | | |
| TAT | GAC | TAT | GTG | GGC | TGG | CGG | AAC | GAG | AGT | GCC | ACC | AAT | GGC | TAC | ATT | 1176 |
| Tyr | Asp | Tyr | Val | Gly | Trp | Arg | Asn | Glu | Ser | Ala | Thr | Asn | Gly | Tyr | Ile | |
| | 255 | | | | | 260 | | | | | 265 | | | | | |
| GAG | ATC | ATG | TTT | GAA | TTT | GAC | CGC | ATC | AGG | AAT | TTC | ACT | ACC | ATG | AAG | 1224 |
| Glu | Ile | Met | Phe | Glu | Phe | Asp | Arg | Ile | Arg | Asn | Phe | Thr | Thr | Met | Lys | |
| 270 | | | | | 275 | | | | | 280 | | | | | 285 | |
| GTC | CAC | TGC | AAC | AAC | ATG | TTT | GCT | AAA | GGT | GTG | AAG | ATC | TTT | AAG | GAG | 1272 |
| Val | His | Cys | Asn | Asn | Met | Phe | Ala | Lys | Gly | Val | Lys | Ile | Phe | Lys | Glu | |
| | | | | 290 | | | | | 295 | | | | | 300 | | |
| GTA | CAG | TGC | TAC | TTC | CGC | TCT | GAA | GCC | AGT | GAG | TGG | GAA | CCT | AAT | GCC | 1320 |
| Val | Gln | Cys | Tyr | Phe | Arg | Ser | Glu | Ala | Ser | Glu | Trp | Glu | Pro | Asn | Ala | |
| | | | 305 | | | | | 310 | | | | | 315 | | | |
| ATT | TCC | TTC | CCC | CTT | GTC | CTG | GAT | GAC | GTC | AAC | CCC | AGT | GCT | CGG | TTT | 1368 |
| Ile | Ser | Phe | Pro | Leu | Val | Leu | Asp | Asp | Val | Asn | Pro | Ser | Ala | Arg | Phe | |
| | | 320 | | | | | 325 | | | | | 330 | | | | |
| GTC | ACG | GTG | CCT | CTC | CAC | CAC | CGA | ATG | GCC | AGT | GCC | ATC | AAG | TGT | CAA | 1416 |
| Val | Thr | Val | Pro | Leu | His | His | Arg | Met | Ala | Ser | Ala | Ile | Lys | Cys | Gln | |
| | 335 | | | | | 340 | | | | | 345 | | | | | |
| TAC | CAT | TTT | GCA | GAT | ACC | TGG | ATG | ATG | TTC | AGT | GAG | ATC | ACC | TTC | CAA | 1464 |
| Tyr | His | Phe | Ala | Asp | Thr | Trp | Met | Met | Phe | Ser | Glu | Ile | Thr | Phe | Gln | |
| 350 | | | | | 355 | | | | | 360 | | | | | 365 | |
| TCA | GAT | GCT | GCA | ATG | TAC | AAC | AAC | TCT | GAA | GCC | CTG | CCC | ACC | TCT | CCT | 1512 |
| Ser | Asp | Ala | Ala | Met | Tyr | Asn | Asn | Ser | Glu | Ala | Leu | Pro | Thr | Ser | Pro | |
| | | | | 370 | | | | | 375 | | | | | 380 | | |
| ATG | GCA | CCC | ACA | ACC | TAT | GAT | CCA | ATG | CTT | AAA | GTT | GAT | GAC | AGC | AAC | 1560 |
| Met | Ala | Pro | Thr | Thr | Tyr | Asp | Pro | Met | Leu | Lys | Val | Asp | Asp | Ser | Asn | |
| | | | 385 | | | | | 390 | | | | | 395 | | | |
| ACT | CGG | ATC | CTG | ATT | GGC | TGC | TTG | GTG | GCC | ATC | ATC | TTT | ATC | CTC | CTG | 1608 |
| Thr | Arg | Ile | Leu | Ile | Gly | Cys | Leu | Val | Ala | Ile | Ile | Phe | Ile | Leu | Leu | |
| | | | 400 | | | | | 405 | | | | | 410 | | | |

-continued

| | | | | | | | | | | | | | | | | |
|---|---|---|---|---|---|---|---|---|---|---|---|---|---|---|---|---|
| GCC | ATC | ATT | GTC | ATC | ATC | CTC | TGG | AGG | CAG | TTC | TGG | CAG | AAA | ATG | CTG | 1656 |
| Ala | Ile | Ile | Val | Ile | Ile | Leu | Trp | Arg | Gln | Phe | Trp | Gln | Lys | Met | Leu | |
| 415 | | | | 420 | | | | | | 425 | | | | | | |
| GAG | AAG | GCT | TCT | CGG | AGG | ATG | CTG | GAT | GAT | GAA | ATG | ACA | GTC | AGC | CTT | 1704 |
| Glu | Lys | Ala | Ser | Arg | Arg | Met | Leu | Asp | Asp | Glu | Met | Thr | Val | Ser | Leu | |
| 430 | | | | | 435 | | | | 440 | | | | | | 445 | |
| TCC | CTG | CCA | AGT | GAT | TCT | AGC | ATG | TTC | AAC | AAT | AAC | CGC | TCC | TCA | TCA | 1752 |
| Ser | Leu | Pro | Ser | Asp | Ser | Ser | Met | Phe | Asn | Asn | Asn | Arg | Ser | Ser | Ser | |
| | | | | 450 | | | | | 455 | | | | | 460 | | |
| CCT | AGT | GAA | CAA | GGG | TCC | AAC | TCG | ACT | TAC | GAT | CGC | ATC | TTT | CCC | CTT | 1800 |
| Pro | Ser | Glu | Gln | Gly | Ser | Asn | Ser | Thr | Tyr | Asp | Arg | Ile | Phe | Pro | Leu | |
| | | | 465 | | | | | 470 | | | | | 475 | | | |
| CGC | CCT | GAC | TAC | CAG | GAG | CCA | TCC | AGG | CTG | ATA | CGA | AAA | CTC | CCA | GAA | 1848 |
| Arg | Pro | Asp | Tyr | Gln | Glu | Pro | Ser | Arg | Leu | Ile | Arg | Lys | Leu | Pro | Glu | |
| | | 480 | | | | | 485 | | | | | 490 | | | | |
| TTT | GCT | CCA | GGG | GAG | GAG | GAG | TCA | GGC | TGC | AGC | GGT | GTT | GTG | AAG | CCA | 1896 |
| Phe | Ala | Pro | Gly | Glu | Glu | Glu | Ser | Gly | Cys | Ser | Gly | Val | Val | Lys | Pro | |
| | 495 | | | | 500 | | | | | 505 | | | | | | |
| GTC | CAG | CCC | AGT | GGC | CCT | GAG | GGG | GTG | CCC | CAC | TAT | GCA | GAG | GCT | GAC | 1944 |
| Val | Gln | Pro | Ser | Gly | Pro | Glu | Gly | Val | Pro | His | Tyr | Ala | Glu | Ala | Asp | |
| 510 | | | | | 515 | | | | | 520 | | | | | 525 | |
| ATA | GTG | AAC | CTC | CAA | GGA | GTG | ACA | GGA | GGC | AAC | ACA | TAC | TCA | GTG | CCT | 1992 |
| Ile | Val | Asn | Leu | Gln | Gly | Val | Thr | Gly | Gly | Asn | Thr | Tyr | Ser | Val | Pro | |
| | | | | 530 | | | | | 535 | | | | | 540 | | |
| GCC | GTC | ACC | ATG | GAC | CTG | CTC | TCA | GGA | AAA | GAT | GTG | GCT | GTG | GAG | GAG | 2040 |
| Ala | Val | Thr | Met | Asp | Leu | Leu | Ser | Gly | Lys | Asp | Val | Ala | Val | Glu | Glu | |
| | | | 545 | | | | | 550 | | | | | 555 | | | |
| TTC | CCC | AGG | AAA | CTC | CTA | ACT | TTC | AAA | GAG | AAG | CTG | GGA | GAA | GGA | CAG | 2088 |
| Phe | Pro | Arg | Lys | Leu | Leu | Thr | Phe | Lys | Glu | Lys | Leu | Gly | Glu | Gly | Gln | |
| | | 560 | | | | | 565 | | | | | 570 | | | | |
| TTT | GGG | GAG | GTT | CAT | CTC | TGT | GAA | GTG | GAG | GGA | ATG | GAA | AAA | TTC | AAA | 2136 |
| Phe | Gly | Glu | Val | His | Leu | Cys | Glu | Val | Glu | Gly | Met | Glu | Lys | Phe | Lys | |
| | 575 | | | | 580 | | | | | 585 | | | | | | |
| GAC | AAA | GAT | TTT | GCC | CTA | GAT | GTC | AGT | GCC | AAC | CAG | CCT | GTC | CTG | GTG | 2184 |
| Asp | Lys | Asp | Phe | Ala | Leu | Asp | Val | Ser | Ala | Asn | Gln | Pro | Val | Leu | Val | |
| 590 | | | | | 595 | | | | | 600 | | | | | 605 | |
| GCT | GTG | AAA | ATG | CTC | CGA | GCA | GAT | GCC | AAC | AAG | AAT | GCC | AGG | AAT | GAT | 2232 |
| Ala | Val | Lys | Met | Leu | Arg | Ala | Asp | Ala | Asn | Lys | Asn | Ala | Arg | Asn | Asp | |
| | | | | 610 | | | | | 615 | | | | | | 620 | |
| TTT | CTT | AAG | GAG | ATA | AAG | ATC | ATG | TCT | CGG | CTC | AAG | GAC | CCA | AAC | ATC | 2280 |
| Phe | Leu | Lys | Glu | Ile | Lys | Ile | Met | Ser | Arg | Leu | Lys | Asp | Pro | Asn | Ile | |
| | | | | 625 | | | | 630 | | | | | 635 | | | |
| ATC | CAT | CTA | TTA | TCT | GTG | TGT | ATC | ACT | GAT | GAC | CCT | CTC | TGT | ATG | ATC | 2328 |
| Ile | His | Leu | Leu | Ser | Val | Cys | Ile | Thr | Asp | Asp | Pro | Leu | Cys | Met | Ile | |
| | | 640 | | | | | 645 | | | | | 650 | | | | |
| ACT | GAA | TAC | ATG | GAG | AAT | GGA | GAT | CTC | AAT | CAG | TTT | CTT | TCC | CGC | CAC | 2376 |
| Thr | Glu | Tyr | Met | Glu | Asn | Gly | Asp | Leu | Asn | Gln | Phe | Leu | Ser | Arg | His | |
| | 655 | | | | 660 | | | | | 665 | | | | | | |
| GAG | CCC | CCT | AAT | TCT | TCC | TCC | AGC | GAT | GTA | CGC | ACT | GTC | AGT | TAC | ACC | 2424 |
| Glu | Pro | Pro | Asn | Ser | Ser | Ser | Ser | Asp | Val | Arg | Thr | Val | Ser | Tyr | Thr | |
| 670 | | | | | 675 | | | | | 680 | | | | | 685 | |
| AAT | CTG | AAG | TTT | ATG | GCT | ACC | CAA | ATT | GCC | TCT | GGC | ATG | AAG | TAC | CTT | 2472 |
| Asn | Leu | Lys | Phe | Met | Ala | Thr | Gln | Ile | Ala | Ser | Gly | Met | Lys | Tyr | Leu | |
| | | | | 690 | | | | | 695 | | | | | 700 | | |
| TCC | TCT | CTT | AAT | TTT | GTT | CAC | CGA | GAT | CTG | GCC | ACA | CGA | AAC | TGT | TTA | 2520 |
| Ser | Ser | Leu | Asn | Phe | Val | His | Arg | Asp | Leu | Ala | Thr | Arg | Asn | Cys | Leu | |
| | | | 705 | | | | | 710 | | | | | 715 | | | |
| GTG | GGT | AAG | AAC | TAC | ACA | ATC | AAG | ATA | GCT | GAC | TTT | GGA | ATG | AGC | AGG | 2568 |
| Val | Gly | Lys | Asn | Tyr | Thr | Ile | Lys | Ile | Ala | Asp | Phe | Gly | Met | Ser | Arg | |
| | | 720 | | | | | 725 | | | | | 730 | | | | |

| | | | | | | | | | | | | | | | | |
|---|---|---|---|---|---|---|---|---|---|---|---|---|---|---|---|---|
| AAC | CTG | TAC | AGT | GGT | GAC | TAT | TAC | CGG | ATC | CAG | GGC | CGG | GCA | GTG | CTC | 2616 |
| Asn | Leu | Tyr | Ser | Gly | Asp | Tyr | Tyr | Arg | Ile | Gln | Gly | Arg | Ala | Val | Leu | |
| | 735 | | | | 740 | | | | | 745 | | | | | | |
| CCT | ATC | CGC | TGG | ATG | TCT | TGG | GAG | AGT | ATC | TTG | CTG | GGC | AAG | TTC | ACT | 2664 |
| Pro | Ile | Arg | Trp | Met | Ser | Trp | Glu | Ser | Ile | Leu | Leu | Gly | Lys | Phe | Thr | |
| 750 | | | | | 755 | | | | 760 | | | | | | 765 | |
| ACA | GCA | AGT | GAT | GTG | TGG | GCC | TTT | GGG | GTT | ACT | TTG | TGG | GAG | ACT | TTC | 2712 |
| Thr | Ala | Ser | Asp | Val | Trp | Ala | Phe | Gly | Val | Thr | Leu | Trp | Glu | Thr | Phe | |
| | | | | 770 | | | | | 775 | | | | | 780 | | |
| ACC | TTT | TGT | CAA | GAA | CAG | CCC | TAT | TCC | CAG | CTG | TCA | GAT | GAA | CAG | GTT | 2760 |
| Thr | Phe | Cys | Gln | Glu | Gln | Pro | Tyr | Ser | Gln | Leu | Ser | Asp | Glu | Gln | Val | |
| | | | 785 | | | | | 790 | | | | | 795 | | | |
| ATT | GAG | AAT | ACT | GGA | GAG | TTC | TTC | CGA | GAC | CAA | GGG | AGG | CAG | ACT | TAC | 2808 |
| Ile | Glu | Asn | Thr | Gly | Glu | Phe | Phe | Arg | Asp | Gln | Gly | Arg | Gln | Thr | Tyr | |
| | | | 800 | | | | | 805 | | | | | 810 | | | |
| CTC | CCT | CAA | CCA | GCC | ATT | TGT | CCT | GAC | TCT | GTG | TAT | AAG | CTG | ATG | CTC | 2856 |
| Leu | Pro | Gln | Pro | Ala | Ile | Cys | Pro | Asp | Ser | Val | Tyr | Lys | Leu | Met | Leu | |
| | 815 | | | | | 820 | | | | | 825 | | | | | |
| AGC | TGC | TGG | AGA | AGA | GAT | ACG | AAG | AAC | CGT | CCC | TCA | TTC | CAA | GAA | ATC | 2904 |
| Ser | Cys | Trp | Arg | Arg | Asp | Thr | Lys | Asn | Arg | Pro | Ser | Phe | Gln | Glu | Ile | |
| 830 | | | | | 835 | | | | | 840 | | | | | 845 | |
| CAC | CTT | CTG | CTC | CTT | CAA | CAA | GGC | GAC | GAG | TGATGCTGTC | | AGTGCCTGGC | | | | 2954 |
| His | Leu | Leu | Leu | Leu | Gln | Gln | Gly | Asp | Glu | | | | | | | |
| | | | | 850 | | | | | 855 | | | | | | | |

```
CATGTTCCTA CGGCTCAGGT CCTCCCTACA AGACCTACCA CTCACCCATG CCTATGCCAC        3014

TCCATCTGGA CATTTAATGA AACTGAGAGA CAGAGGCTTG TTTGCTTTGC CCTCTTTTCC        3074

TGGTCACCCC CACTCCCTAC CCCTGACTCA TATATACTTT TTTTTTTTAC ATTAAAGAAC        3134

TAAAAAAAAA AAAAAAAAG GCG                                                  3157
```

( 2 ) INFORMATION FOR SEQ ID NO:4:

( i ) SEQUENCE CHARACTERISTICS:
        ( A ) LENGTH: 855 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Ile | Leu | Ile | Pro | Arg | Met | Leu | Leu | Val | Leu | Phe | Leu | Leu | Pro |
| 1 | | | | 5 | | | | | 10 | | | | | 15 |
| Ile | Leu | Ser | Ser | Ala | Lys | Ala | Gln | Val | Asn | Pro | Ala | Ile | Cys | Arg | Tyr |
| | | | 20 | | | | | 25 | | | | | 30 | | |
| Pro | Leu | Gly | Met | Ser | Gly | Gly | Gln | Ile | Pro | Asp | Glu | Asp | Ile | Thr | Ala |
| | | | 35 | | | | | 40 | | | | | 45 | | |
| Ser | Ser | Gln | Trp | Ser | Glu | Ser | Thr | Ala | Ala | Lys | Tyr | Gly | Arg | Leu | Asp |
| | 50 | | | | | 55 | | | | | 60 | | | | |
| Ser | Glu | Glu | Gly | Asp | Gly | Ala | Trp | Cys | Pro | Glu | Ile | Pro | Val | Glu | Pro |
| 65 | | | | | 70 | | | | | 75 | | | | | 80 |
| Asp | Asp | Leu | Lys | Glu | Phe | Leu | Gln | Ile | Asp | Leu | His | Thr | Leu | His | Phe |
| | | | | 85 | | | | | 90 | | | | | 95 | |
| Ile | Thr | Leu | Val | Gly | Thr | Gln | Gly | Arg | His | Ala | Gly | Gly | His | Gly | Ile |
| | | | 100 | | | | | 105 | | | | | 110 | | |
| Glu | Phe | Ala | Pro | Met | Tyr | Lys | Ile | Asn | Tyr | Ser | Arg | Asp | Gly | Thr | Arg |
| | | 115 | | | | | 120 | | | | | 125 | | | |
| Trp | Ile | Ser | Trp | Arg | Asn | Arg | His | Gly | Lys | Gln | Val | Leu | Asp | Gly | Asn |
| | 130 | | | | | 135 | | | | | 140 | | | | |
| Ser | Asn | Pro | Tyr | Asp | Ile | Phe | Leu | Lys | Asp | Leu | Glu | Pro | Pro | Ile | Val |

|   |   |   |   |   |   |   |   |   |   |   |   |   |   |   |   |
|---|---|---|---|---|---|---|---|---|---|---|---|---|---|---|---|
| 145 |  |  |  | 150 |  |  |  | 155 |  |  |  | 160 |  |  |  |
| Ala | Arg | Phe | Val | Arg | Phe | Ile | Pro | Val | Thr | Asp | His | Ser | Met | Asn | Val |
|  |  |  |  | 165 |  |  |  | 170 |  |  |  | 175 |  |  |  |
| Cys | Met | Arg | Val | Glu | Leu | Tyr | Gly | Cys | Val | Trp | Leu | Asp | Gly | Leu | Val |
|  |  |  | 180 |  |  |  |  | 185 |  |  |  | 190 |  |  |  |
| Ser | Tyr | Asn | Ala | Pro | Ala | Gly | Gln | Gln | Phe | Val | Leu | Pro | Gly | Gly | Ser |
|  |  | 195 |  |  |  |  | 200 |  |  |  |  | 205 |  |  |  |
| Ile | Ile | Tyr | Leu | Asn | Asp | Ser | Val | Tyr | Asp | Gly | Ala | Val | Gly | Tyr | Ser |
|  |  | 210 |  |  |  | 215 |  |  |  |  | 220 |  |  |  |  |
| Met | Thr | Glu | Gly | Leu | Gly | Gln | Leu | Thr | Asp | Gly | Val | Ser | Gly | Leu | Asp |
| 225 |  |  |  |  | 230 |  |  |  |  | 235 |  |  |  |  | 240 |
| Asp | Phe | Thr | Gln | Thr | His | Glu | Tyr | His | Val | Trp | Pro | Gly | Tyr | Asp | Tyr |
|  |  |  |  | 245 |  |  |  |  | 250 |  |  |  | 255 |  |  |
| Val | Gly | Trp | Arg | Asn | Glu | Ser | Ala | Thr | Asn | Gly | Tyr | Ile | Glu | Ile | Met |
|  |  |  |  | 260 |  |  |  |  | 265 |  |  |  | 270 |  |  |
| Phe | Glu | Phe | Asp | Arg | Ile | Arg | Asn | Phe | Thr | Thr | Met | Lys | Val | His | Cys |
|  |  | 275 |  |  |  |  | 280 |  |  |  | 285 |  |  |  |  |
| Asn | Asn | Met | Phe | Ala | Lys | Gly | Val | Lys | Ile | Phe | Lys | Glu | Val | Gln | Cys |
|  | 290 |  |  |  |  | 295 |  |  |  |  | 300 |  |  |  |  |
| Tyr | Phe | Arg | Ser | Glu | Ala | Ser | Glu | Trp | Glu | Pro | Asn | Ala | Ile | Ser | Phe |
| 305 |  |  |  |  | 310 |  |  |  |  | 315 |  |  |  |  | 320 |
| Pro | Leu | Val | Leu | Asp | Asp | Val | Asn | Pro | Ser | Ala | Arg | Phe | Val | Thr | Val |
|  |  |  |  | 325 |  |  |  |  | 330 |  |  |  | 335 |  |  |
| Pro | Leu | His | His | Arg | Met | Ala | Ser | Ala | Ile | Lys | Cys | Gln | Tyr | His | Phe |
|  |  |  | 340 |  |  |  |  | 345 |  |  |  |  | 350 |  |  |
| Ala | Asp | Thr | Trp | Met | Met | Phe | Ser | Glu | Ile | Thr | Phe | Gln | Ser | Asp | Ala |
|  |  | 355 |  |  |  |  | 360 |  |  |  |  | 365 |  |  |  |
| Ala | Met | Tyr | Asn | Asn | Ser | Glu | Ala | Leu | Pro | Thr | Ser | Pro | Met | Ala | Pro |
|  | 370 |  |  |  |  | 375 |  |  |  |  | 380 |  |  |  |  |
| Thr | Thr | Tyr | Asp | Pro | Met | Leu | Lys | Val | Asp | Asp | Ser | Asn | Thr | Arg | Ile |
| 385 |  |  |  |  | 390 |  |  |  |  | 395 |  |  |  |  | 400 |
| Leu | Ile | Gly | Cys | Leu | Val | Ala | Ile | Ile | Phe | Ile | Leu | Leu | Ala | Ile | Ile |
|  |  |  |  | 405 |  |  |  |  | 410 |  |  |  | 415 |  |  |
| Val | Ile | Ile | Leu | Trp | Arg | Gln | Phe | Trp | Gln | Lys | Met | Leu | Glu | Lys | Ala |
|  |  |  | 420 |  |  |  |  | 425 |  |  |  |  | 430 |  |  |
| Ser | Arg | Arg | Met | Leu | Asp | Asp | Glu | Met | Thr | Val | Ser | Leu | Ser | Leu | Pro |
|  |  | 435 |  |  |  |  | 440 |  |  |  |  | 445 |  |  |  |
| Ser | Asp | Ser | Ser | Met | Phe | Asn | Asn | Arg | Ser | Ser | Pro | Ser | Glu |  |  |
|  | 450 |  |  |  |  | 455 |  |  |  | 460 |  |  |  |  |  |
| Gln | Gly | Ser | Asn | Ser | Thr | Tyr | Asp | Arg | Ile | Phe | Pro | Leu | Arg | Pro | Asp |
| 465 |  |  |  |  | 470 |  |  |  |  | 475 |  |  |  |  | 480 |
| Tyr | Gln | Glu | Pro | Ser | Arg | Leu | Ile | Arg | Lys | Leu | Pro | Glu | Phe | Ala | Pro |
|  |  |  |  | 485 |  |  |  |  | 490 |  |  |  |  | 495 |  |
| Gly | Glu | Glu | Glu | Ser | Gly | Cys | Ser | Gly | Val | Val | Lys | Pro | Val | Gln | Pro |
|  |  |  | 500 |  |  |  |  | 505 |  |  |  |  | 510 |  |  |
| Ser | Gly | Pro | Glu | Gly | Val | Pro | His | Tyr | Ala | Glu | Ala | Asp | Ile | Val | Asn |
|  |  | 515 |  |  |  |  | 520 |  |  |  |  | 525 |  |  |  |
| Leu | Gln | Gly | Val | Thr | Gly | Gly | Asn | Thr | Tyr | Ser | Val | Pro | Ala | Val | Thr |
|  | 530 |  |  |  |  | 535 |  |  |  |  | 540 |  |  |  |  |
| Met | Asp | Leu | Leu | Ser | Gly | Lys | Asp | Val | Ala | Val | Glu | Glu | Phe | Pro | Arg |
| 545 |  |  |  |  | 550 |  |  |  |  | 555 |  |  |  |  | 560 |
| Lys | Leu | Leu | Thr | Phe | Lys | Glu | Lys | Leu | Gly | Glu | Gly | Gln | Phe | Gly | Glu |
|  |  |  |  | 565 |  |  |  |  | 570 |  |  |  |  | 575 |  |

| Val | His | Leu | Cys | Glu | Val | Glu | Gly | Met | Glu | Lys | Phe | Lys | Asp | Lys | Asp |
|---|---|---|---|---|---|---|---|---|---|---|---|---|---|---|---|
| | | | 580 | | | | 585 | | | | | | 590 | | |
| Phe | Ala | Leu | Asp | Val | Ser | Ala | Asn | Gln | Pro | Val | Leu | Val | Ala | Val | Lys |
| | | 595 | | | | | 600 | | | | | 605 | | | |
| Met | Leu | Arg | Ala | Asp | Ala | Asn | Lys | Asn | Ala | Arg | Asn | Asp | Phe | Leu | Lys |
| | 610 | | | | | 615 | | | | | 620 | | | | |
| Glu | Ile | Lys | Ile | Met | Ser | Arg | Leu | Lys | Asp | Pro | Asn | Ile | Ile | His | Leu |
| 625 | | | | | 630 | | | | | 635 | | | | | 640 |
| Leu | Ser | Val | Cys | Ile | Thr | Asp | Asp | Pro | Leu | Cys | Met | Ile | Thr | Glu | Tyr |
| | | | | 645 | | | | | 650 | | | | | 655 | |
| Met | Glu | Asn | Gly | Asp | Leu | Asn | Gln | Phe | Leu | Ser | Arg | His | Glu | Pro | Pro |
| | | | 660 | | | | | 665 | | | | | 670 | | |
| Asn | Ser | Ser | Ser | Ser | Asp | Val | Arg | Thr | Val | Ser | Tyr | Thr | Asn | Leu | Lys |
| | | | 675 | | | | | 680 | | | | | 685 | | |
| Phe | Met | Ala | Thr | Gln | Ile | Ala | Ser | Gly | Met | Lys | Tyr | Leu | Ser | Ser | Leu |
| | | 690 | | | | | 695 | | | | | 700 | | | |
| Asn | Phe | Val | His | Arg | Asp | Leu | Ala | Thr | Arg | Asn | Cys | Leu | Val | Gly | Lys |
| 705 | | | | | 710 | | | | | 715 | | | | | 720 |
| Asn | Tyr | Thr | Ile | Lys | Ile | Ala | Asp | Phe | Gly | Met | Ser | Arg | Asn | Leu | Tyr |
| | | | | 725 | | | | | 730 | | | | | 735 | |
| Ser | Gly | Asp | Tyr | Tyr | Arg | Ile | Gln | Gly | Arg | Ala | Val | Leu | Pro | Ile | Arg |
| | | | 740 | | | | | 745 | | | | | 750 | | |
| Trp | Met | Ser | Trp | Glu | Ser | Ile | Leu | Leu | Gly | Lys | Phe | Thr | Thr | Ala | Ser |
| | | 755 | | | | | 760 | | | | | 765 | | | |
| Asp | Val | Trp | Ala | Phe | Gly | Val | Thr | Leu | Trp | Glu | Thr | Phe | Thr | Phe | Cys |
| | 770 | | | | | 775 | | | | | 780 | | | | |
| Gln | Glu | Gln | Pro | Tyr | Ser | Gln | Leu | Ser | Asp | Glu | Gln | Val | Ile | Glu | Asn |
| 785 | | | | | 790 | | | | | 795 | | | | | 800 |
| Thr | Gly | Glu | Phe | Phe | Arg | Asp | Gln | Gly | Arg | Gln | Thr | Tyr | Leu | Pro | Gln |
| | | | | 805 | | | | | 810 | | | | | 815 | |
| Pro | Ala | Ile | Cys | Pro | Asp | Ser | Val | Tyr | Lys | Leu | Met | Leu | Ser | Cys | Trp |
| | | | 820 | | | | | 825 | | | | | 830 | | |
| Arg | Arg | Asp | Thr | Lys | Asn | Arg | Pro | Ser | Phe | Gln | Glu | Ile | His | Leu | Leu |
| | | 835 | | | | | 840 | | | | | 845 | | | |
| Leu | Leu | Gln | Gln | Gly | Asp | Glu | | | | | | | | | |
| 850 | | | | | 855 | | | | | | | | | | |

( 2 ) INFORMATION FOR SEQ ID NO:5:

( i ) SEQUENCE CHARACTERISTICS:
        ( A ) LENGTH: 3157 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

```
CGCCTTTTTT TTTTTTTTTT TTAGTTCTTT AATGTAAAAA AAAAAAGTAT ATATGAGTCA    60
GGGGTAGGGA GTGGGGGTGA CCAGGAAAAG AGGGCAAAGC AAACAAGCCT CTGTCTCTCA   120
GTTTCATTAA ATGTCCAGAT GGAGTGGCAT AGGCATGGGT GAGTGGTAGG TCTTGTAGGG   180
AGGACCTGAG CCGTAGGAAC ATGGCCAGGC ACTGACAGCA TCACTCGTCG CCTTGTTGAA   240
GGAGCAGAAG GTGGATTTCT TGGAATGAGG GACGGTTCTT CGTATCTCTT CTCCAGCAGC   300
```

| | | | | | |
|---|---|---|---|---|---|
| TGAGCATCAG | CTTATACACA | GAGTCAGGAC | AAATGGCTGG | TTGAGGGAGG | TAAGTCTGCC | 360 |
| TCCCTTGGTC | TCGGAAGAAC | TCTCCAGTAT | TCTCAATAAC | CTGTTCATCT | GACAGCTGGG | 420 |
| AATAGGGCTG | TTCTTGACAA | AAGGTGAAAG | TCTCCCACAA | AGTAACCCCA | AAGGCCCACA | 480 |
| CATCACTTGC | TGTAGTGAAC | TTGCCCAGCA | AGATACTCTC | CCAAGACATC | CAGCGGATAG | 540 |
| GGAGCACTGC | CCGGCCCTGG | ATCCGGTAAT | AGTCACCACT | GTACAGGTTC | CTGCTCATTC | 600 |
| CAAAGTCAGC | TATCTTGATT | GTGTAGTTCT | TACCCACTAA | ACAGTTTCGT | GTGGCCAGAT | 660 |
| CTCGGTGAAC | AAAATTAAGA | GAGGAAAGGT | ACTTCATGCC | AGAGGCAATT | TGGGTAGCCA | 720 |
| TAAACTTCAG | ATTGGTGTAA | CTGACAGTGC | GTACATCGCT | GGAGGAAGAA | TTAGGGGCT | 780 |
| CGTGGCGGGA | AAGAAACTGA | TTGAGATCTC | CATTCTCCAT | GTATTCAGTG | ATCATACAGA | 840 |
| GAGGGTCATC | AGTGATACAC | ACAGATAATA | GATGGATGAT | GTTTGGGTCC | TTGAGCCGAG | 900 |
| ACATGATCTT | TATCTCCTTA | AGAAAATCAT | TCCTGGCATT | CTTGTTGGCA | TCTGCTCGGA | 960 |
| GCATTTTCAC | AGCCACCAGG | ACAGGCTGGT | TGGCACTGAC | ATCTAGGGCA | AATCTTTGT | 1020 |
| CTTTGAATTT | TTCCATTCCC | TCCACTTCAC | AGAGATGAAC | CTCCCCAAAC | TGTCCTTCTC | 1080 |
| CCAGCTTCTC | TTTGAAAGTT | AGGAGTTTCC | TGGGAACTC | CTCCACAGCC | ACATCTTTTC | 1140 |
| CTGAGAGCAG | GTCCATGGTG | ACGGCAGGCA | CTGAGTATGT | GTTGCCTCCT | GTCACTCCTT | 1200 |
| GGAGGTTCAC | TATGTCAGCC | TCTGCATAGT | GGGGCACCCC | CTCAGGGCCA | CTGGGCTGGA | 1260 |
| CTGGCTTCAC | AACACCGCTG | CAGCCTGACT | CCTCCTCCCC | TGGAGCAAAT | CTGGGAGTT | 1320 |
| TTCGTATCAG | CCTGGATGGC | TCCTGGTAGT | CAGGGCGAAG | GGGAAAGATG | CGATCGTAAG | 1380 |
| TCGAGTTGGA | CCCTTGTTCA | CTAGGTGATG | AGGAGCGGTT | ATTGTTGAAC | ATGCTAGAAT | 1440 |
| CACTTGGCAG | GGAAAGGCTG | ACTGTCATTT | CATCATCCAG | CATCCTCCGA | GAAGCCTTCT | 1500 |
| CCAGCATTTT | CTGCCAGAAC | TGCCTCCAGA | GGATGATGAC | AATGATGGCC | AGGAGGATAA | 1560 |
| AGATGATGGC | CACCAAGCAG | CCAATCAGGA | TCCGAGTGTT | GCTGTCATCA | ACTTTAAGCA | 1620 |
| TTGGATCATA | GGTTGTGGGT | GCCATAGGAG | AGGTGGGCAG | GGCTTCAGAG | TTGTTGTACA | 1680 |
| TTGCAGCATC | TGATTGGAAG | GTGATCTCAC | TGAACATCAT | CCAGGTATCT | GCAAAATGGT | 1740 |
| ATTGACACTT | GATGGCACTG | GCCATTCGGT | GGTGGAGAGG | CACCGTGACA | AACCGAGCAC | 1800 |
| TGGGGTTGAC | GTCATCCAGG | ACAAGGGGGA | AGGAAATGGC | ATTAGGTTCC | CACTCACTGG | 1860 |
| CTTCAGAGCG | GAAGTAGCAC | TGTACCTCCT | TAAAGATCTT | CACACCTTTA | GCAAACATGT | 1920 |
| TGTTGCAGTG | GACCTTCATG | GTAGTGAAAT | TCCTGATGCG | GTCAAATTCA | AACATGATCT | 1980 |
| CAATGTAGCC | ATTGGTGGCA | CTCTCGTTCC | GCCAGCCCAC | ATAGTCATAG | CCGGGCCACA | 2040 |
| CGTGGTATTC | ATGGGTCTGG | GTGAAATCGT | CCAGGCCAGA | CACACCATCG | GTCAATTGGC | 2100 |
| CTAGCCCTTC | TGTCATGCTG | TATCCAACAG | CTCCATCATA | GACAGAATCA | TTCAGATAAA | 2160 |
| TGATGGAACC | TCCAGGGAGT | ACAAACTGCT | GCCAGCTGG | AGCATTGTAA | GACACCAAGC | 2220 |
| CATCTAGCCA | GACACAGCCG | TAAAGCTCCA | CTCTCATACA | CACATTCATG | GAGTGGTCGG | 2280 |
| TGACTGGAAT | GAACCGGACA | AATCTGGCTA | CAATGGGCGG | CTCCAAGTCC | TTTAGGAAAA | 2340 |
| TGTCATAGGG | GTTACTATTT | CCATCCAGCA | CCTGTTTCCC | ATGACGGTTC | CGCCAAGAGA | 2400 |
| TCCAGCGAGT | GCCATCCCGA | CTGTAATTGA | TCTTGTACAT | GGGGCAAAC | TCGATGCCAT | 2460 |
| GACCTCCTGC | ATGGCGCCCC | TGGGTCCCCA | CCAGAGTGAT | AAAATGGAGG | GTGTGCAAGT | 2520 |
| CAATCTGCAG | AAACTCCTTC | AGGTCATCAG | GTTCCACTGG | AATCTCAGGG | CACCAGGCTC | 2580 |
| CATCCCCTTC | TTCTGAGTCC | AGCCTTCCAT | ATTTGGCAGC | TGTGGACTCT | GACCACTGAC | 2640 |
| TGGAAGCTGT | GATGTCCTCA | TCTGGAATCT | GGCCTCCTGA | CATGCCCAGA | GGATAGCGGC | 2700 |

| | | | | | |
|---|---|---|---|---|---|
|ATATAGCTGG|ATTAACCTGA|GCTTTTGCAG|AACTCAAGAT|AGGCAGCAGC|AGGAACAGCA 2760|
|CCAAGAGCAT|TCTGGGAATC|AGGATCATCT|CAGAAGATGG|TGTTGGAACT|GGAGTATCAA 2820|
|CGGGTGCAGA|GCATTCTCTG|TGGAGCAGGA|TCCTCAAAAA|CAGCTGGCCT|CTGCTTCTCT 2880|
|TCAATTATTT|CAGCTTCTTT|AGAATAATTC|AAGCCACAAA|CCTTGGAACT|TTCTAGAGCA 2940|
|CTGAACCCCA|GGCAACTTGT|AGGTCTCCCT|TGATGGAGGC|TTTGAGAGCC|AGACTTCTTG 3000|
|TAAAGAGACC|TCCTTTCTCT|GAGCTCTGGA|GCTATCACCA|GCTCTTCTCT|GTTTGTAGTT 3060|
|AATCTGGGAT|TGCACAGTCT|CCAAGATGAG|CAAGAAAAGA|AGTGAGCAAA|CAGGAAAGGG 3120|
|AGGATGGAAA|GAGATCATGG|ACTCGTGCCG|CTCGTGC| |3157|

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

His Arg Asp Leu Ala Ala
    1                  5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: unknown ( i i ) MOLECULE TYPE: peptide ( i x ) FEATURE:
        ( A ) NAME/KEY: Peptide
        ( B ) LOCATION: 5
        ( D ) OTHER INFORMATION: /note="X can be serine or
                phenylalanine"

( x i ) SEQUENCE DESCRIPTION: SEQ ID NO:7:

Ser Asp Val Trp Xaa Tyr
    1                  5

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:8:

Thr Tyr Ala Xaa Pro Xaa Xaa Xaa Pro Gly
    1                  5                          10

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

```
GGAATTCCCA YMGNRA Y YTN RCNRC-
NMG                                                                    28
```

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
GGAATTCC YW  YNSWGGTNTG  SAGNST                                        26
```

(2) INFORMATION FOR SEQ ID NO:11:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (xi) SEQUENCE DESCRIPTION: SEQ ID NO:11:

```
His Phe Asp Pro Ala Lys Asp Cys Arg Tyr Ala Leu Gly Met Gln Asp
 1               5                  10                  15

Arg Thr Ile
```

(2) INFORMATION FOR SEQ ID NO:12:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (xi) SEQUENCE DESCRIPTION: SEQ ID NO:12:

```
Arg Pro Pro Phe Ser Gln Leu His Arg Phe Leu Ala Glu Asp Ala Leu
 1               5                  10                  15

Asn Thr Val
```

(2) INFORMATION FOR SEQ ID NO:13:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:13:

```
Pro Ala Met Ala Trp Glu Gly Glu Pro Met Arg His Asn Leu
 1               5                  10
```

(2) INFORMATION FOR SEQ ID NO:14:

(i) SEQUENCE CHARACTERISTICS:
        (A) LENGTH: 17 amino acids
        (B) TYPE: amino acid
        (D) TOPOLOGY: unknown (ii) MOLECULE TYPE: peptide (xi) SEQUENCE DESCRIPTION: SEQ ID NO:14:

```
Cys Trp Ser Arg Glu Ser Glu Gln Arg Pro Pro Phe Ser Gln Leu His
1               5                   10                  15
Arg
```

( 2 ) INFORMATION FOR SEQ ID NO:15:

( i ) SEQUENCE CHARACTERISTICS:
        ( A ) LENGTH: 13 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:15:

```
Pro Asn Gly Ser Ala Tyr Ser Gly Asp Tyr Met Glu Pro
1               5                   10
```

( 2 ) INFORMATION FOR SEQ ID NO:16:

( i ) SEQUENCE CHARACTERISTICS:
        ( A ) LENGTH: 50 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:16:

```
Pro Asn Gly Ser Ala Leu Leu Leu Ser Asn Pro Ala Tyr Arg Leu Leu
1               5                   10                  15
Leu Ala Thr Tyr Ala Arg Pro Pro Arg Gly Pro Gly Pro Pro Thr Pro
            20                  25                  30
Ala Trp Ala Lys Pro Thr Asn Thr Gln Ala Tyr Ser Gly Asp Tyr Met
            35                  40                  45
Glu Pro
    50
```

( 2 ) INFORMATION FOR SEQ ID NO:17:

( i ) SEQUENCE CHARACTERISTICS:
        ( A ) LENGTH: 44 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:17:

```
Leu Val Ala Val Lys Ile Leu Arg Pro Asp Ala Thr Lys Asn Ala Arg
1               5                   10                  15
Asn Asp Phe Leu Lys Glu Val Lys Ile Met Ser Arg Leu Lys Asp Pro
            20                  25                  30
Asn Ile Ile Arg Leu Leu Gly Val Cys Val Gln Asp
            35                  40
```

( 2 ) INFORMATION FOR SEQ ID NO:18:

( i ) SEQUENCE CHARACTERISTICS:
        ( A ) LENGTH: 50 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:18:

```
Leu Val Ala Val Lys Ile Leu Arg Pro Asp Ala Thr Lys Asn Ala Ser
1               5                   10                  15
```

```
Phe Ser Leu Phe Ser Arg Asn Asp Phe Leu Lys Glu Val Lys Ile Met
         20                  25                  30
Ser Arg Leu Lys Asp Pro Asn Ile Ile Arg Leu Leu Gly Val Cys Val
         35                  40                  45
Gln Asp
 50
```

( 2 ) INFORMATION FOR SEQ ID NO:19:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:19:

```
Asn Pro Xaa Tyr
 1
```

( 2 ) INFORMATION FOR SEQ ID NO:20:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:20:

```
Arg Xaa Arg Arg
 1
```

( 2 ) INFORMATION FOR SEQ ID NO:21:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:21:

```
Pro Arg Gly Pro Gly Pro Pro Thr Pro Ala Trp
 1               5                   10
```

( 2 ) INFORMATION FOR SEQ ID NO:22:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:22:

```
Pro Arg Val Pro Ile Pro Pro Arg Pro Thr Arg
 1               5                   10
```

( 2 ) INFORMATION FOR SEQ ID NO:23:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:23:

```
Ala  Pro  Pro  Lys  Lys  Pro  Pro  Arg  Pro  Gly  Ala
1              5                        10
```

( 2 ) INFORMATION FOR SEQ ID NO:24:

( i ) SEQUENCE CHARACTERISTICS:
    ( A ) LENGTH: 11 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:24:

```
Arg  Pro  Arg  Pro  Leu  Pro  Pro  Leu  Pro  Pro  Thr
1              5                        10
```

( 2 ) INFORMATION FOR SEQ ID NO:25:

( i ) SEQUENCE CHARACTERISTICS:
    ( A ) LENGTH: 11 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:25:

```
Pro  Thr  Met  Pro  Pro  Pro  Leu  Pro  Pro  Val  Pro
1              5                        10
```

( 2 ) INFORMATION FOR SEQ ID NO:26:

( i ) SEQUENCE CHARACTERISTICS:
    ( A ) LENGTH: 11 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:26:

```
Pro  Ala  Tyr  Pro  Pro  Pro  Pro  Val  Pro  Val  Pro
1              5                        10
```

( 2 ) INFORMATION FOR SEQ ID NO:27:

( i ) SEQUENCE CHARACTERISTICS:
    ( A ) LENGTH: 11 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:27:

```
Ala  Pro  Ala  Val  Pro  Pro  Ala  Arg  Pro  Gly  Ser
1              5                        10
```

( 2 ) INFORMATION FOR SEQ ID NO:28:

( i ) SEQUENCE CHARACTERISTICS:
    ( A ) LENGTH: 11 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:28:

```
Gly  Ala  Pro  Pro  Val  Pro  Ser  Arg  Pro  Gly  Ala
1              5                        10
```

( 2 ) INFORMATION FOR SEQ ID NO:29:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:29:

```
Pro  Pro  Arg  Pro  Leu  Pro  Val  Ala  Pro  Gly  Ser
1                   5                        10
```

( 2 ) INFORMATION FOR SEQ ID NO:30:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:30:

```
Pro  Ala  Pro  Ala  Leu  Pro  Pro  Lys  Pro  Pro  Lys
1                   5                        10
```

( 2 ) INFORMATION FOR SEQ ID NO:31:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:31:

```
Ala  Pro  Lys  Pro  Met  Pro  Pro  Arg  Pro  Pro  Leu
1                   5                        10
```

( 2 ) INFORMATION FOR SEQ ID NO:32:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:32:

```
Pro  Ala  Leu  Pro  Pro  Pro  Pro  Arg  Pro  Val  Ala
1                   5                        10
```

( 2 ) INFORMATION FOR SEQ ID NO:33:

( i ) SEQUENCE CHARACTERISTICS:
        ( A ) LENGTH: 7 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:33:

```
Xaa  Pro  Xaa  Pro  Pro  Xaa  Pro
1                   5
```

( 2 ) INFORMATION FOR SEQ ID NO:34:

( i ) SEQUENCE CHARACTERISTICS:
        ( A ) LENGTH: 4 amino acids
        ( B ) TYPE: amino acid (D) TOPOLOGY: unknown (ii) MOLECULE TYPE: peptide (xi) SEQUENCE DESCRIPTION: SEQ ID NO:34:

Tyr Glu Leu Met
1

(2) INFORMATION FOR SEQ ID NO:35:

(i) SEQUENCE CHARACTERISTICS:
(A) LENGTH: 4 amino acids
(B) TYPE: amino acid
(D) TOPOLOGY: unknown (ii) MOLECULE TYPE: peptide (xi) SEQUENCE DESCRIPTION: SEQ ID NO:35:

Tyr Xaa Xaa Met
1

(2) INFORMATION FOR SEQ ID NO:36:

(i) SEQUENCE CHARACTERISTICS:
(A) LENGTH: 4 amino acids
(B) TYPE: amino acid
(D) TOPOLOGY: unknown (ii) MOLECULE TYPE: peptide (xi) SEQUENCE DESCRIPTION: SEQ ID NO:36:

Tyr Leu Ser Arg
1

(2) INFORMATION FOR SEQ ID NO:37:

(i) SEQUENCE CHARACTERISTICS:
(A) LENGTH: 4 amino acids
(B) TYPE: amino acid
(D) TOPOLOGY: unknown (ii) MOLECULE TYPE: peptide (xi) SEQUENCE DESCRIPTION: SEQ ID NO:37:

Tyr Ser Gly Asp
1

(2) INFORMATION FOR SEQ ID NO:38:

(i) SEQUENCE CHARACTERISTICS:
(A) LENGTH: 4 amino acids
(B) TYPE: amino acid
(D) TOPOLOGY: unknown (ii) MOLECULE TYPE: peptide (xi) SEQUENCE DESCRIPTION: SEQ ID NO:38:

Tyr Met Glu Pro
1

(2) INFORMATION FOR SEQ ID NO:39:

(i) SEQUENCE CHARACTERISTICS:
(A) LENGTH: 6 amino acids
(B) TYPE: amino acid
(D) TOPOLOGY: unknown (ii) MOLECULE TYPE: peptide (xi) SEQUENCE DESCRIPTION: SEQ ID NO:39:

```
        Glu  Lys  Ala  Ser  Arg  Arg
        1                   5
```

(2) INFORMATION FOR SEQ ID NO:40:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (xi) SEQUENCE DESCRIPTION: SEQ ID NO:40:

```
        Arg  Arg  Leu  Leu  Ser  Lys  Ala  Glu  Arg  Arg
        1                   5                        10
```

(2) INFORMATION FOR SEQ ID NO:41:

(i) SEQUENCE CHARACTERISTICS:
        (A) LENGTH: 4 amino acids
        (B) TYPE: amino acid
        (D) TOPOLOGY: unknown (ii) MOLECULE TYPE: peptide (xi) SEQUENCE DESCRIPTION: SEQ ID NO:41:

```
        Pro  Xaa  Xaa  Pro
        1
```

(2) INFORMATION FOR SEQ ID NO:42:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO:42:

```
        Pro  Xaa  Xaa  Xaa  Pro
        1                   5
```

(2) INFORMATION FOR SEQ ID NO:43:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO:43:

```
        Pro  Xaa  Pro  Pro  Xaa  Pro
        1                   5
```